(12) United States Patent
Taintor

(10) Patent No.: US 8,241,865 B2
(45) Date of Patent: *Aug. 14, 2012

(54) DIRECT ANTIMICROBIAL SUSCEPTIBILITY ASSAY WITH CONCURRENT QUALITATION/QUANTITATION

(75) Inventor: Read Robert Taintor, North Salt Lake, UT (US)

(73) Assignee: Kwikculture LLC, N.S.L, UT (US)

( * ) Notice: Subject to any disclaimer, the term of this patent is extended or adjusted under 35 U.S.C. 154(b) by 467 days.

This patent is subject to a terminal disclaimer.

(21) Appl. No.: 12/423,807

(22) Filed: Apr. 15, 2009

(65) Prior Publication Data

US 2010/0099137 A1    Apr. 22, 2010

Related U.S. Application Data

(63) Continuation-in-part of application No. 12/102,875, filed on Apr. 15, 2008, now Pat. No. 7,960,136.

(51) Int. Cl.
*C12Q 1/02* (2006.01)
*C12Q 1/18* (2006.01)
*C12M 1/22* (2006.01)
*C12M 1/34* (2006.01)

(52) U.S. Cl. ...... 435/29; 435/32; 435/287.1; 435/288.3; 435/810

(58) Field of Classification Search .......... None
See application file for complete search history.

(56) References Cited

U.S. PATENT DOCUMENTS

| | | |
|---|---|---|
| 3,715,280 A | 2/1973 | Farmer |
| 4,701,850 A | 10/1987 | Gibbs |
| 4,778,758 A | 10/1988 | Ericsson |
| 5,344,761 A | 9/1994 | Citri |
| 5,464,755 A | 11/1995 | Bochner |
| 5,618,729 A | 4/1997 | Izraelevitz et al. |
| 5,627,045 A | 5/1997 | Bochner |
| 5,629,169 A | 5/1997 | Izraelevitz et al. |
| 5,789,191 A | 8/1998 | Mayer |
| 5,922,593 A | 7/1999 | Livingston |
| 6,046,021 A | 4/2000 | Bochner |
| 6,107,054 A | 8/2000 | Gibbs |
| 6,153,400 A | 11/2000 | Matsumura et al. |
| 6,238,879 B1 | 5/2001 | Gibbs |
| 6,251,624 B1 | 6/2001 | Matsumura et al. |
| 6,265,182 B1 | 7/2001 | Kocagoz |
| 6,387,651 B1 | 5/2002 | Bochner |
| 6,416,969 B2 | 7/2002 | Matsumura et al. |
| 6,611,765 B2 | 8/2003 | Boeufgras |
| 6,665,429 B1 | 12/2003 | Wang |
| 6,984,499 B2 | 1/2006 | Chen |
| 7,262,021 B1 | 8/2007 | Taintor |

OTHER PUBLICATIONS

Habermeier, HK. "Apparatus for measuring zones of inhibition", Medical Instrumentation, 12(3):165-166(1978).

*Primary Examiner* — Vera Afremova

(57) ABSTRACT

An antimicrobial susceptibility assay enabling a more rapid and direct result, including an assay dish including at least one chamber, at least one growth medium carried by the assay dish, at least one antimicrobial agent sample positionable at a sample location adjacent a growth medium in the assay dish, at least one interpretive indication positionable at a predetermined distance from the sample location adjacent a growth medium in the assay dish, and at least one interfitting element, said at least one interfitting element configured cooperate with the assay dish to enable at least one of: a) more accurately positioning said at least one antimicrobial sample at the sample position in contact with the growth medium; b) carrying said at least one interpretive indication positionable at a predetermined distance from said sample position; said assay enabling the interpretative indication to be visually compared with a margin of a zone of inhibition of microbial organism growth on said growth medium to determine an assay result.

20 Claims, 27 Drawing Sheets

FIG. 1B
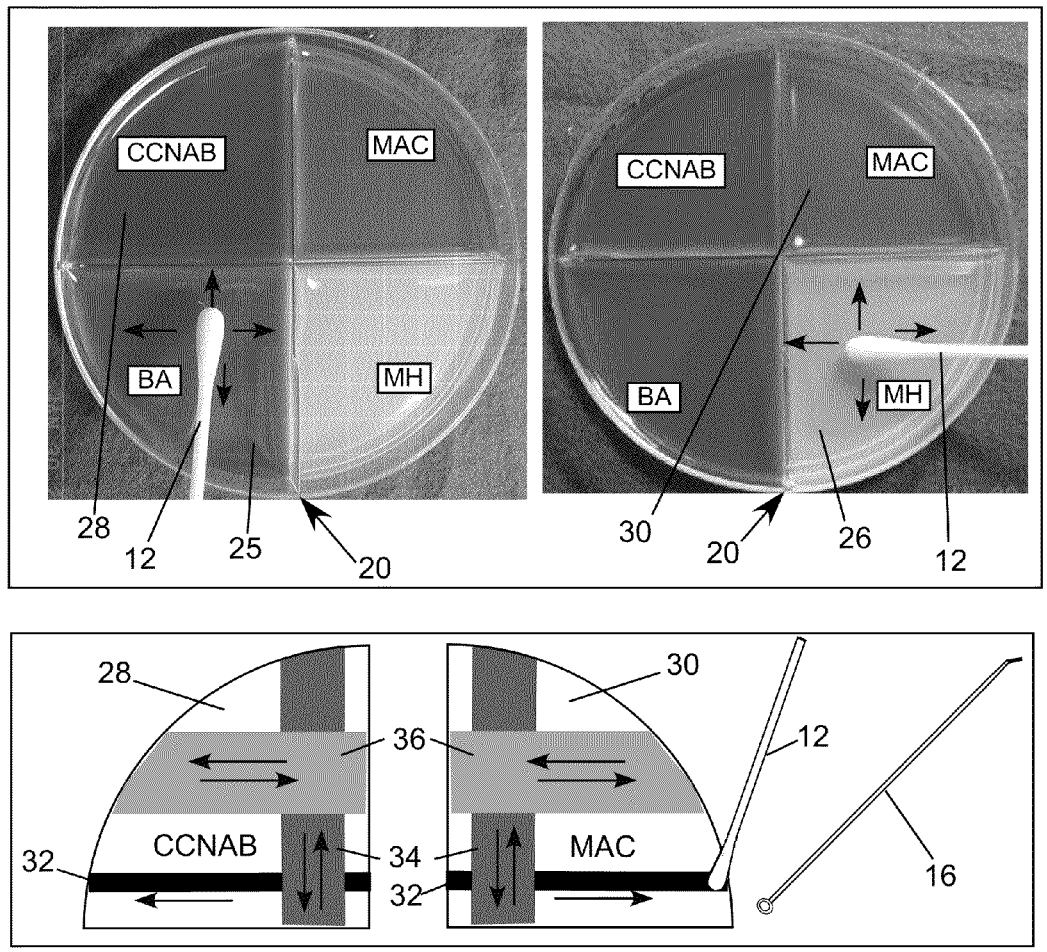
FIG. 1C
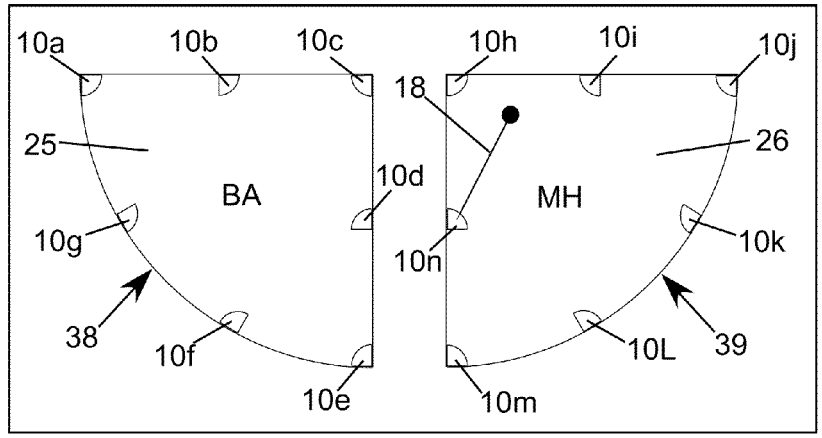
FIG. 1D

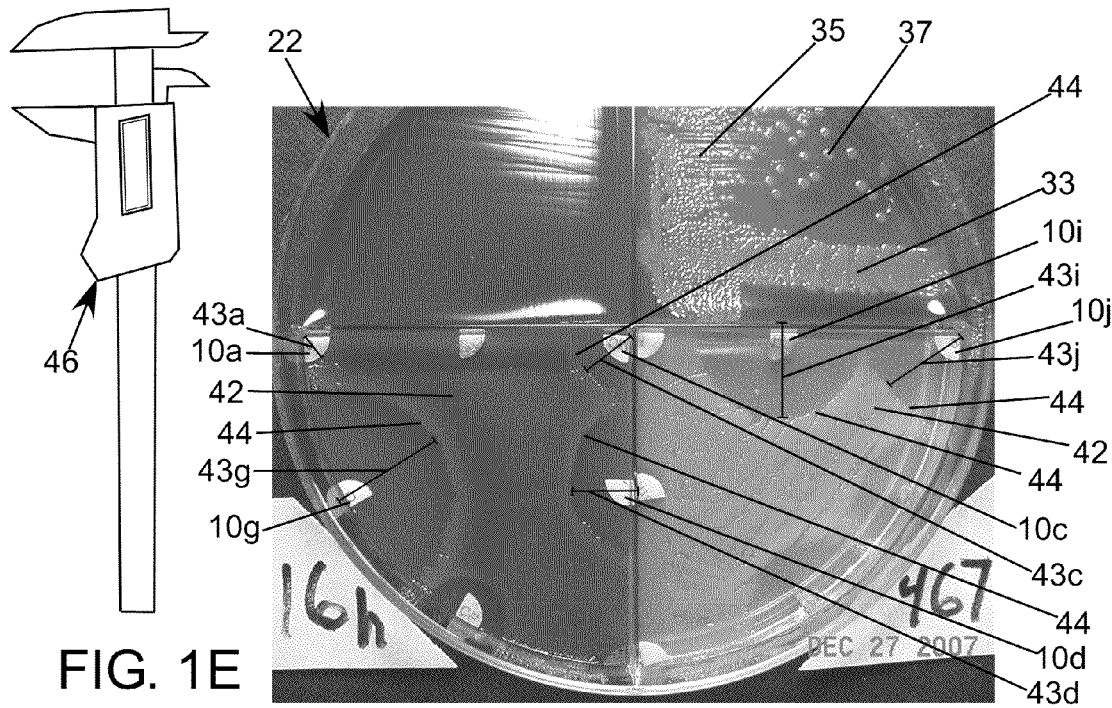

FIG. 1E

| LABEL | Antimicrobial agent | Radial zone of inhibition millimeters | Compare radial measurement with value below to determine antimicrobial susceptibility in terms of R,I or S | | | Grade R/I/S |
|---|---|---|---|---|---|---|
| | | | Resistant | Intermediate | Susceptible | |
| a | Ampicillin | 3 | ≤6.5 | 7 - 8 | ≥ 8.5 | R |
| c | Amoxicillin/Clavulanate | 8 | ≤6.5 | 7 - 8.5 | ≥ 9 | I |
| d | Cefazolin | 8.5 | ≤7 | 7.5 - 8.5 | ≥ 9 | I |
| e | Ciprofloxicin | 3 | ≤7.5 | 8 - 10 | ≥ 10.5 | R |
| f | Cefoxitin | 7 | ≤7 | 7.5 - 8.5 | ≥ 9 | R |
| g | Cefotetan | 16 | ≤6.5 | 6.5-7.5 | ≥ 8 | S |
| h | Trimethoprim/Sulfa. | 3 | ≤5 | 5.5 - 7.5 | ≥ 8 | R |
| i | Piperacillin/Tazobactam | 11 | ≤8.5 | 9 - 10 | ≥ 10.5 | S |
| j | Nitrofurantoin | 11 | ≤7 | 7.5 - 8 | ≥ 8.5 | S |
| k | Gentamicin | 9 | ≤6 | 6.5 - 7 | ≥ 7.5 | S |
| L | Amikacin | 10.5 | ≤7 | 7.5 - 8 | ≥ 8.5 | S |
| m | Levofloxicin | 3 | ≤6.5 | 7 - 8 | ≥ 8.5 | R |
| n | Doxycylcine | 3 | ≤6 | 6.5 - 7.5 | ≥ 8 | R |

FIG. 1F

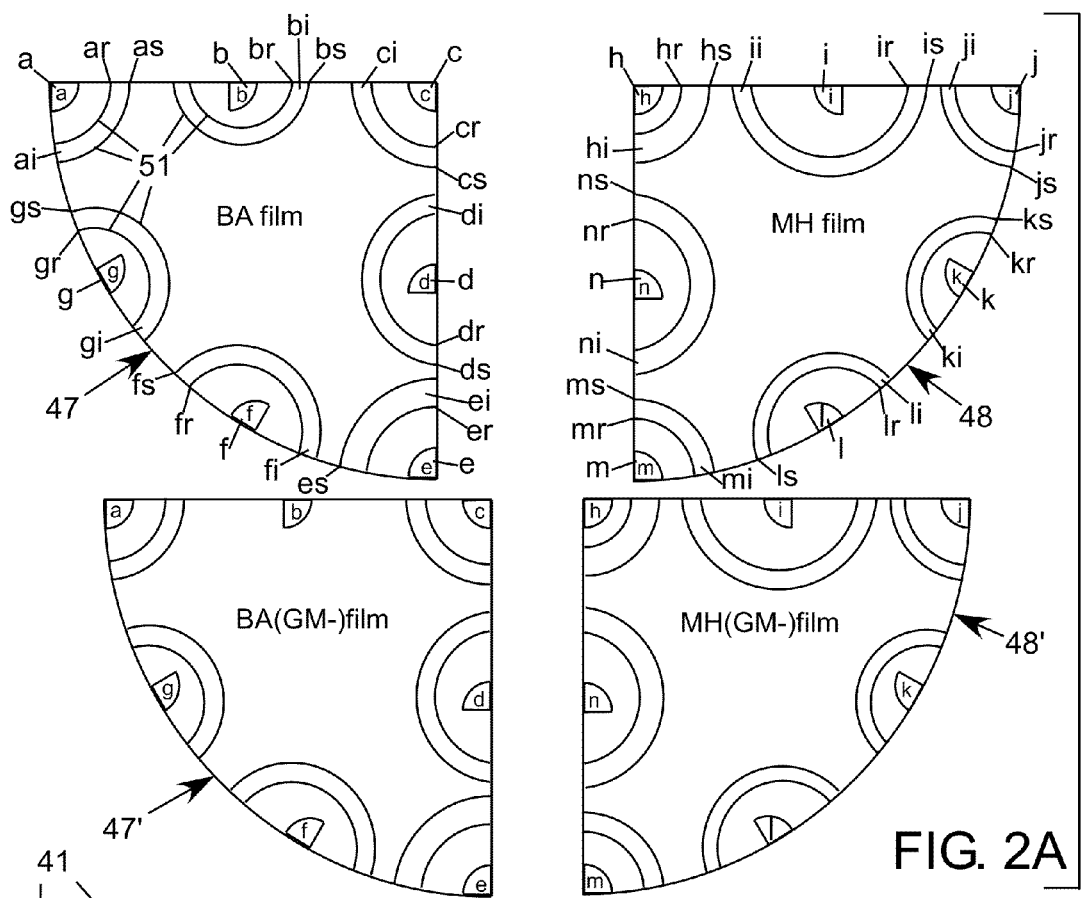
FIG. 2A
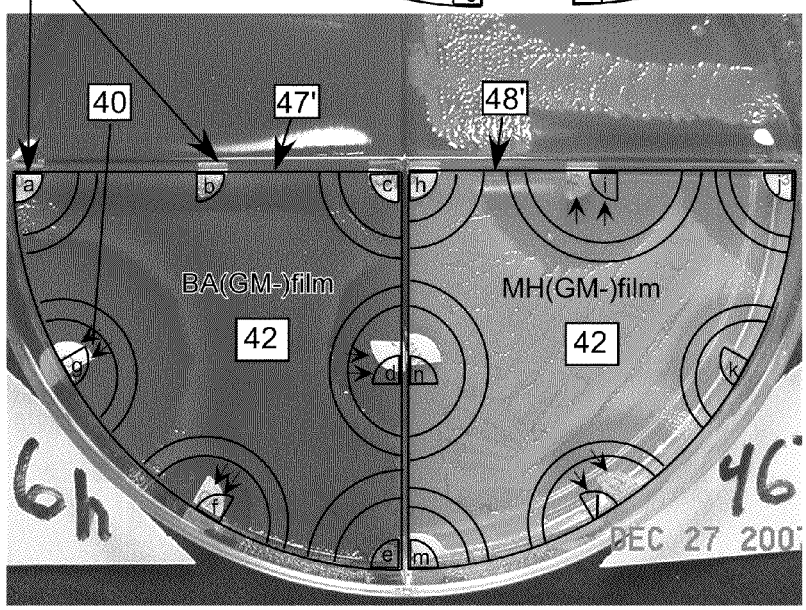
FIG. 2B
| DAST Results | | |
|---|---|---|
| test | FIG.1F | FIG.2B |
| a | R | R |
| c | I | I |
| d | I | I |
| e | R | R |
| f | R | R |
| g | S | S |
| h | R | R |
| i | S | S |
| j | S | S |
| k | S | S |
| l | S | S |
| m | R | R |
| n | R | R |
FIG. 2C

FIG. 2E

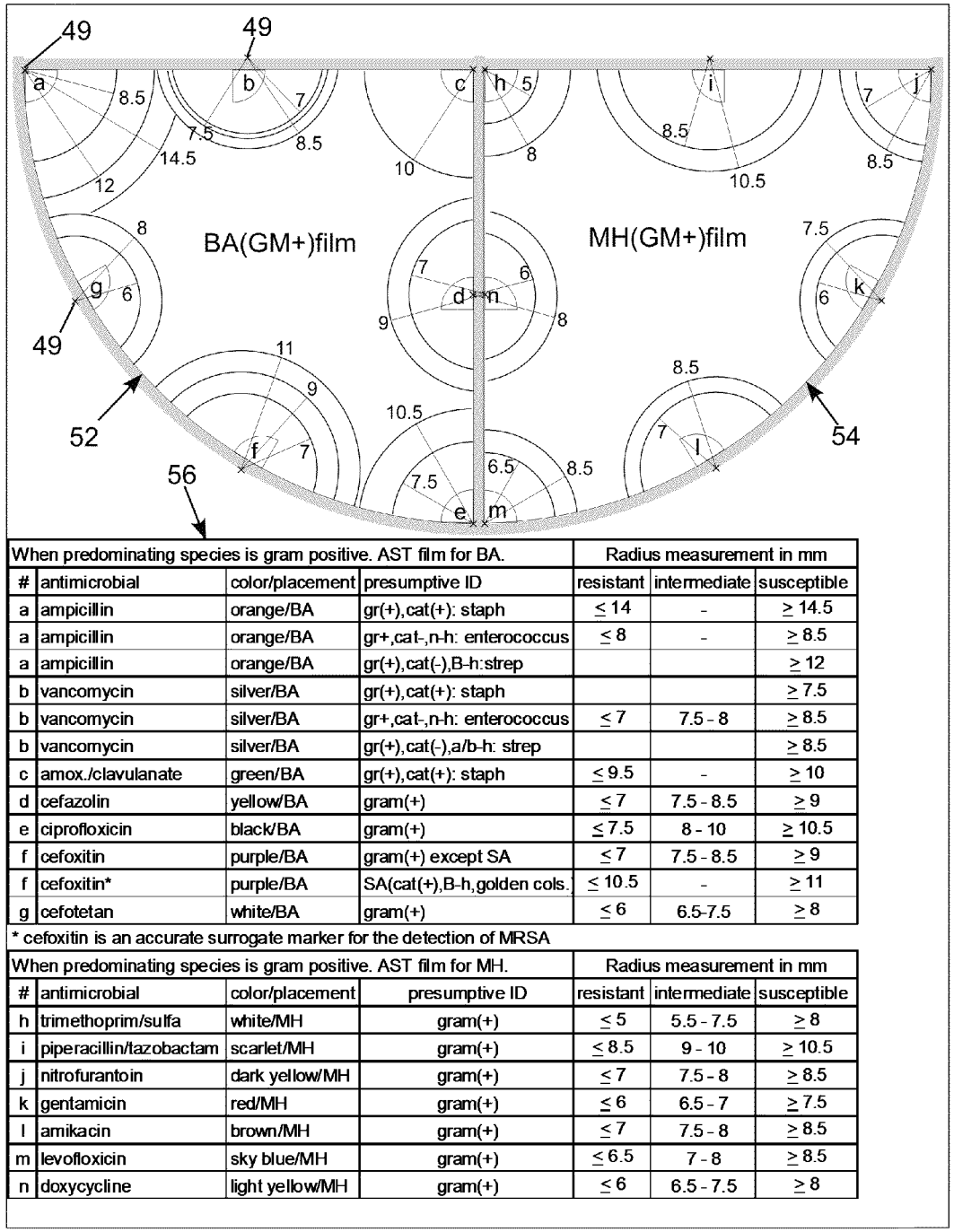

| When predominating species is gram positive. AST film for BA. | | | Radius measurement in mm | | |
|---|---|---|---|---|---|
| # | antimicrobial | color/placement | presumptive ID | resistant | intermediate | susceptible |
| a | ampicillin | orange/BA | gr(+),cat(+): staph | ≤ 14 | - | ≥ 14.5 |
| a | ampicillin | orange/BA | gr+,cat-,n-h: enterococcus | ≤ 8 | - | ≥ 8.5 |
| a | ampicillin | orange/BA | gr(+),cat(-),B-h:strep | | | ≥ 12 |
| b | vancomycin | silver/BA | gr(+),cat(+): staph | | | ≥ 7.5 |
| b | vancomycin | silver/BA | gr+,cat-,n-h: enterococcus | ≤ 7 | 7.5 - 8 | ≥ 8.5 |
| b | vancomycin | silver/BA | gr(+),cat(-),a/b-h: strep | | | ≥ 8.5 |
| c | amox./clavulanate | green/BA | gr(+),cat(+): staph | ≤ 9.5 | - | ≥ 10 |
| d | cefazolin | yellow/BA | gram(+) | ≤ 7 | 7.5 - 8.5 | ≥ 9 |
| e | ciprofloxicin | black/BA | gram(+) | ≤ 7.5 | 8 - 10 | ≥ 10.5 |
| f | cefoxitin | purple/BA | gram(+) except SA | ≤ 7 | 7.5 - 8.5 | ≥ 9 |
| f | cefoxitin* | purple/BA | SA(cat(+),B-h,golden cols. | ≤ 10.5 | - | ≥ 11 |
| g | cefotetan | white/BA | gram(+) | ≤ 6 | 6.5-7.5 | ≥ 8 |

* cefoxitin is an accurate surrogate marker for the detection of MRSA

| When predominating species is gram positive. AST film for MH. | | | Radius measurement in mm | | |
|---|---|---|---|---|---|
| # | antimicrobial | color/placement | presumptive ID | resistant | intermediate | susceptible |
| h | trimethoprim/sulfa | white/MH | gram(+) | ≤ 5 | 5.5 - 7.5 | ≥ 8 |
| i | piperacillin/tazobactam | scarlet/MH | gram(+) | ≤ 8.5 | 9 - 10 | ≥ 10.5 |
| j | nitrofurantoin | dark yellow/MH | gram(+) | ≤ 7 | 7.5 - 8 | ≥ 8.5 |
| k | gentamicin | red/MH | gram(+) | ≤ 6 | 6.5 - 7 | ≥ 7.5 |
| l | amikacin | brown/MH | gram(+) | ≤ 7 | 7.5 - 8 | ≥ 8.5 |
| m | levofloxicin | sky blue/MH | gram(+) | ≤ 6.5 | 7 - 8 | ≥ 8.5 |
| n | doxycycline | light yellow/MH | gram(+) | ≤ 6 | 6.5 - 7.5 | ≥ 8 |

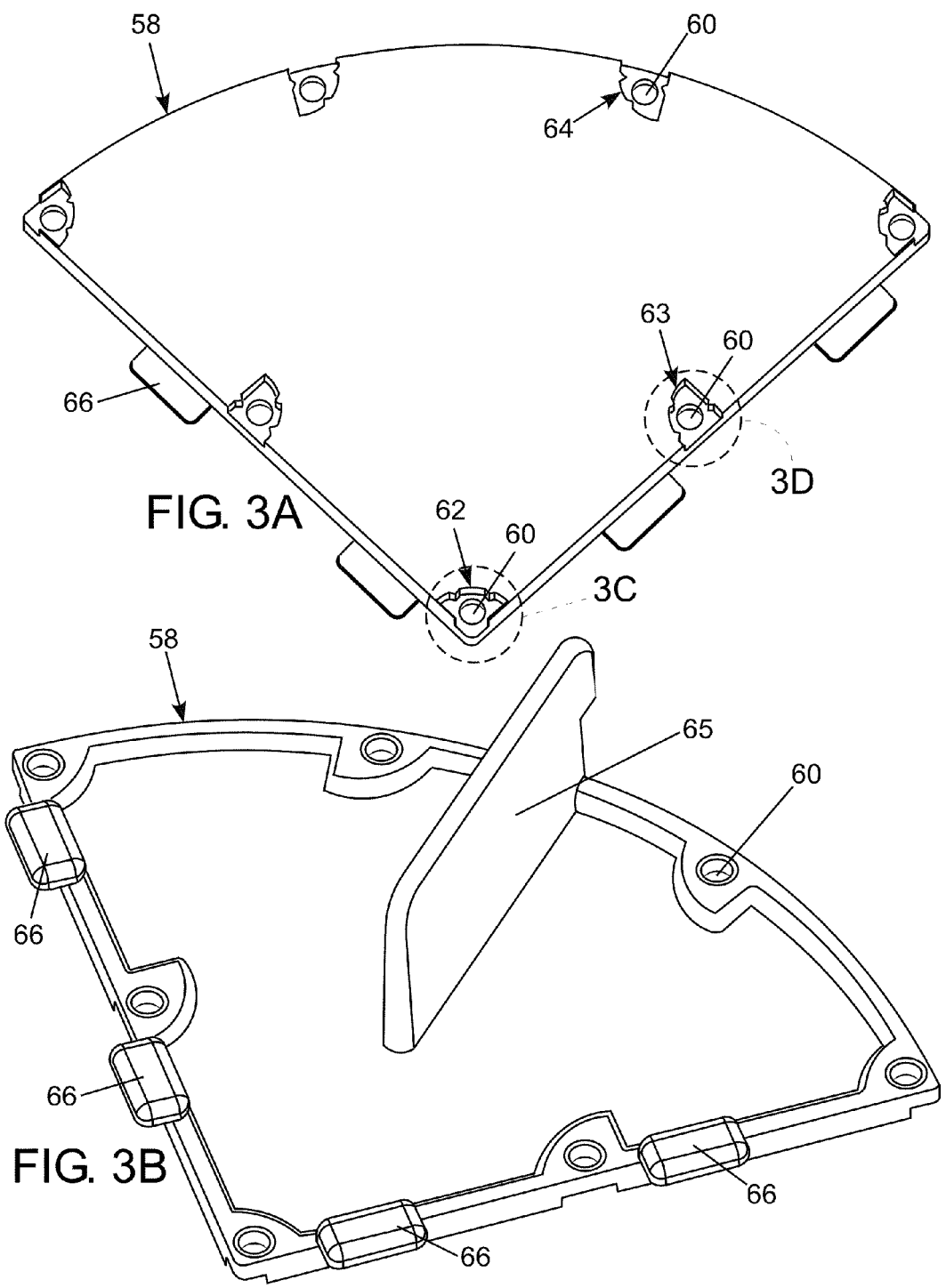

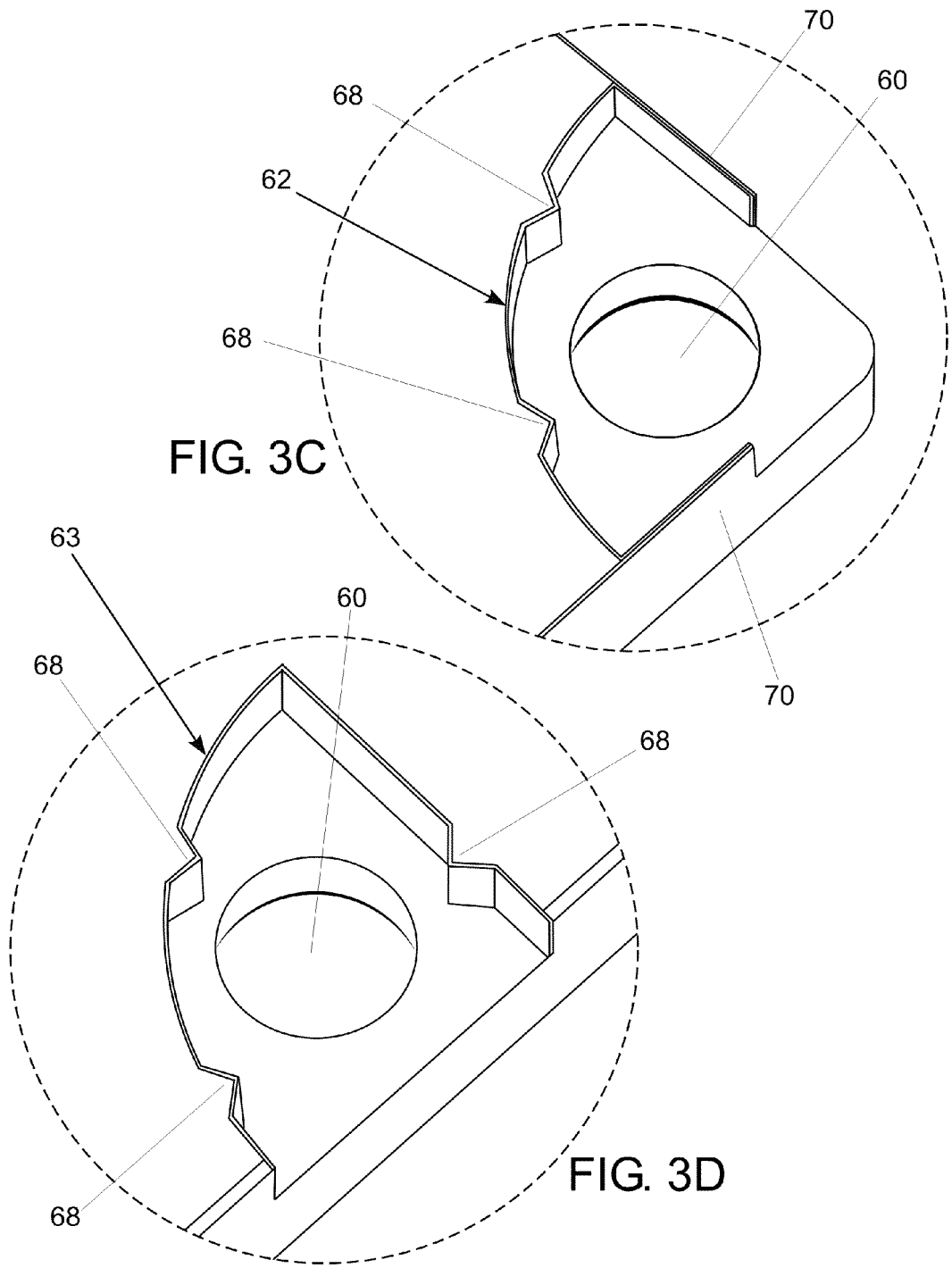

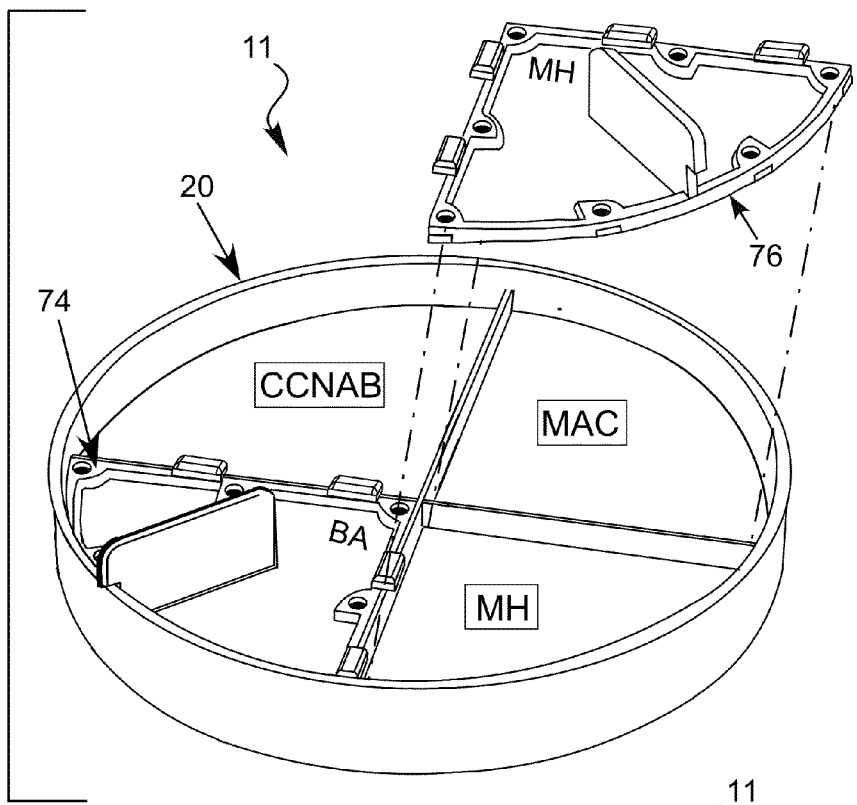
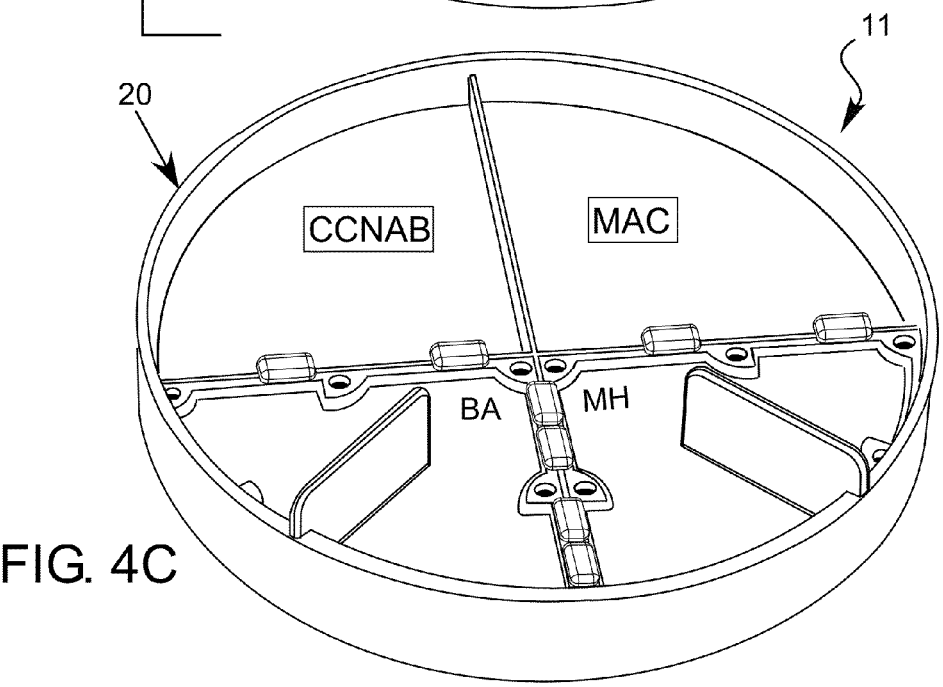

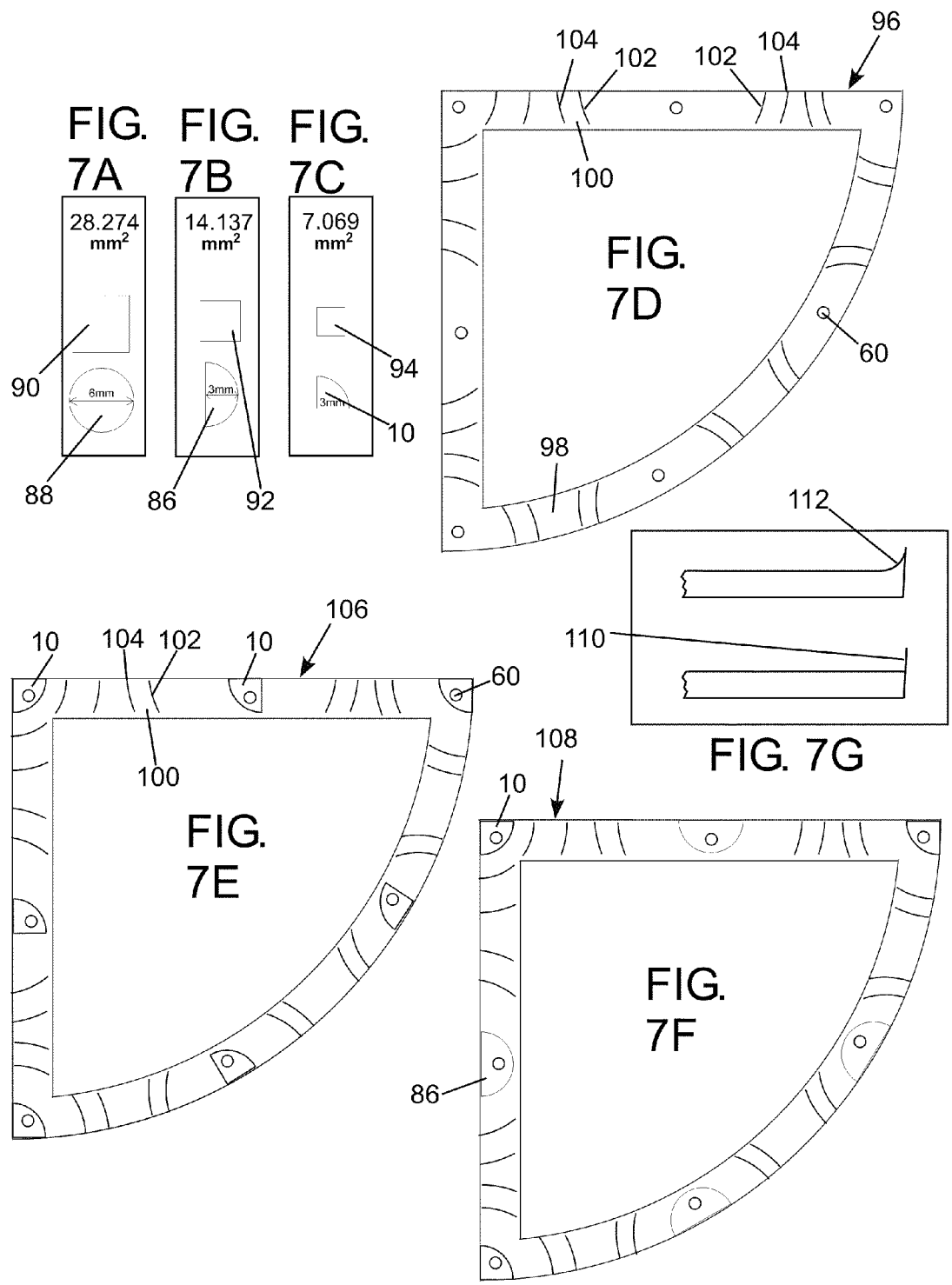

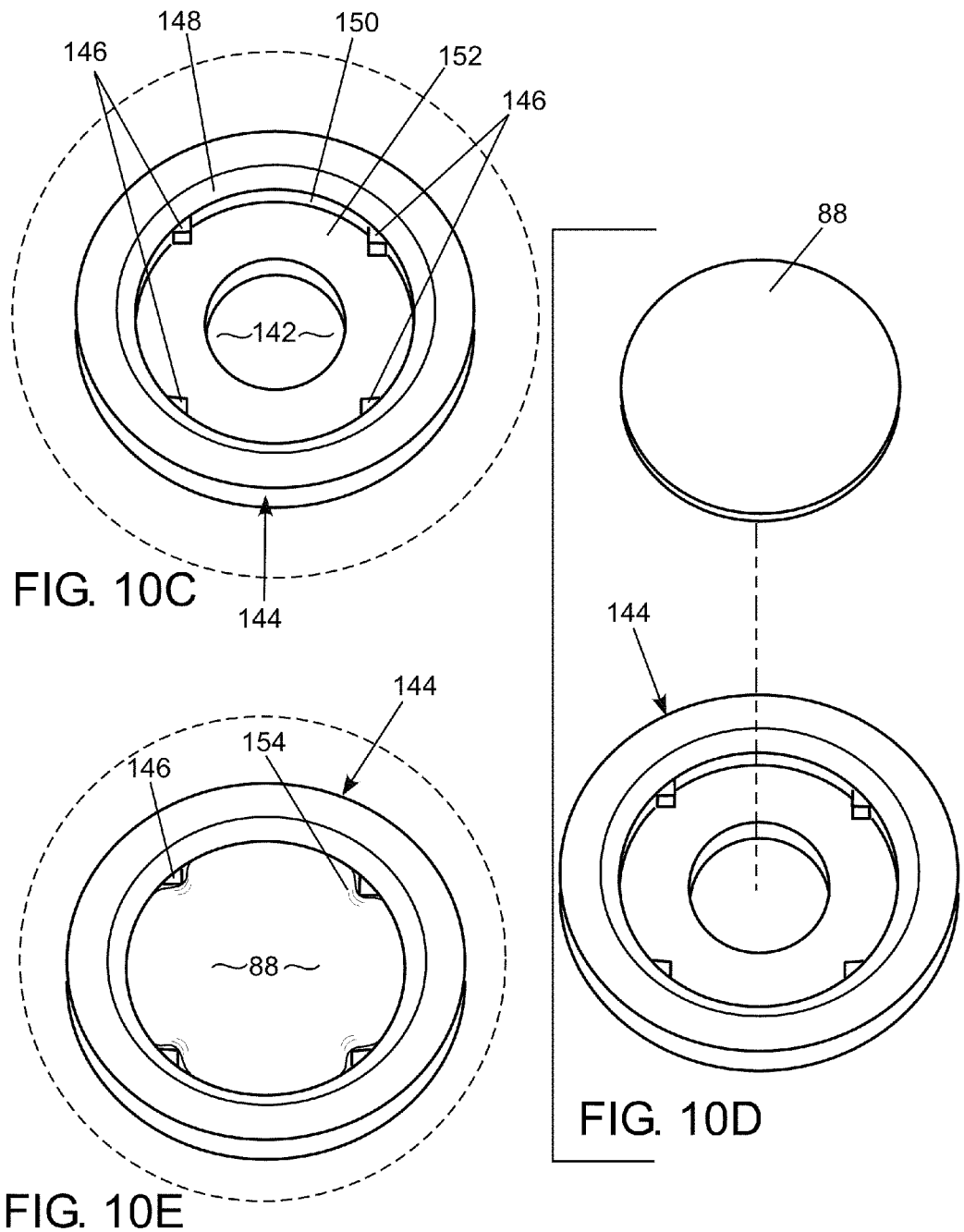

DIRECT ANTIMICROBIAL SUSCEPTIBILITY ASSAY WITH CONCURRENT QUALITATION/QUANTITATION

RELATED APPLICATIONS

This application is a Continuation-In-Part of U.S. patent application Ser. No. 12/102,875, filed Apr. 15, 2008 now U.S. Pat. No. 7,960,136.

BACKGROUND

1. Field of Invention

The present invention relates to antimicrobial susceptibility testing using antimicrobial agent diffusion in a growth medium, including for example agar-based media. More specifically, the invention relates to an improved assay enabling a result with less required time and/or difficulty.

2. Discussion of Most Relevant Prior Art

The disclosure of U.S. Pat. No. 7,262,021, issued Aug. 28, 2007 to the inventor, describes diagnostic apparatus and methods usable in performing direct antimicrobial susceptibility testing. In addition, the disclosure teaches examples of how such testing can run concurrently with isolation, quantitative analysis and presumptive identification of an organism under test. The assay of the prior disclosure provides a way to obtain next-morning antimicrobial susceptibility results. This gives the health care provider the option to prescribe an antimicrobial agent based on evidence instead of merely making assumptions about an infection organism's susceptibility to a particular antimicrobial agent prescribed.

The short delay in prescribing until after the results of the testing have been obtained enables a better choice of antibiotic to treat the patient. It generally allows for a treatment using a narrower spectrum, less expensive—yet effective—antimicrobial agent. This helps to preserve the efficacious effects of more powerful antimicrobial agents for future use. Antimicrobial susceptibility information obtained from an assay in accordance with the disclosure of U.S. Pat. No. 7,262,021 can be shown to be substantially identical to antimicrobial susceptibility information obtained using recognized testing methodology, specifically a Kirby-Bauer standardized antimicrobial susceptibility testing disk diffusion method that utilizes standardized full-size antimicrobial susceptibility test disks.

The user of the above-mentioned method places antimicrobial papers into one or several chambers containing growth media, as well as an organism sample spread thereon so as to facilitate growing an organism lawn. This placement can be done by individually placing the papers into the corners and abutting them against one or more walls along the edge of a chamber of the plate in a specific order. Following the incubation period, the user reads the results using a measuring device (such as a micrometer) to give a distance value in millimeters, as measured from the edge of the chamber at an antimicrobial agent sample location to a margin of a zone of inhibition. This value is then compared with a distance value on a zone radius interpretive table or chart to determine a result as to each agent. The result is given conventionally in terms of "resistant", "intermediate", or "susceptible". The radius distance value generally speaking can usually also be doubled and compared to a standard Kirby-Bauer zone diameter interpretive chart to obtain an accurate test result.

The disclosure of U.S. Pat. No. 7,262,021 is hereby incorporated into this disclosure by reference for the disclosure therein consistent with the present disclosure. To the extent (if any) that it is inconsistent with the present disclosure, it is superseded for purposes of the present disclosure by the teachings herein set forth, and the present disclosure set forth shall control in the case of such inconsistency.

Standard Kirby-Bauer assays, and the inventor's prior assays just mentioned, require the just-described measurement, and interpretative table look-up, for each antimicrobial agent sample used in the test. This means time and care are required to accurately measure the distance, and to correctly use the table; so that an accurate test result can be obtained with regard to each agent tested. This adds to the time required for completion of the assay, and to the difficulty of performing it.

SUMMARY

The inventor has recognized that making placement of each antimicrobial agent on the growth medium easier, as well as providing a simpler way to obtain accurate results, could reduce the time and difficulty involved in obtaining accurate test results. For example interfitting elements can be employed to facilitate worthwhile improvements to the test methodology described in U.S. Pat. No. 7,262,021. In one example implementation the invention provides an antimicrobial susceptibility assay, including: an assay dish including at least one chamber and at least one wall; at least one growth medium carried by the assay dish; at least one interpretive indication positionable at a predetermined distance from a sample location adjacent a growth medium in the assay dish; at least one antimicrobial agent sample positionable at a sample location; at least one interfitting element, said at least one interfitting element configured to enable at least one of: a) more accurately positioning said at least one antimicrobial sample at a sample position in contact with the growth medium; b) carrying said least one interpretive indication positionable at a predetermined distance from said sample position, said assay enabling the interpretative indication to be compared with a margin of a zone of inhibition of microbial organism growth on said medium to determine an assay result, wherein said result enables determination of at least one of: a) "susceptible;" "intermediate;" and, "resistant."

The inventor has recognized that making placement of each antimicrobial agent on the growth medium easier, as well as providing a simpler way to obtain accurate results, could reduce the time and difficulty involved in obtaining accurate test results. For example interfitting elements can be employed to facilitate worthwhile improvements to the test methodology described in U.S. Pat. No. 7,262,021. In one example implementation the invention provides an antimicrobial susceptibility assay, including: an assay dish including at least a first chamber and a second chamber and at least one wall; at least one growth medium carried by the assay dish; at least one interpretive indication positionable at a predetermined distance from a sample location adjacent a growth medium in the first chamber of the assay dish; at least one antimicrobial agent sample positionable at a sample location; at least one interfitting element, said at least one interfitting element configured to enable at least one of: a) more accurately positioning said at least one antimicrobial sample at a sample position in contact with the growth medium; b) carrying said least one interpretive indication positionable at a predetermined distance from said sample position, said assay enabling the interpretative indication to be compared with a margin of a zone of inhibition of microbial organism growth on said medium to determine an assay result, wherein said result enables the determination of one of: a) "susceptible;" "intermediate;" and, "resistant." The assay can also provide, in the second chamber, for a concurrent isolation and culture enabling additional information regarding the microorganism to be obtained, including a determination that the concentration of microorganisms in the sample placed on the growth medium in the first chamber is within a range wherein an antimicrobial susceptibility assay result carried out in the first chamber will be valid.

These innovations allow for more rapid and accurate placement of antimicrobial samples into susceptibility test chambers; and facilitate accurate direct testing results—such as the recognized categories of "resistant," "intermediate," or "susceptible"—to be more quickly and easily obtained at the end of the incubation period (generally 12 to 18 hours). Thus, improvements in ease of conducting the testing and the benefit of less time being required to obtain accurate results are facilitated.

BRIEF DESCRIPTION OF THE SEVERAL VIEWS OF THE DRAWINGS AND STRUCTURE REFERENCED THEREIN

Further features and advantages of the invention will be appreciated with reference to example implementations described below in more detail, as shown in the accompanying drawing figures, (wherein like reference numbers refer to like—but not necessarily identical—elements); which drawing figures and descriptions are given by way of illustrative example, and not by way of limitation of the scope of the invention; and wherein as to said drawing figures:

FIG. 1B is a top photographic view in each case of a dish of an example kit and a swab carrying an organism sample, shown at two different moments in time, which together illustrate a method of applying a bacterial sample to two chambers of the dish for antimicrobial susceptibility testing;

FIG. 1C is a schematic top view of two chambers of a dish of a test kit, and sample spreading on growth media therein, which illustrates an example embodiment of the kit showing a method of applying an organism sample for colony isolation in concurrent testing facilitating presumptive identification or identification to the species level;

FIG. 1D is a schematic top view of two chambers of a dish in an example embodiment of the kit, illustrating applying antimicrobial disk-quarters to growth media at sample locations in the chambers using a push pin;

FIG. 1E is an illustrative representation, partly photographic, partly by way of line drawing, which illustrates an example embodiment in a set-up-and-incubated kit dish showing zones of inhibition as well as isolated colonies, as well as a micrometer usable to measure a radius of a zone of inhibition;

FIG. 1F is an data table facilitating test results, and illustrates a Zone Radius Interpretive Standards table showing results from the example of FIG. 1E in one example;

Figure 1A:
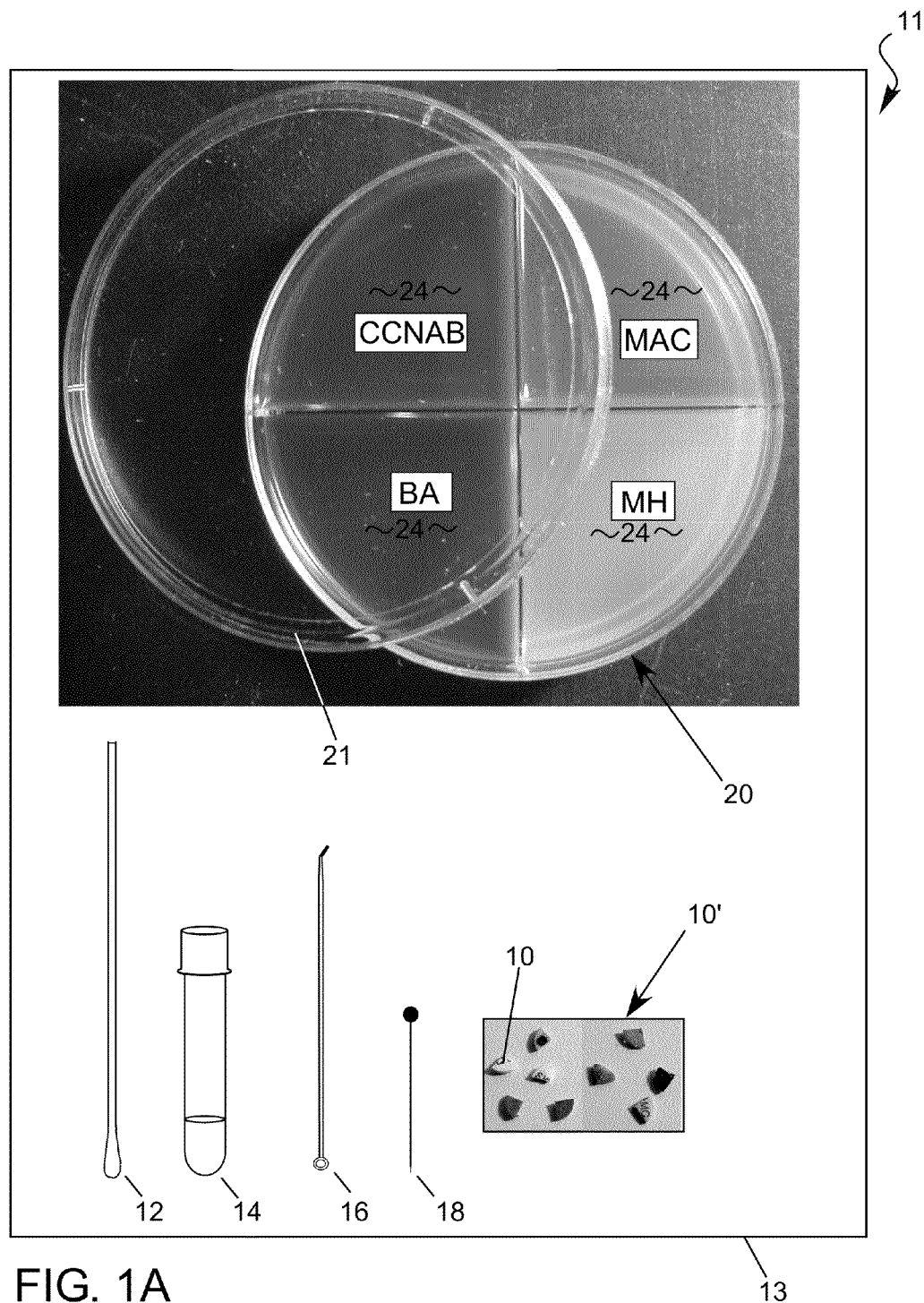
FIG. 1A is an illustrative representation, partly photographic, partly by way of line drawing, which illustrates an example embodiment of the invention in a kit of containing components useable in performing a direct antimicrobial susceptibility test and concurrent testing facilitating presumptive identification of a predominating organism under test.
Figure 2D:
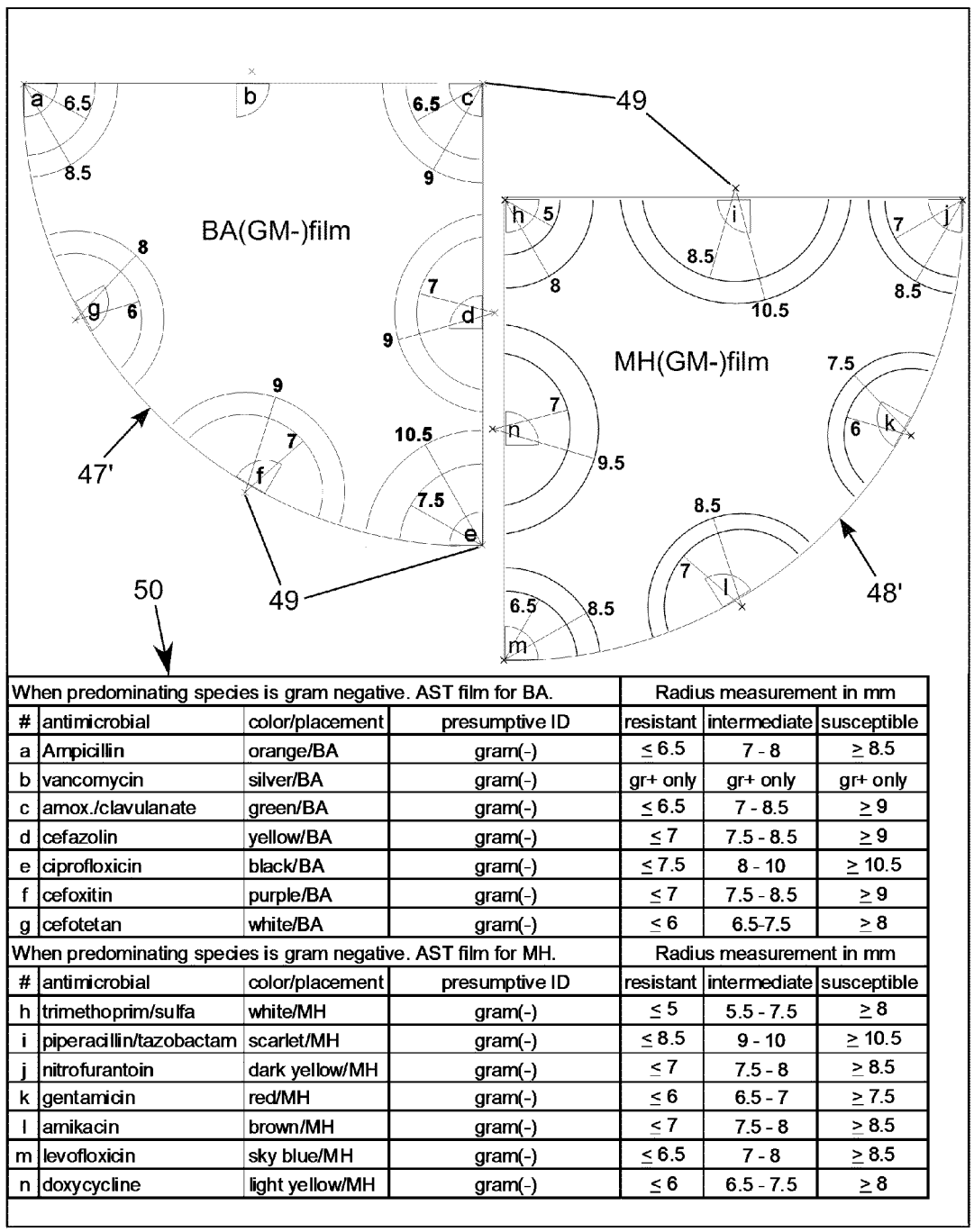
FIG. 2A is a top view of four interfitting elements, in this example embodiment consisting of translucent elements with examples of interpretive indications as disclosed and taught herein carried therein, wherein two of said interfitting elements (47' and 48') are specific for gram-negative bacteria (GM−)

FIG. 2B is a top photographic view of a portion of an example embodiment dish shown in FIG. 1E and illustrates a hypothetical result if gram-negative interfitting elements were to be placed into the chambers of the setup-and-incubated dish shown in FIG. 1E at the same scale, as well as the desirability of having the sample locations be coordinated with the interpretative indications, by way of examples of differences in sample locations assumed with the interpretative indications and actual sample locations 41, and the desirability of accurate registration of assumed and actual locations so as to coordinate said indications with the actual sample locations used in order to obtain results directly by visual comparison of the interpretive indications and the margins of the zones of inhibition;

FIG. 2C is a table which shows a comparison between the results of the example testing of FIGS. 1E and 1F and hypothetical results obtained using representations of the interfitting elements comprising overlays with interpretive indications at the same scale in FIG. 2B, showing results to be effectively identical;

FIG. 2D is a top view of two interfitting elements carrying interpretive indications, in the illustrated example being specific for gram-negative bacteria with indicated growth media types shown thereon, said elements being shown for convenient comparison in the same figure with a data table including data comprising specific millimeter standard values from FIG. 1F, used for interpretation to obtain results of "resistant", intermediate", or "susceptible;"

Figure 2F:
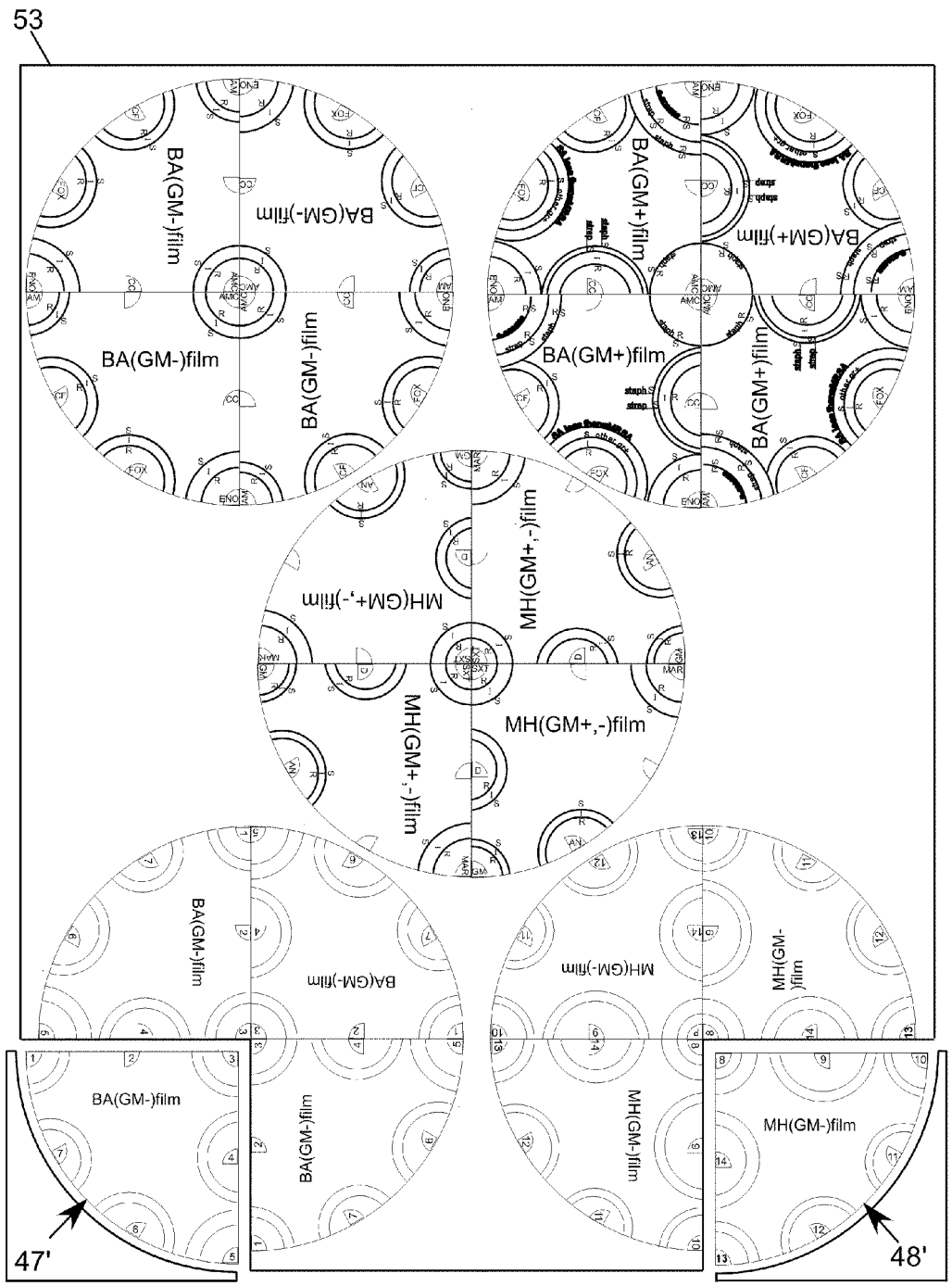
Figure 3E:
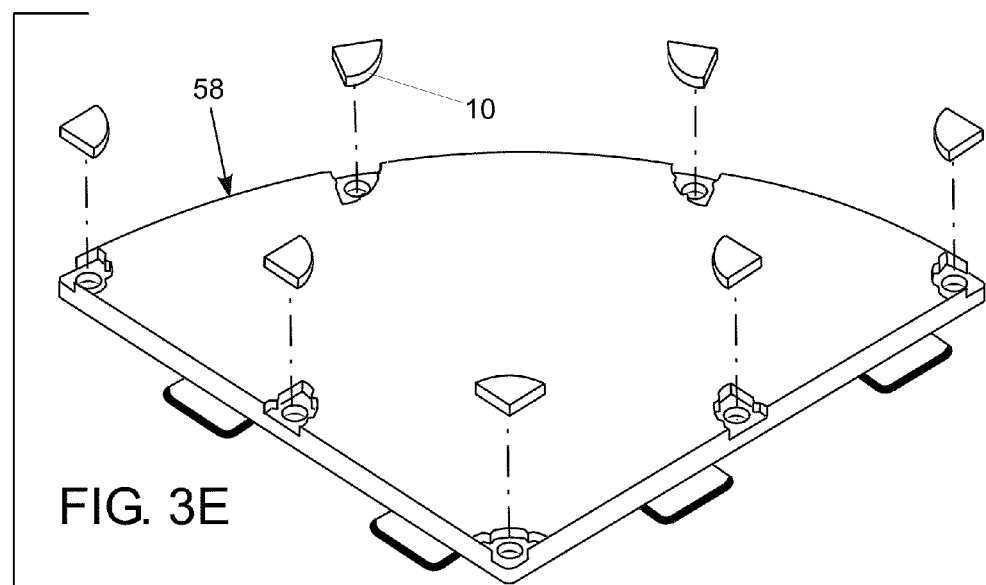
Figure 3F:
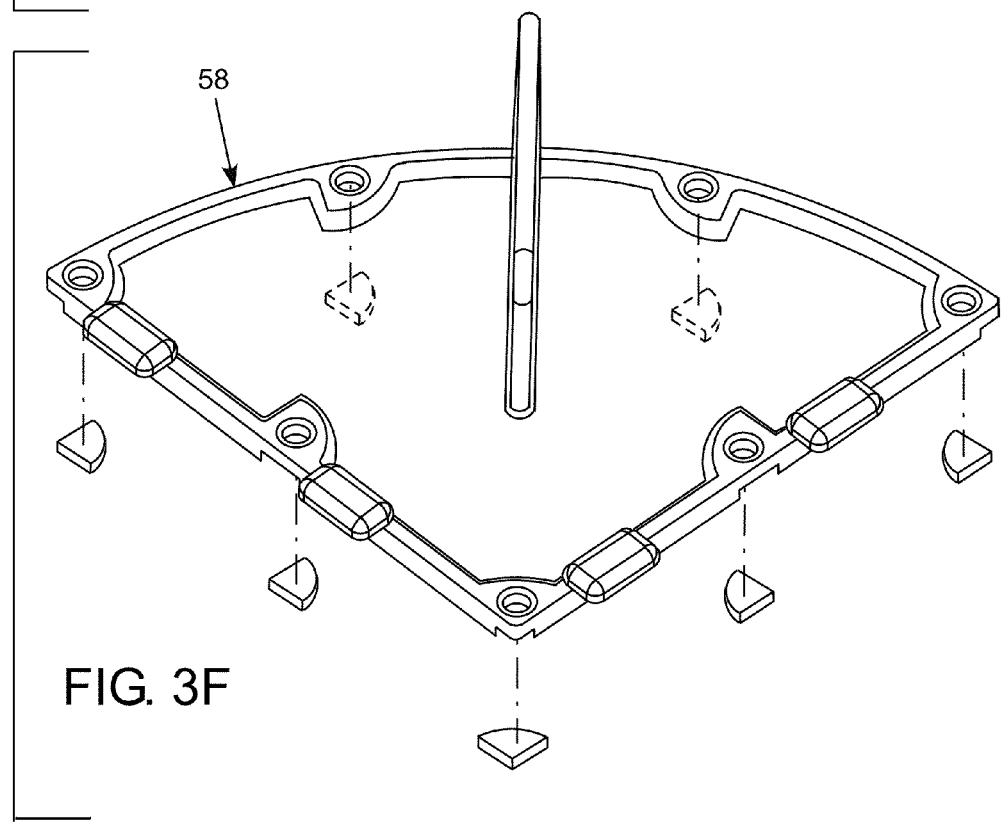
Figure 3G:
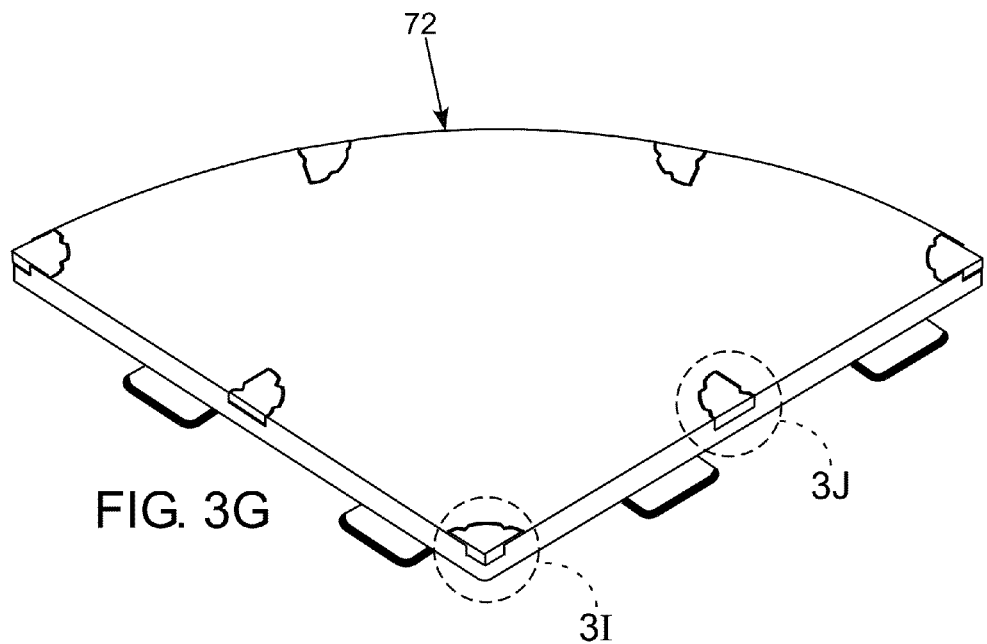
Figure 3H:
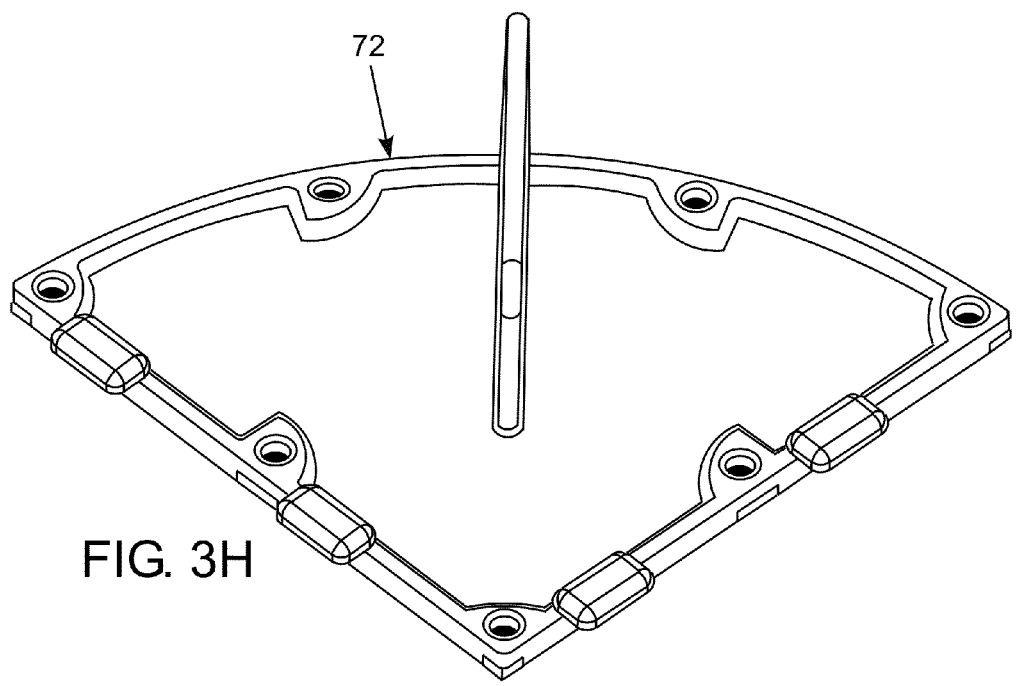
Figure 3I:
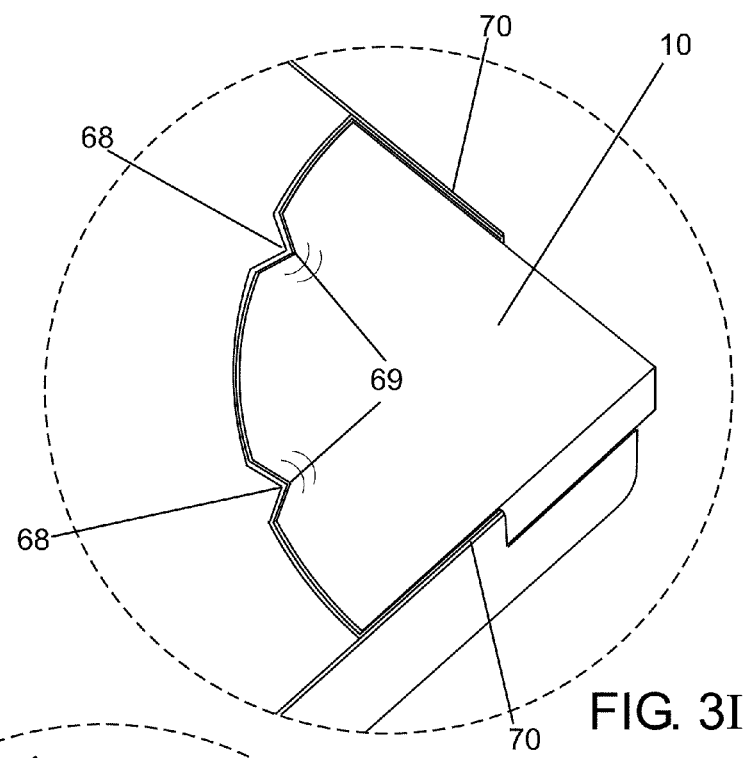
Figure 3J:
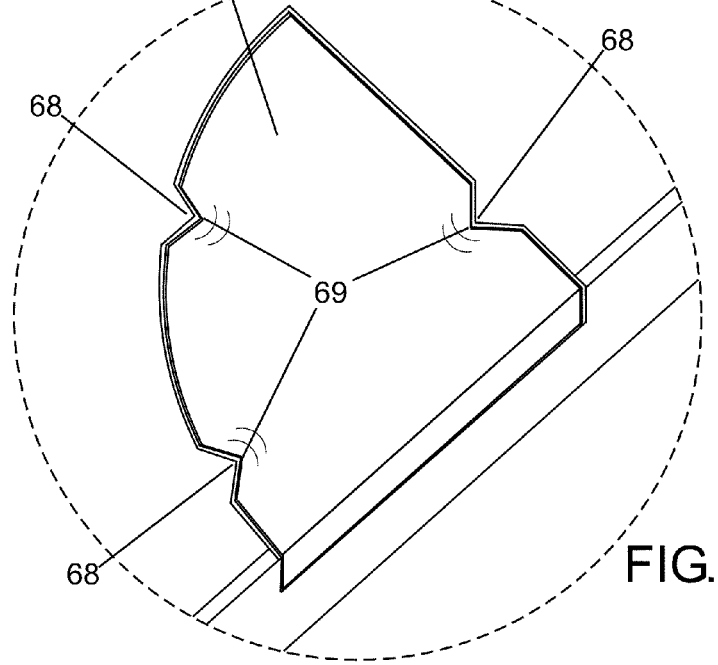
Figure 4A:
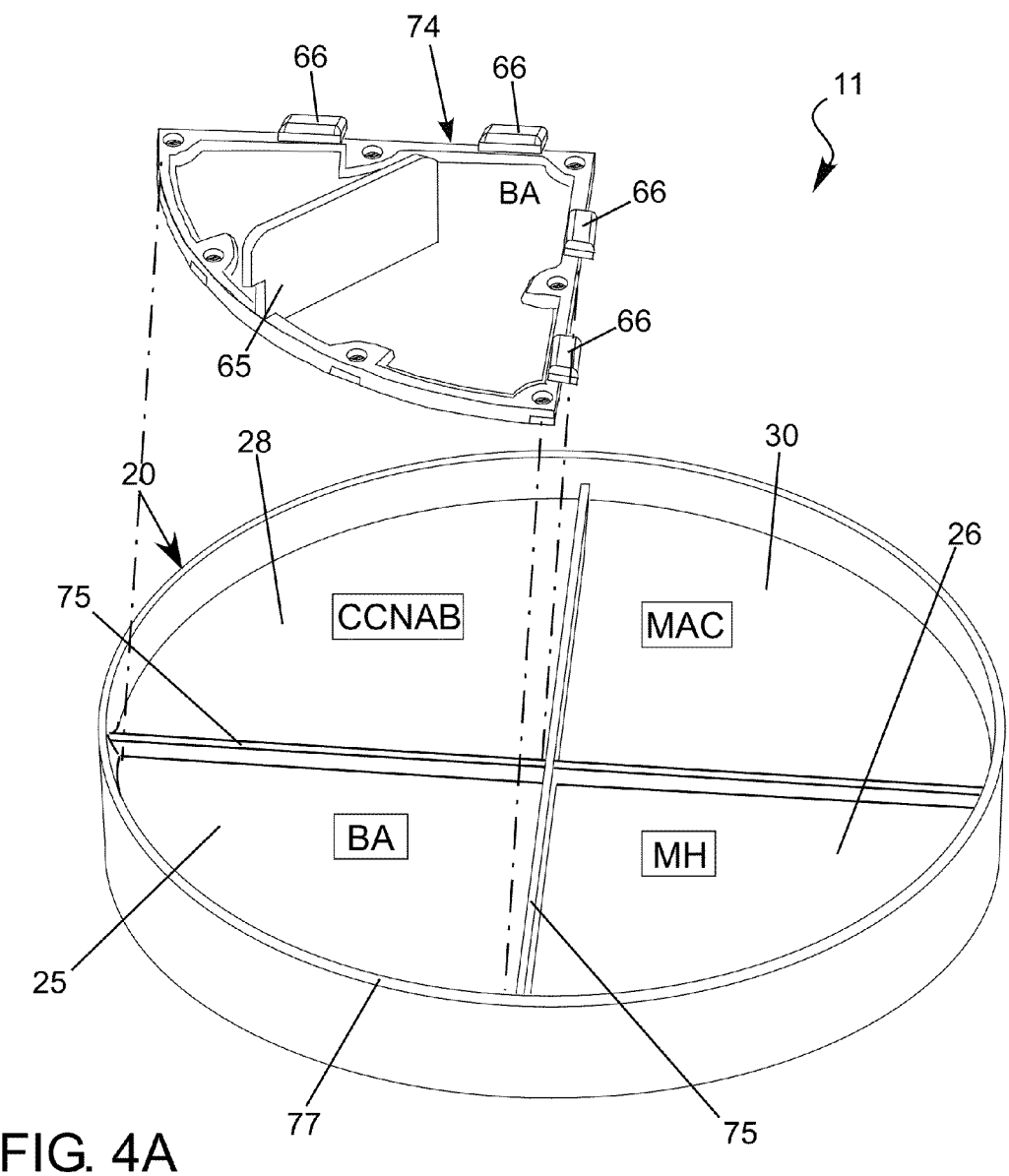

FIG. 2E is a schematic top view of a portion of a dish with interfitting elements comprising overlays carrying interpretive indications interfitted therewith, and illustrates interfitting elements with interpretive indications (showing standard value measurements from an interpretive standards table) for gram-positive species antimicrobial susceptibility testing, shown for convenient comparison in the same figure with a data table including data as set forth in the above-mentioned interpretive standards table;

FIG. 2F is a top view, partially in break-away, of example printed interfitting elements (with interpretive indications) to be cut out, and as cut out in the bottom left and right corners of the figure;

FIG. 3A is a bottom perspective view of an interfitting element in another example embodiment, as illustrated in this figure being an example embodiment in an antimicrobial-disk-quarter applicator configured for applying anti-microbial agent samples in the form of quarter disk segments, said segments comprising quartered standard Kirby-Bauer disks, the sample disk quarters not being shown to more clearly show details of the applicator;

FIG. 3B is a top perspective view of the interfitting element antimicrobial-disk-quarter applicator shown in FIG. 3A;

FIG. 3C is a more detailed view, taken about line 3C in FIG. 3A, of a portion of the interfitting element shown in FIG. 3A, which illustrates a corner-cavity-disk-quarter-holder portion of said element;

FIG. 3D is a more detailed view, taken about line 3D in FIG. 3A, of a portion of the interfitting element shown in FIG. 3A, which illustrates an edge-cavity-disk-quarter-holder portion of said element;

FIG. 3E is an exploded bottom perspective view of the interfitting element antimicrobial-disk-quarter applicator shown in FIG. 3A, with antimicrobial agent samples, in the form of disk-quarters, ready for insertion into the applicator, and/or for subsequent application off the applicator onto a growth medium (not shown in the figure);

FIG. 3F is an exploded top perspective view of the interfitting element and antimicrobial agent samples shown in FIG. 3E;

FIG. 3G is a bottom perspective view of the interfitting element antimicrobial disk-quarter applicator of FIG. 3A with antimicrobial agent sample disk-quarters inserted;

FIG. 3H is a top perspective view of the interfitting element antimicrobial disk-quarter applicator of FIG. 3G, with said disk-quarters inserted;

FIG. 3I is a more detailed view, taken about line 3I in FIG. 3G, of a portion of the interfitting element shown in FIG. 3G, which illustrates a corner-cavity-disk-quarter-holder portion of said element with an antimicrobial agent sample disk quarter held therein;

FIG. 3J is a more detailed view, taken about line 3J in FIG. 3G, of a portion of the interfitting element shown in FIG. 3G, which illustrates an edge-cavity-disk-quarter-holder portion of said element with an antimicrobial agent sample disk quarter held therein;

FIG. 4A is a top front exploded perspective view of an example embodiment dish and interfitting element configured as an antimicrobial-disk-quarter applicator for a chamber of the dish containing BA agar growth medium, illustrating how said applicator can be interfitted with said dish.

Figure 4D:
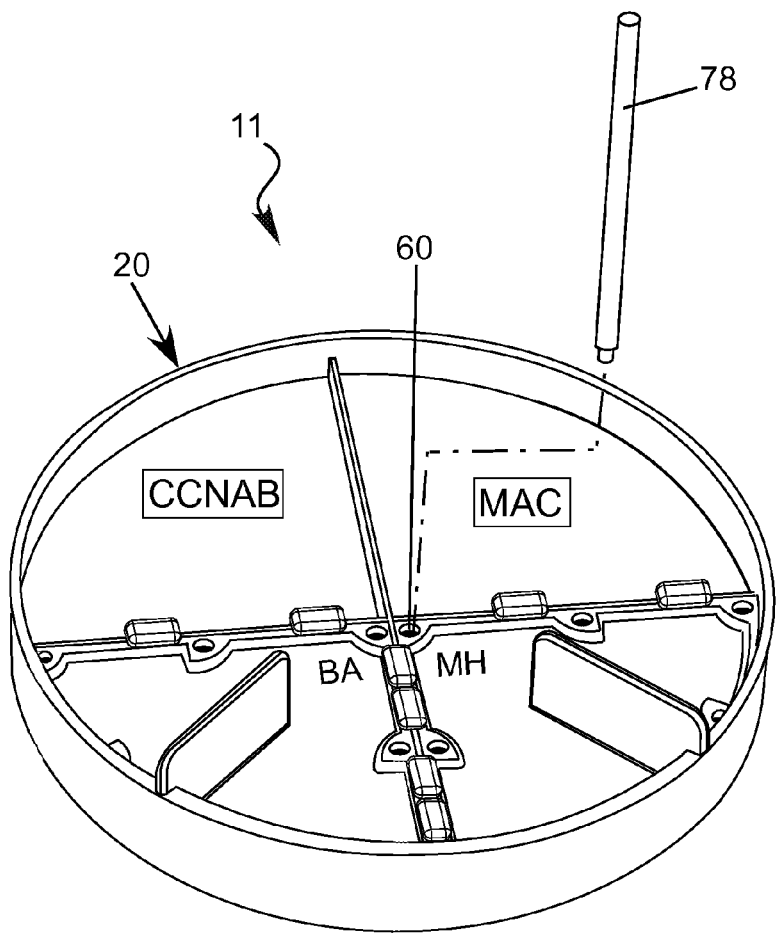
Figure 4E:
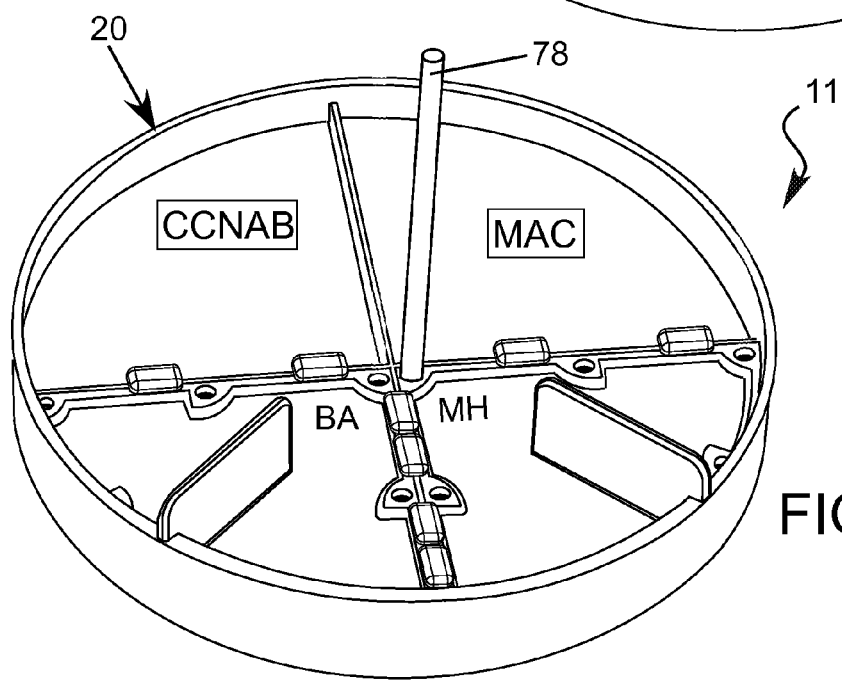
Figure 5A:
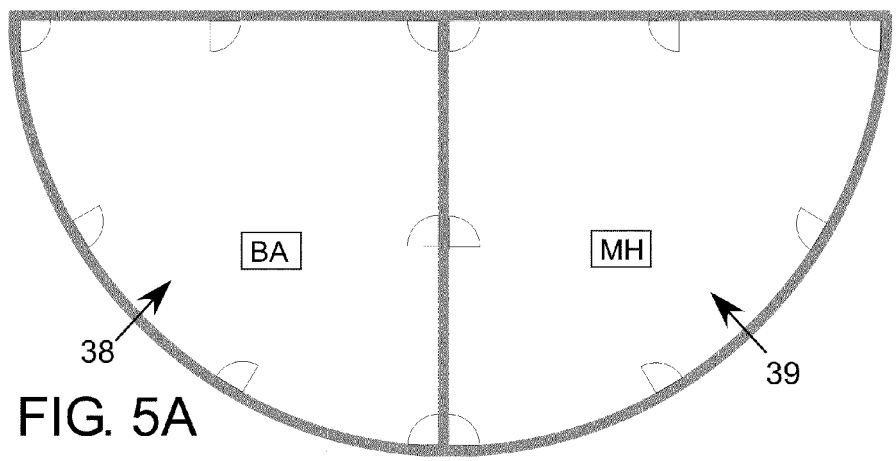
Figure 5B:
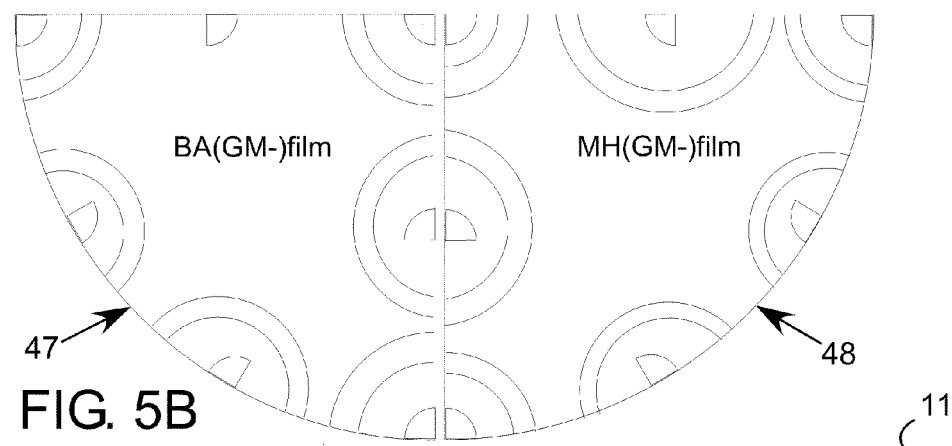
Figure 5C:
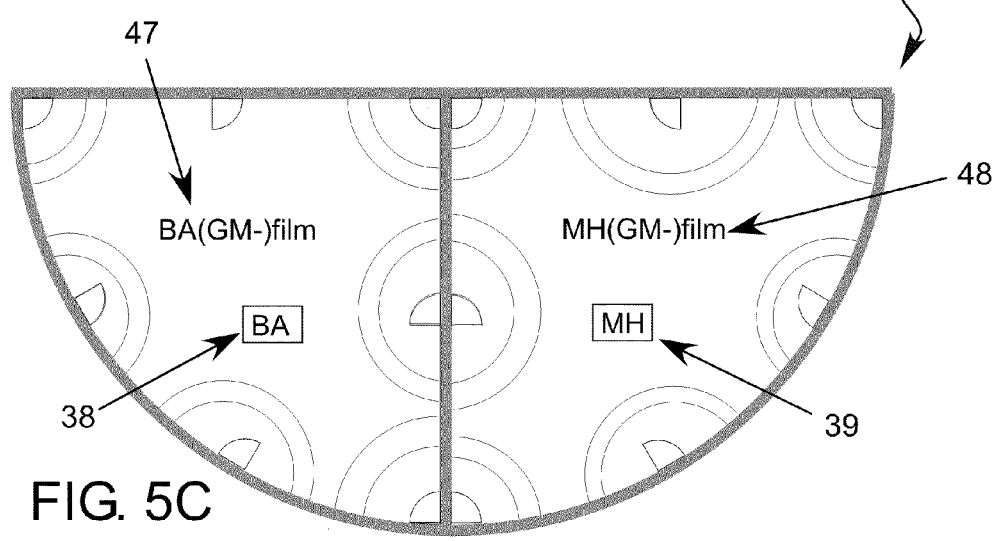
Figure 6A:
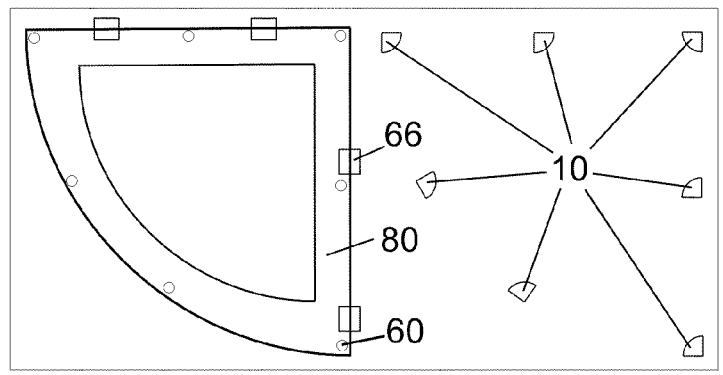
Figure 6B:
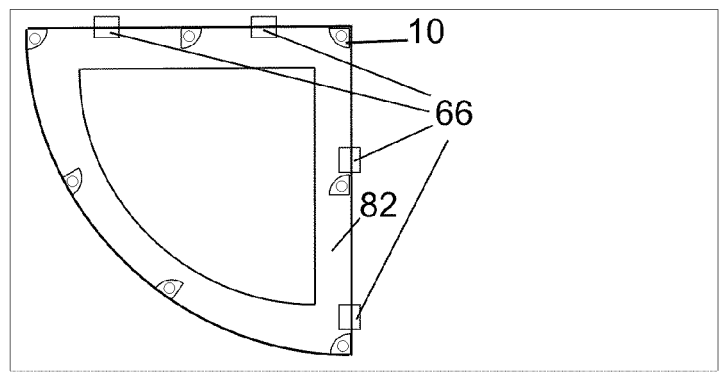
Figure 6C:
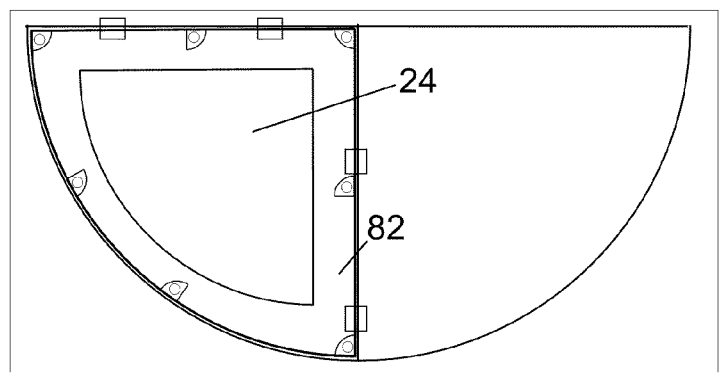
Figure 6D:
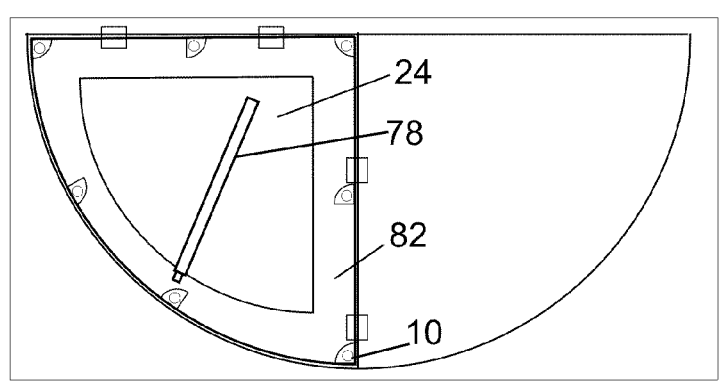
Figure 6E:
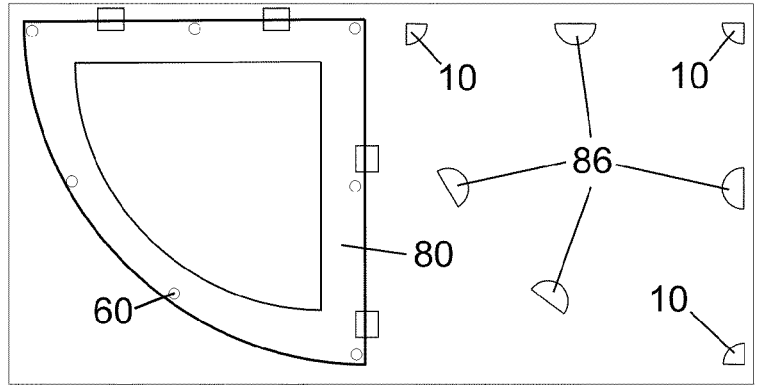
Figure 6F:
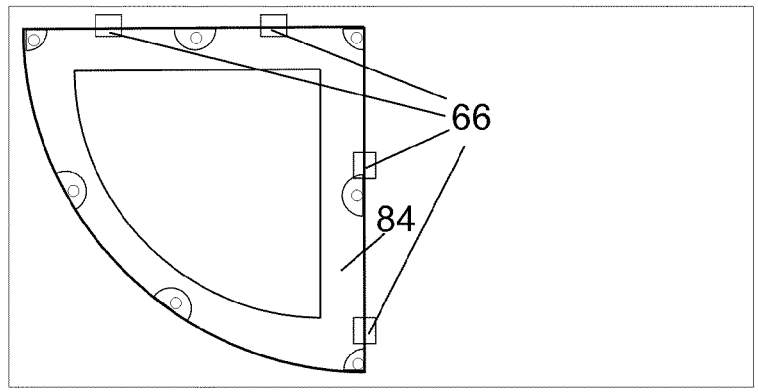
Figure 6G:
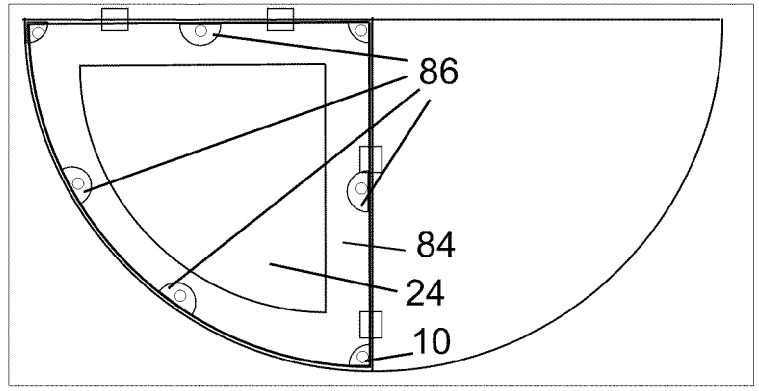
Figure 6H:
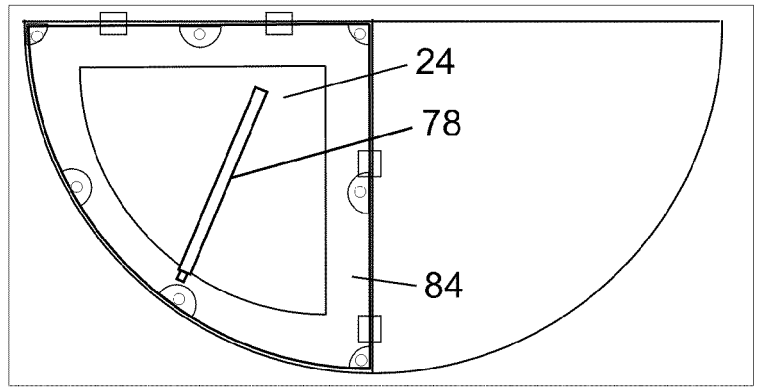

FIG. 4B is a top front exploded perspective view of an example embodiment dish of FIG. 4A and interfitting elements configured as an antimicrobial-disk-quarter applicators interfitting with the dish over two chambers of the dish containing BA agar growth medium (shown fitted), and MH agar growth medium, respectively, illustrating how the latter-mentioned MH agar chamber applicator of the two applicators can be interfitted with said dish and previously interfitted BA agar chamber interfitting element antimicrobial agent sample applicator;

FIG. 4C is a top front perspective view of the example embodiment dish and said applicators of FIGS. 3A through 4B, with said applicators in place for placing antimicrobial agent sample disk segments at sample locations in two chambers of said dish where antimicrobial agent susceptibility testing is to occur;

FIG. 4D is a top front perspective view of the dish and interfitting elements of FIG. 4C and an anti microbial agent sample disk segment release tool, which illustrates the kit plate (dish) ready for antimicrobial disk-quarter release and placement on the growth media using said release tool, and showing the release tool ready to be so used;

FIG. 4E is a top front perspective view of the dish, interfitting elements and tool of FIG. 4D, which illustrates a method of antimicrobial disk-quarter release by operation of release tool;

FIG. 5A is a top view of a portion of the dish of FIG. 4A showing BA and MH growth media chambers, and showing released and placed antimicrobial agent sample disk-quarters on the agar after the applicator interfitting elements have been removed;

FIG. 5B is a top view of interfitting elements which illustrates BA and MH gram-negative interfitting elements with interpretive indications configured to interfit with the portion of the dish shown in FIG. 5A;

FIG. 5C is a top view of the portion of the dish shown in FIG. 5A with the interfitting elements of FIG. 5B interfit therewith, which illustrates the accurate match of interfitting element carried interpretative indications directly correlating with and spatially matching (registering with) the previously inserted and placed antimicrobial agent sample disk-quarters;

FIG. 6A is a top view of an interfitting element and antimicrobial agent sample disk segments which can be provided in an assay kit in another example embodiment, shown prior to attachment of said segments to the interfitting element, which in this embodiment of an interfitting element a releasable adhesive (such as a pressure sensitive adhesive) is used for attachment of antimicrobial disk-quarter segments to said interfitting element;

FIG. 6B is a top view of the interfitting element with a releasable adhesive of FIG. 6A with samples loaded;

FIG. 6C is a top view of a portion of a dish with the interfitting element of FIG. 6B interfitted, and illustrates a disk-quarter loaded interfitting element with a releasable adhesive inserted into a susceptibility test chamber of the dish;

FIG. 6D is a top view of the portion of a dish shown in FIG. 6C and a release tool about to be used, and illustrates a method of removing disk-quarters from interfitting element with a releasable adhesive so as to accurately place them on agar in said test chamber underneath the interfitting element applicator;

FIG. 6E is a top view of an interfitting element and antimicrobial agent sample disk segments which can be provided in an assay kit in another example embodiment, shown prior to attachment of said segments to the interfitting element, which in this embodiment of an interfitting element a releasable adhesive is used for attachment of antimicrobial disk-quarter segments to said interfitting element using disk quarters and disk halves as antimicrobial agent samples;

FIG. 6F is a top view of the interfitting element with releasable adhesive of FIG. 6E with samples loaded;

FIG. 6G is a top view of a portion of a dish with the interfitting element of FIG. 6F interfitted, and illustrates a disk-quarter/disk-half loaded interfitting element with releasable adhesive inserted into a susceptibility test chamber of the dish;

FIG. 6H is a top view of the portion of a dish shown in FIG. 6G and a release tool about to be used, and illustrates a method of removing disk-quarters/disk-halves from the interfitting element with releasable adhesive so as to accurately place them on agar in said test chamber underneath the interfitting element applicator;

FIG. 7A is a top view of antimicrobial agent samples, and for convenience, corresponding area data in square millimeters, and illustrates a standardized 6 mm diameter Kirby Bauer paper disk with an antimicrobial agent sample paper of different shape but equal area;

FIG. 7B is similar to FIG. 7A, but illustrates a Kirby Bauer half disk with a paper of equal area;

FIG. 7C is similar to FIG. 7A, but illustrates a Kirby Bauer quarter disk with a paper of equal area;

FIG. 7D is a top view of an interfitting element (translucent) with interpretive indications in another example embodiment, in this case being an applicator that places the antimicrobial samples into chambers, stays in place through the incubation, and also carries the interpretive indications which can be used to directly determine test results, e.g. susceptible, intermediate or resistant determinations for each sample using the correlated interpretive indications;

FIG. 7E is a top view of a loaded interfitting element of FIG. 7D with antimicrobial agent sample quarter disks attached via a releasable adhesive;

FIG. 7F is a top view of a loaded interfitting element of FIG. 7D with mix of half and quarter disk antimicrobial agent samples.

Figure 8A:
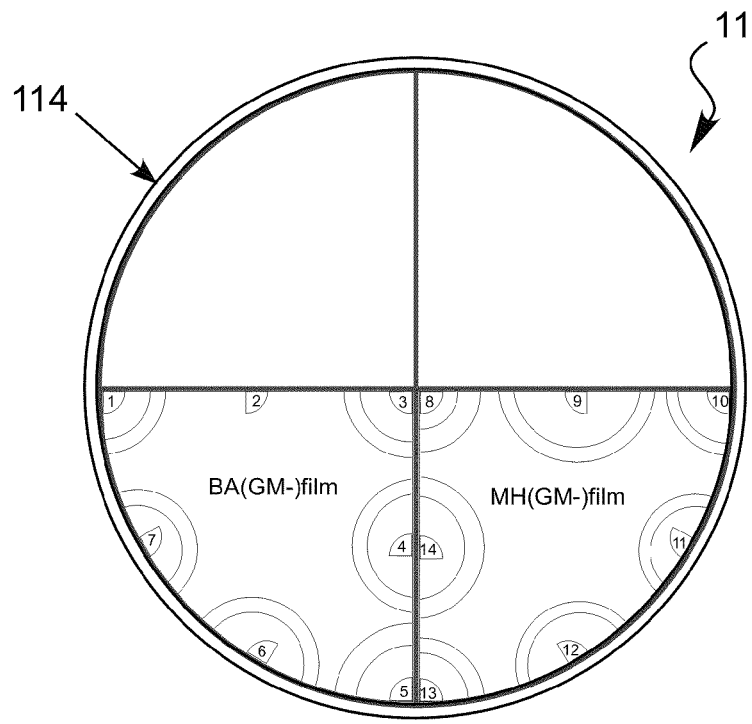
Figure 8B:
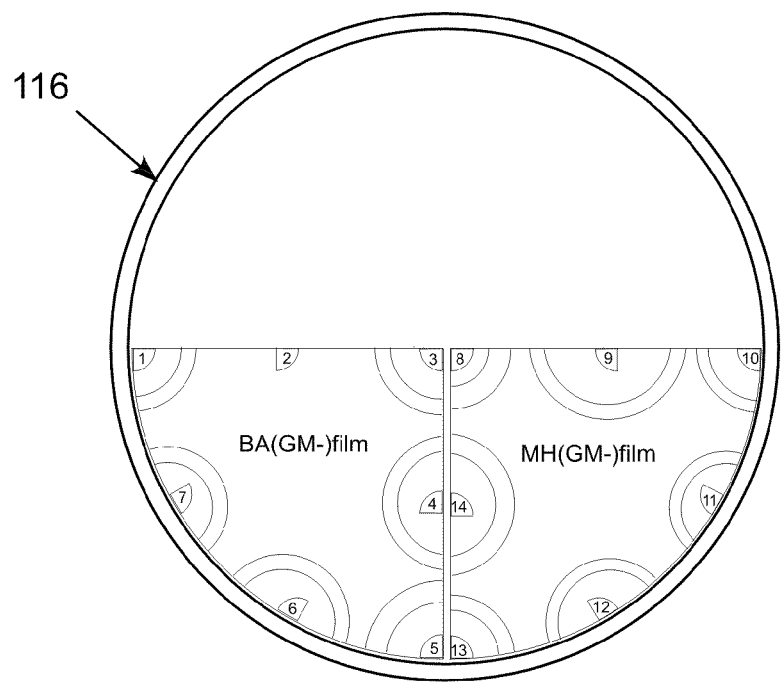
Figure 9A:
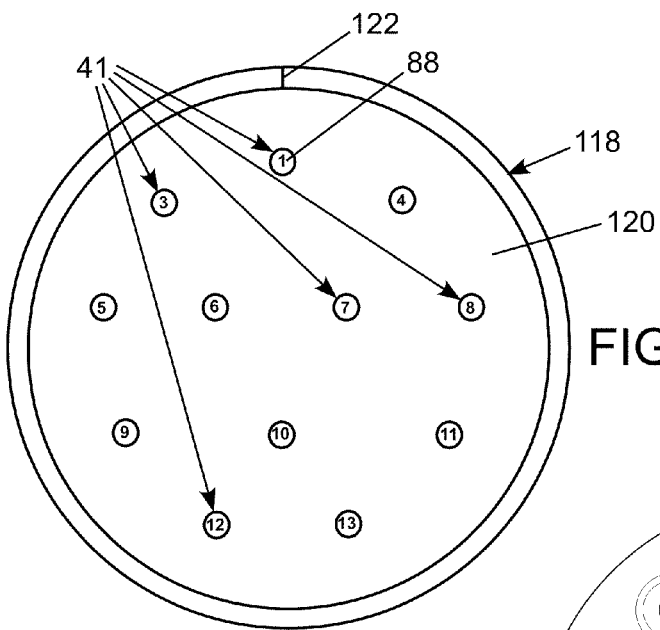
Figure 9B:
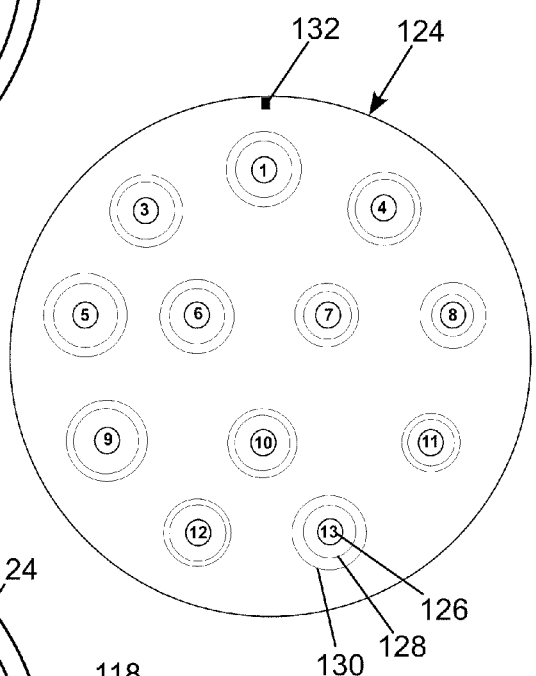
Figure 9C:
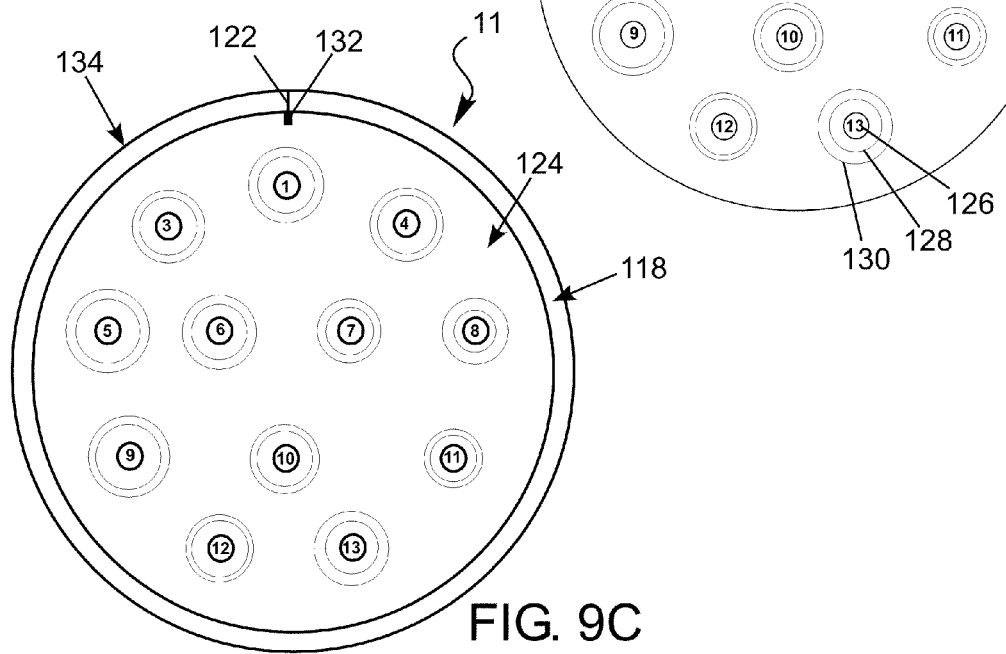

FIG. 7G is a schematical crossectional view of two cutaway portions of a dish chamber containing an agar growth media, for convenient comparison of the two portions, showing an effect of dish chamber wall surface treatment or coating, for example a wall coating including a hydrophobic agent;

FIG. 8A is a top view of a dish in one example embodiment, which illustrates an example embodiment having interpretive indications carried by the dish bottom;

FIG. 8B is a top view of an interfitting element, in this example a lid which cooperates with the dish of FIG. 8A to provide interpretive indications and mitigate parallax, said indications being carried by said dish lid as well as said dish;

FIG. 9A is a top view of an example embodiment making use of a standardized Kirby Bauer test methodology in a dish loaded with antimicrobial agent samples dispensed onto sample locations 41 from a conventional dispenser (not shown);

FIG. 9B is a top view of an example embodiment translucent interfitting element with interpretive indications in an embodiment which is coordinated with and can be used with the Kirby Bauer assay set up shown in FIG. 9A; and, FIG. 9C is a top view of the dish of FIG. 9A which illustrates use of the interfitting element of FIG. 9B with interpretive indications to obtain direct result indications in an embodiment with said Kirby Bauer assay methodology, said interfitting element shown inserted into said standard Kirby Bauer set-up dish for enabling a determination of susceptible, intermediate or resistant results determinations in each case.

Figure 10A:
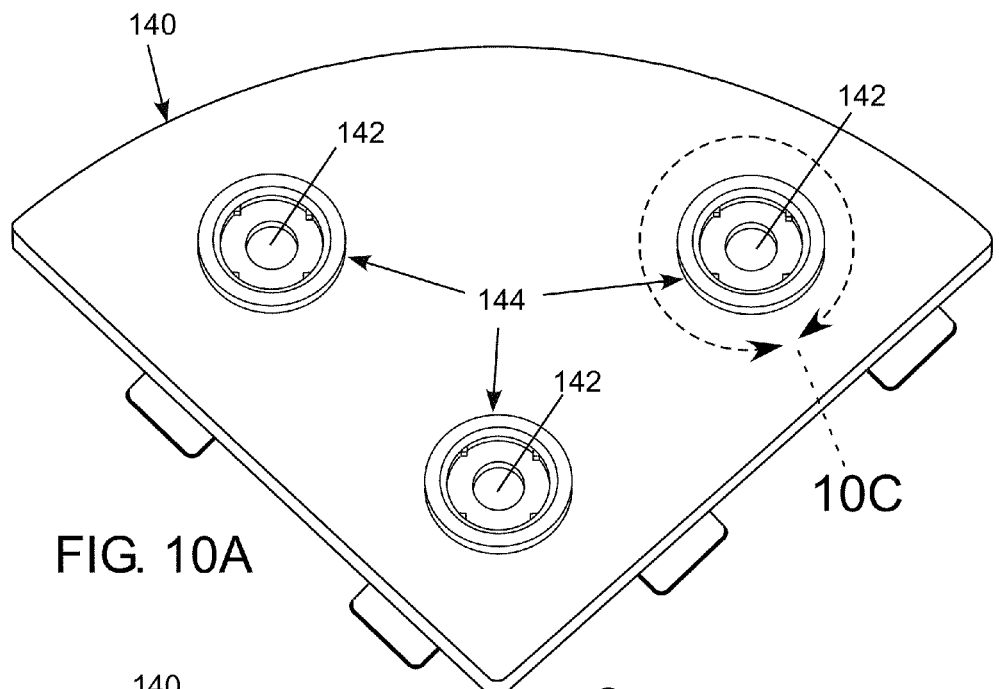
Figure 10B:
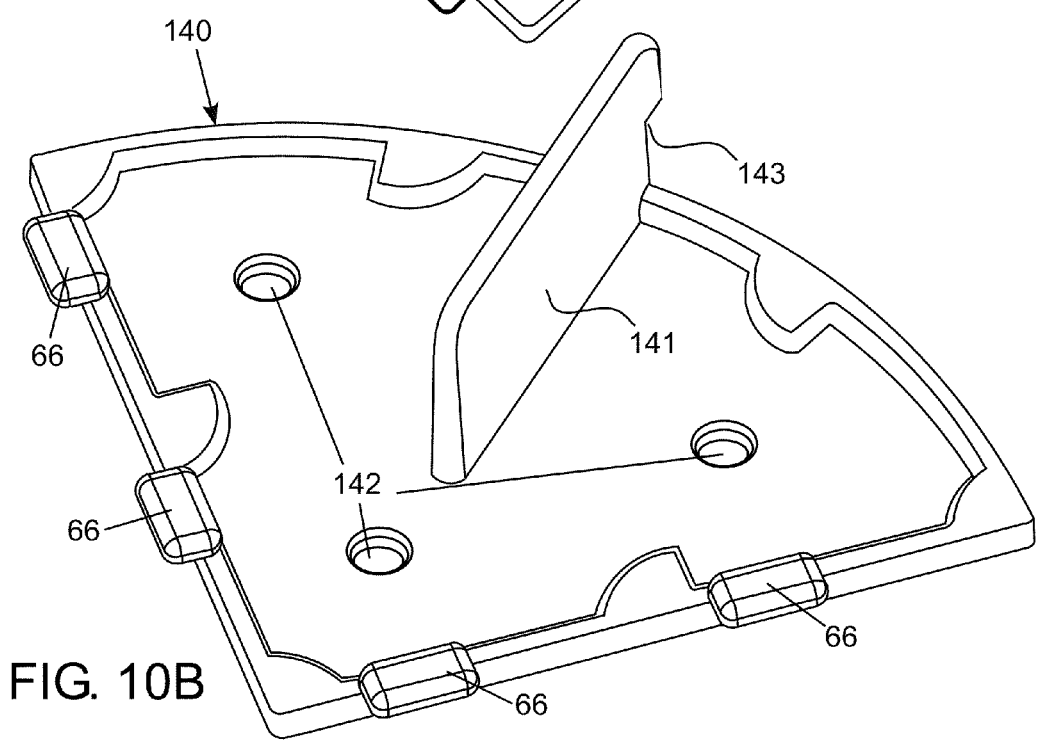
Figure 10F:
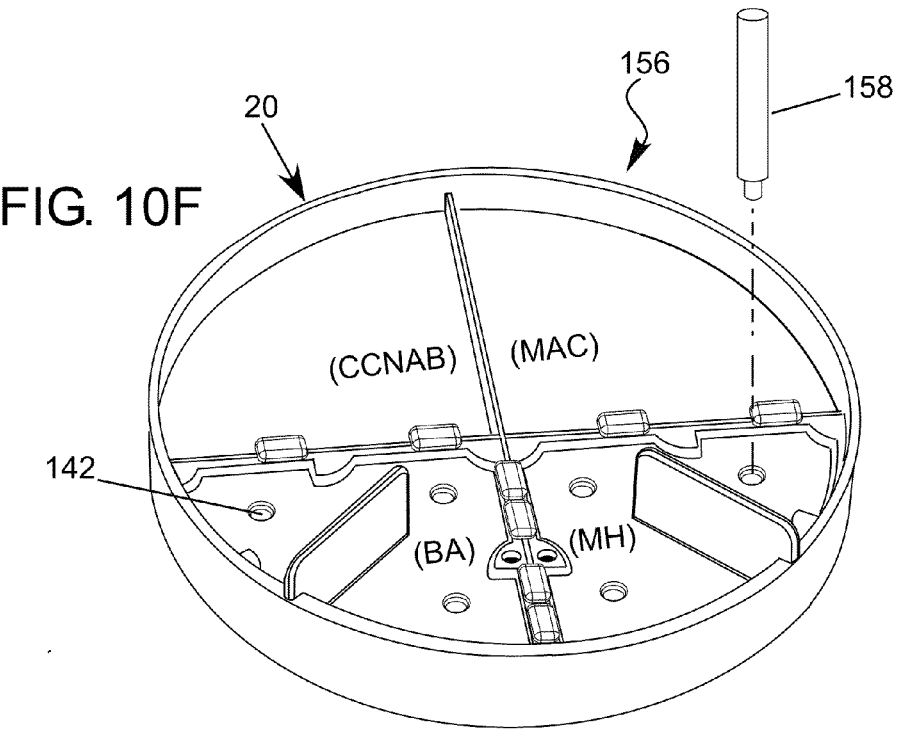
Figure 10G:
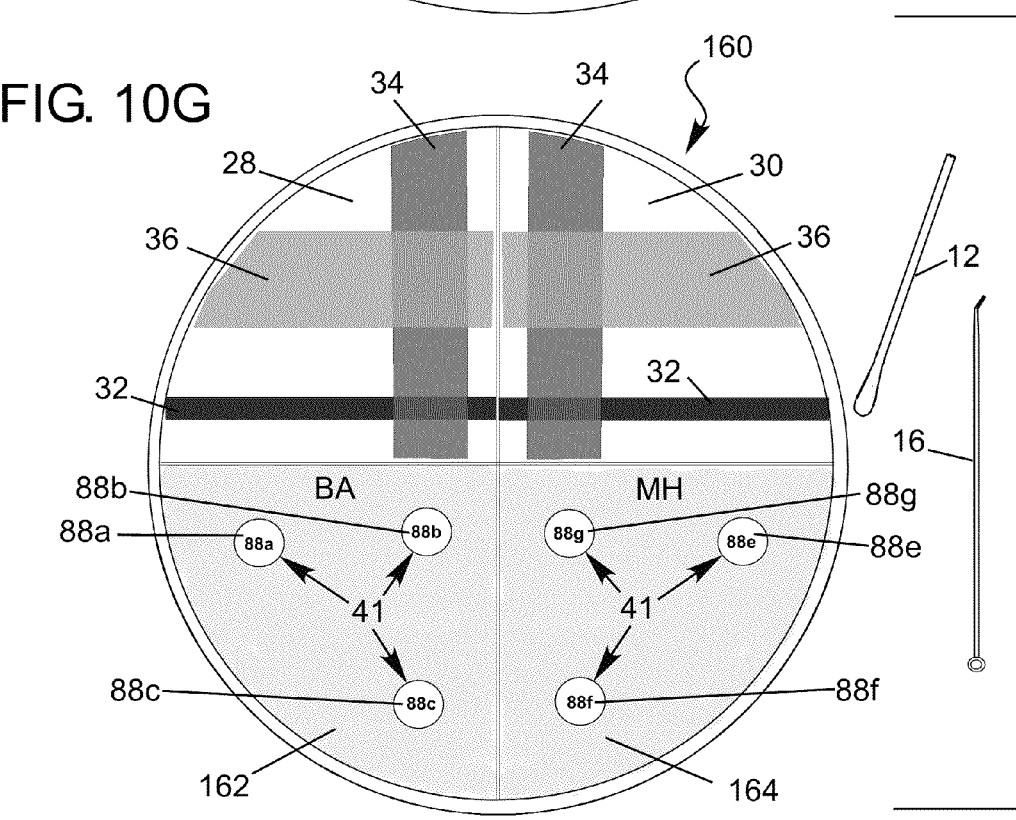
Figure 10H:
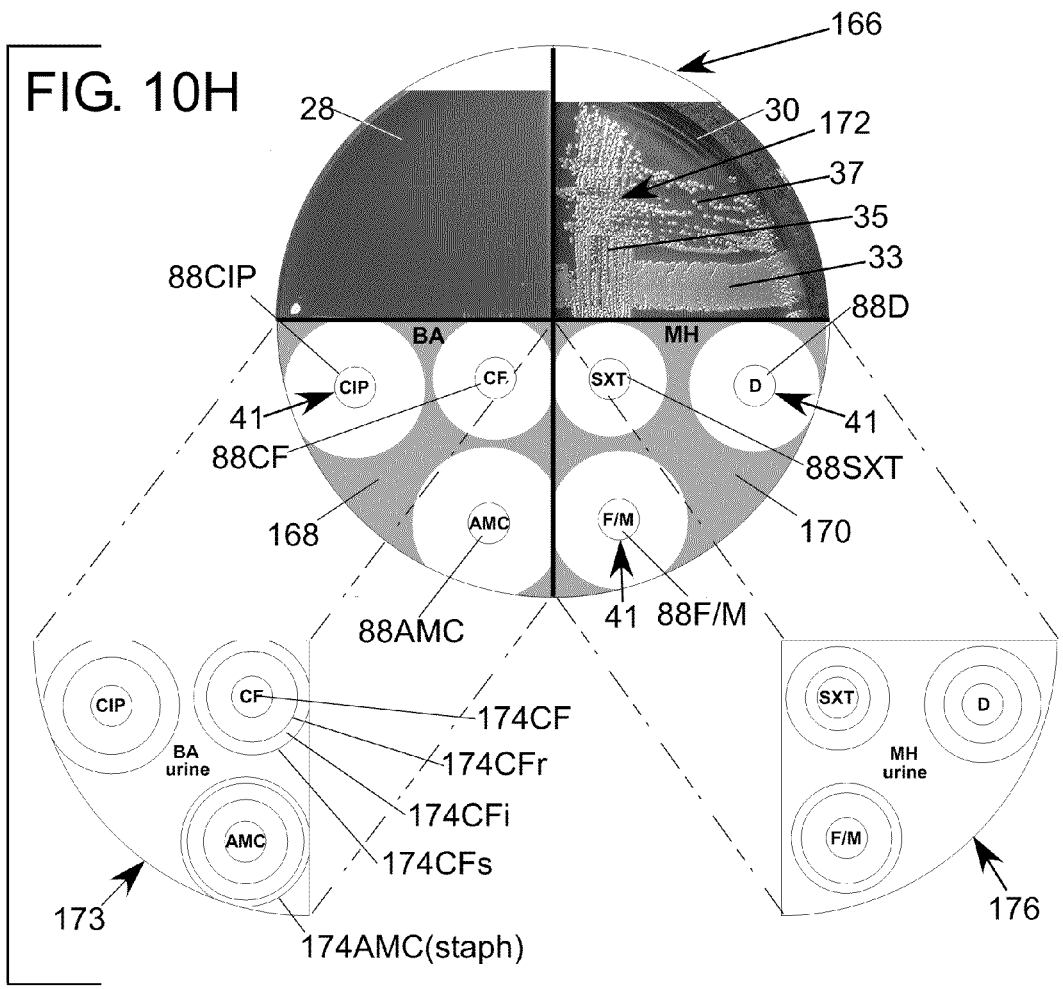
Figure 10I:
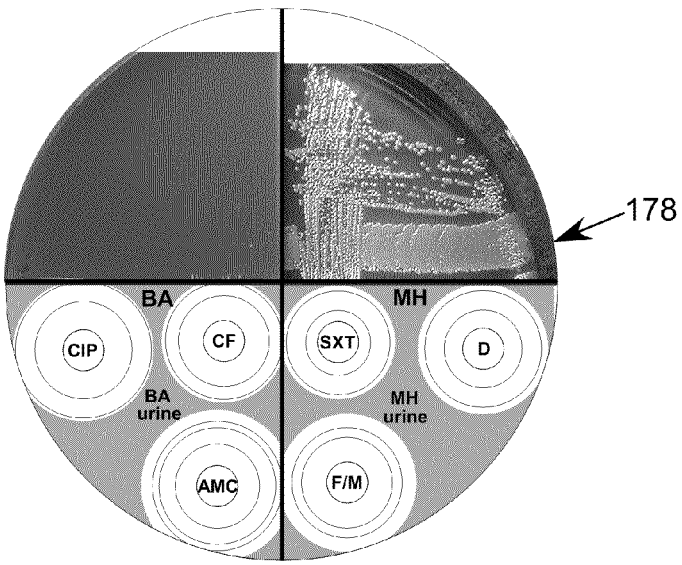
Figure 10J:
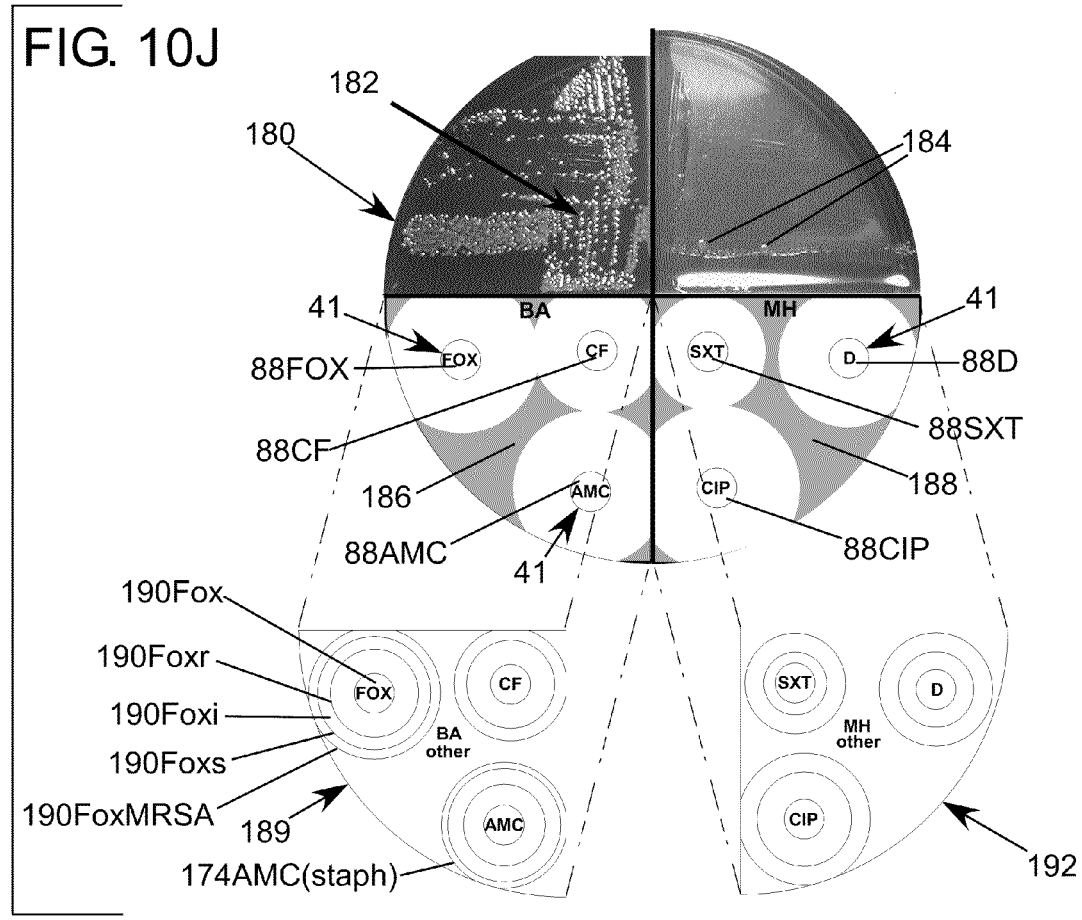
Figure 10K:
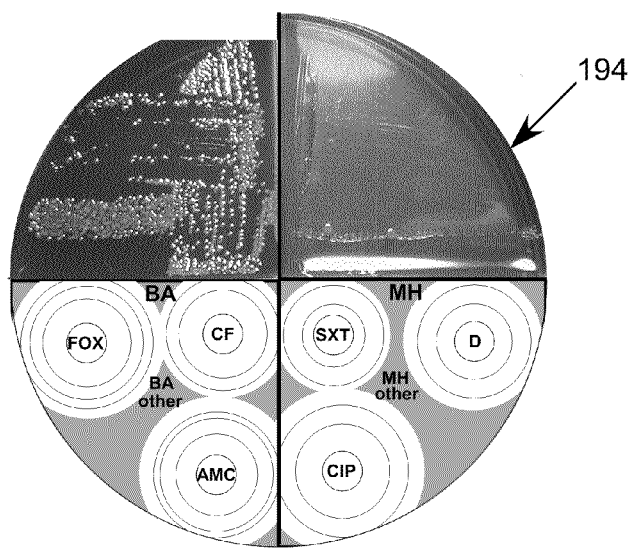
Figure 11:
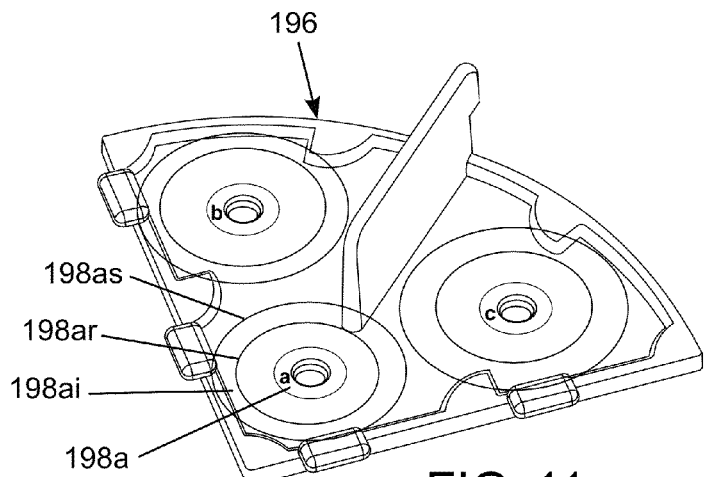
Figure 12:
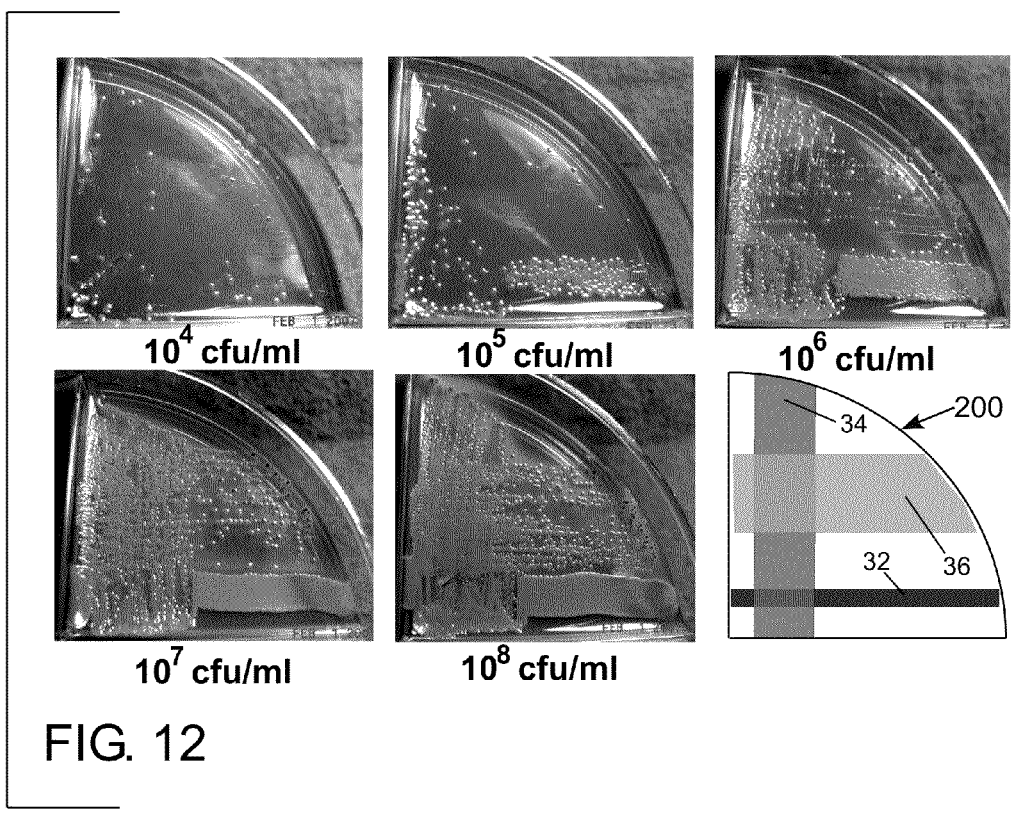

FIG. 10A is a bottom view of an interfitting element, in this example an embodiment for whole disk application;

FIG. 10B is a top view of an interfitting element, in this example an embodiment for whole disk application;

FIG. 10C is a more detailed perspective view, taken about line 10C in FIG. 10A, of a portion of the interfitting element shown in FIG. 10A, which illustrates a whole disk applicator boss portion of said element;

FIG. 10D is an exploded bottom perspective view of the whole disk applicator boss portion shown in FIG. 10C, with antimicrobial agent sample in the form of whole Kirby-Bauer standardized disk, ready for insertion into the boss, and/or for subsequent application off the applicator onto a growth medium (not shown in the figure);

FIG. 10E is a bottom perspective view of the whole disk applicator boss portion of the whole disk applicator interfitting element of FIG. 10A with an antimicrobial agent sample whole disk inserted;

FIG. 10F is a top front partially exploded perspective view of an assay dish and interfitting elements such as that shown in FIG. 10B interfitted, and an anti microbial agent sample disk release tool, which illustrates the kit plate (assay dish) ready for antimicrobial disk release and placement on the growth media using said release tool, and showing the release tool ready to be so used;

FIG. 10G is a top view of an assay dish as shown in FIG. 10F with the interfitting elements removed, showing BA and MH growth media chambers with a microbial sample applied, and showing released and placed antimicrobial agent sample disks on the agar at sample locations 41 as positioned using the applicator interfitting element and release tool. Also shown is the isolation performed in the other two chambers illustrating the isolation scheme for isolating organisms of the added microbial sample as performed on the Columbia CNA agar with blood (CCNAB) isolation/identification chamber and MacConkey agar (MAC) isolation/identification chamber, as well as tools which can be included in an assay to apply the microbial sample under test to the growth medium;

FIG. 10H is an illustrative representation, partly photographic, partly by way of line drawing, which illustrates an example embodiment in a set-up-and-incubated assay dish showing gram-negative isolated colonies (the appearance of pure culture with a measurable concentration). Microbial growth, including its termination forming visible circular zones of inhibition around the sample disks, is shown. Also shown is a top view of two translucent interfitting elements carrying interpretive indications ready to be fit into the assay dish to facilitate a result determination, in the illustrated example being elements specific for urine cultured specimens with indicated growth media types and anti-microbial agents used marked thereon;

FIG. 10I is a top view of the assay dish shown in FIG. 10H with the interfitting elements fitted, enabling a direct susceptibility test result;

FIG. 10J is an illustrative representation, partly photographic, partly by way of line drawing, which illustrates an example embodiment in a set-up-and-incubated assay dish showing gram positive isolated colonies (the appearance of a mixed culture but the gram positive isolated colonies are predominating with only a very minor gram negative species shown of two colonies in the MAC chamber). Microbial growth, including its termination forming visible circular zones of inhibition around the sample disks, is shown. Also shown is a top view of two translucent interfitting elements carrying interpretive indications ready to be fit into the assay dish to facilitate a result determination, in the illustrated example being elements set up for non-urine specimens, for example other types of cultured specimens such as wound, lower respiratory tract, etc., with indicated growth media types and antimicrobial agents used marked thereon;

FIG. 10K is a top view of the assay dish shown in FIG. 10J with the interfitting elements fitted, enabling a direct susceptibility test result;

FIG. 11 is a top view of an interfitting element, in this example embodiment of a translucent antimicrobial sample whole disk applicator with interpretive indications;

FIG. 12 is a pictorial illustration of standardized isolations of bacteria for approximating the concentration of bacteria (in colony forming units per milliliter) present in the sample. The colony isolation scheme used for these standards is in lower right box.

A listing of referenced structure in the disclosed examples, by and in order of reference number designation, may be useful in furthering understanding of the invention, and is as follows:

10—antimicrobial agent sample disk-quarter
10'(prime)—a group of such antimicrobial disk-quarters
10a—such a disk-quarter containing agent a
10b—such a disk-quarter containing agent b
10c—such a disk-quarter containing agent c
10d—such a disk-quarter containing agent d
10e—such a disk-quarter containing agent e
10f—such a disk-quarter containing agent f
10g—such a disk-quarter containing agent g
10h—such a disk-quarter containing agent h
10i—such a disk-quarter containing agent i
10j—such a disk-quarter containing agent j
10k—such a disk-quarter containing agent k
10l—such a disk-quarter containing agent l
10m—such a disk-quarter containing agent m
10n—such a disk-quarter containing a agent n
11 assay
12—sterile culture swab
13—assay kit
14—tube with sterile water
16—spreading tool
18—conventional push pin-like disk-quarter applicator
20—dish (kit plate)
21—dish (plate) lid
22—dish (kit plate), setup-and-incubated
24—growth media, e.g. CCNAB, MAC, BA, MH 25—Mueller-Hinton blood agar (BA) susceptibility-test chamber
26—Mueller-Hinton agar (MH) susceptibility-test chamber
28—Columbia CNA agar with blood (CCNAB) isolation/identification chamber
30—MacConkey agar (MAC) isolation/identification chamber
32—diagram illustration of streak of initial application of organism sample onto growth medium for colony isolation
33—post incubated location of streak 32 on actual plate
34—diagram illustration of first dilution spreading for isolation
35—post incubated location of dilution spreading 34 on actual plate
36—diagram illustration of second dilution spreading for isolation
37—post incubation location of dilution spreading 36 on actual plate showing isolated colonies
38—diagram of BA-susceptibility-test chamber with antimicrobial agent sample disk-quarters placed
39—diagram of MH-susceptibility-test chamber with such disk-quarters placed
40—mismatch of placed disk-quarter to its assumed location marked by image on interfitting element translucent film
41—sample location
42—organism, e.g. predominating species growth following incubation period
43—zone of inhibition measurement results for various antimicrobial agents
43a—radius of a zone of inhibition value for a zone of inhibition of a predominating organism species 42 under test by a sample of antimicrobial agent a
43b—a radius of a zone of inhibition value for a zone of inhibition of a predominating organism species 42 under test by a sample of antimicrobial agent b
43c—radius of a zone of inhibition value for a zone of inhibition of a predominating organism species 42 under test by a sample of antimicrobial agent c;
43d—radius of a zone of inhibition value for a zone of inhibition of a predominating organism species 42 under test by a sample of antimicrobial agent d:
43g—radius of a zone of inhibition value for a zone of inhibition of a predominating organism species 42 under test by a sample of antimicrobial agent g;
43i—radius of a zone of inhibition value for a zone of inhibition of a predominating organism species 42 under test by a sample of antimicrobial agent I;
43j—radius of a zone of inhibition value for a zone of inhibition of a predominating organism species 42 under test by a sample of antimicrobial agent j;
44—margin of a zone of inhibition
45—tabulation of interpretive standards values including distances, which can be used to determine results of "resistant", "intermediate", or "susceptible"
46—sliding caliper measurement device conventionally used for measuring zones of inhibition
47—interfitting element example, in this embodiment a translucent sheet of polymeric resin with interpretive indications for use in a BA agar-antimicrobial agent susceptibility test chamber
48—interfitting element example, in this embodiment a translucent sheet of polymeric resin with interpretive indications for use in a MH agar-antimicrobial agent susceptibility test chamber
47'(prime)—interfitting element example embodiment similar to 47, but with interpretive indications for BA-susceptibility-test chamber for gram-negative species
48'(prime)—interfitting element example embodiment similar to 48, but with interpretive indications for MH-susceptibility-test chamber for gram-negative species
49—hypothetical measuring point
a—agent "a" sample image on interfitting element
ar—agent "a" interpretive indication of "resistant" on interfitting element
ai—agent "a" region of "intermediate" on interfitting element
as—agent "a" interpretive indication of "susceptible" on interfitting element
b—agent "b" sample image on interfitting element
br—agent "b" interpretive indication of "resistant" on interfitting element
bi—agent "b" region of "intermediate" on interfitting element
bs—agent "b" interpretive indication of "susceptible" on interfitting element
c—agent "c" sample image on interfitting element
cr—agent "c" interpretive indication of "resistant" on interfitting element
ci—agent "c" region of "intermediate" on interfitting element
cs—agent "c" interpretive indication of "susceptible" on interfitting element
d—agent "d" sample image on interfitting element
dr—agent "d" interpretive indication of "resistant" on interfitting element
di—agent "d" region of "intermediate" on interfitting element
ds—agent "d" interpretive indication of "susceptible" on interfitting element
e—agent "e" sample image on interfitting element
er—agent "e" interpretive indication of "resistant" on interfitting element
ei—agent "e" region of "intermediate" on interfitting element
es—agent "e" interpretive indication of "susceptible" on interfitting element
f—agent "f" sample image on interfitting element
fr—agent "f" interpretive indication of "resistant" on interfitting element
fi—agent "f" region of "intermediate" on interfitting element
fs—agent "f" interpretive indication of "susceptible" on interfitting element
g—agent "g" sample image on interfitting element
gr—agent "g" interpretive indication of "resistant" on interfitting element
gi—agent "g" region of "intermediate" on interfitting element
gs—agent "g" interpretive indication of "susceptible" on interfitting element
h—agent "h" sample image on interfitting element
hr—agent "h" interpretive indication of "resistant" on interfitting element
hi—agent "h" region of "intermediate" on interfitting element
hs—agent "h" interpretive indication of "susceptible" on interfitting element
i—agent "i" sample image on interfitting element
ir—agent "i" interpretive indication of "resistant" on interfitting element
ii—agent "i" region of "intermediate" on interfitting element
is—agent "i" interpretive indication of "susceptible" on interfitting element
j—agent "j" sample image on interfitting element
jr—agent "j" interpretive indication of "resistant" on interfitting element
ji—agent "j" region of "intermediate" on interfitting element js—agent "j" interpretive indication of "susceptible" on interfitting element
k—agent "k" sample image on interfitting element
kr—agent "k" interpretive indication of "resistant" on interfitting element
ki—agent "k" region of "intermediate" on interfitting element
ks—agent "k" interpretive indication of "susceptible" on interfitting element
l—agent "l" sample image on interfitting element
lr—agent "l" interpretive indication of "resistant" on interfitting element
li—agent "l" region of "intermediate" on interfitting element
ls—agent "l" interpretive indication of "susceptible" on interfitting element
m—agent "m" sample image on interfitting element
mr—agent "m" interpretive indication of "resistant" on interfitting element
mi—agent "m" region of "intermediate" on interfitting element
ms—agent "m" interpretive indication of "susceptible" on interfitting element
n—agent "n" sample image on interfitting element
nr—agent "n" interpretive indication of "resistant" on interfitting element
ni—agent "n" region of "intermediate" on interfitting element
ns—agent "n" interpretive indication of "susceptible" on interfitting element
50—zone radius interpretive standards table for gram-negative species
51—interpretive indication(s)
52—interfitting element example embodiment in a translucent polymeric resin film sheet with interpretive indications carried thereon for use in a BA-susceptibility-test chamber for gram-positive species
53—sheet of polymeric resin material
54—interfitting element example embodiment in a translucent polymeric resin film sheet with interpretive indications carried thereon for MH-susceptibility-test chamber for gram-positive species
56—zone radius interpretive standards table for gram-positive species
58—interfitting element, in this example embodiment an antimicrobial agent sample disk-quarter applicator
60—sample disk segment release access hole
62—corner-cavity-disk-quarter holder portion of said applicator
63—edge-cavity-disk-quarter holder portion
64—arc-cavity-disk-quarter holder portion
65—interfitting element applicator handle, in this example embodiment an antimicrobial disk-quarter applicator handle
66—interfitting element applicator stop, in this embodiment an antimicrobial disk-quarter applicator stop
68—sample engagement cavity tooth (teeth) in sample holder portion of applicator
69—disk-quarter notch deformation caused by said
70—corner cavity fence of holder portion
72—interfitting element, in this example embodiment an antimicrobial disk-quarter applicator
74—interfitting element, in this example embodiment an antimicrobial disk-quarter applicator for BA chamber
75—divider wall of x-divided four-chamber dish
76—interfitting element, in this embodiment an antimicrobial disk-quarter applicator for MH chamber
77—outer wall of x-divided four-chamber dish
78—release tool example
80—interfitting element, in this example embodiment an unloaded applicator including a releasable adhesive (such as a pressure sensitive adhesive, or other clean-releasing adhesive) for attachment and release of antimicrobial agent samples
82—interfitting element, in this example embodiment a loaded applicator including a releasable adhesive for attachment and release of antimicrobial samples, with disk quarters loaded by releasable attachment thereto
84—interfitting element, in this embodiment a loaded applicator including a releasable adhesive for attachment and release of antimicrobial samples, with disk segments (disk-quarters and disk-halves) loaded thereon by means of said adhesive
86—antimicrobial agent sample, in this example a disk-half disk segment
88—antimicrobial agent sample, in this example a whole Kirby Bauer agent-impregnated-paper disk
88a—Kirby Bauer antibiotic "a"-impregnated-paper disk
88b—Kirby Bauer antibiotic "b"-impregnated-paper disk
88c—Kirby Bauer antibiotic "c"-impregnated-paper disk
88e—Kirby Bauer antibiotic "e"-impregnated-paper disk
88f—Kirby Bauer antibiotic "f"-impregnated-paper disk
88g—Kirby Bauer antibiotic "d"-impregnated-paper disk
88CIP—Kirby Bauer antibiotic Ciprofloxicin-impregnated-paper disk
88CF—Kirby Bauer antibiotic Cephalothin-impregnated-paper disk
88AMC—Kirby Bauer antibiotic Amoxicillin/Clavulanic acid-impregnated-paper disk
88SXT—Kirby Bauer antibiotic Trimethoprim-sulfamethoxizole-impregnated-paper disk
88 D—Kirby Bauer antibiotic Doxycycline-impregnated-paper disk
88F/M—Kirby Bauer antibiotic Nitrofurantion-impregnated-paper disk
90—antimicrobial agent sample, in this example a square shaped impregnated paper piece equal in area to the disk 88 shown adjacent to it in the FIG.
92—antimicrobial agent sample, in this example a square shaped impregnated paper piece equal in area to the half-disk segment 86 shown adjacent to it in the FIG.
94—antimicrobial agent sample, in this example a square shaped impregnated paper piece equal in area to the quarter-disk segment 10 shown adjacent to it in the FIG.
96—interfitting element, in this example embodiment a translucent polymeric resin applicator with interpretive indications, comprising an interfitting element that places the antimicrobial samples onto a growth medium in a dish chamber and stays in place through incubation to facilitate interpretation of test outcome to obtain results.
98—translucent hollow-centered pie-shaped body of the interfitting element 96, formed of polymeric resin material
100—region between interpretive indications—in this example indicating a distance correlating with an intermediate value on dual function interfitting element
102—interpretive indication, in this example indicating a distance correlating with a resistant value on dual function interfitting element
104—interpretive indication, in this example indicating a distance correlating with a susceptible value on dual function interfitting element
106—loaded dual-function interfitting element, in this example including disk-quarters loaded onto a dual-function interfitting element such as element 96 shown in FIG. 7D 108—loaded dual function interfitting element, in this example including disk-quarters and disk-half segments, loaded onto a duel function interfitting element such as element 96 shown in FIG. 7D
110—wall of chamber treated to mitigate growth medium meniscus, such as treatment with a hydrophobic coating
112—agar medium meniscus on untreated disk chamber wall
114—dish with interpretive indications on dish base, for example silk-screened or otherwise printed on dish base
116—lid which interfits with dish carrying interpretive indications coordinated with interpretive indications on dish 114, said interpretive indications being silk-screened or otherwise printed on dish lid
118—dish with growth medium and anti-microbial agent samples, in this example Kirby-Bauer disks applied in an example embodiment where Kirby Bauer disks applied by an applicator (not shown) interfitting with the dish are used
120—growth media, in this example Mueller Hinton agar media
122—dish indexing mark for registration with interfitting element(s)
124—interfitting element with interpretive indications for use with Kirby Bauer assay set up shown in FIG. 9A
126—Kirby Bauer disk image on interfitting element
128—interpretive indication, in this example a resistant interpretive indication for given agent, carried on interfitting element 124
130—interpretive indication, in this example a susceptible interpretive indication for given agent, carried on interfitting element 124
132—lid indexing mark for registration with dish
134—dish assay set up as a Kirby Bauer dish in this example embodiment, with disks applied, and with interfitting element overlay registering positionally with the sample disks enabling use of interpretive indications carried by the interfitting element for resistant, intermediate, susceptible result determination
140—interfitting element, in this example embodiment an antimicrobial sample whole disk applicator
141—interfitting element handle
142—whole disk release access hole defined by interfitting element
143—notch in interfitting element handle
144—whole disk applicator boss portion of interfitting element 140
146—sample disk engagement tooth in whole disk applicator boss 144 as part of interfitting element 140
148—chamfer of whole disk applicator boss portion 144
150—inner wall of whole disk applicator boss portion 144
152—inner base of whole disk applicator boss portion 144 of interfitting element 140
154—disk deformation caused by sample engagement tooth 146
156—assay dish, with interfitting elements fitted for application of sample disks to BA 25 and MH 26 assay dish chambers of the dish
158—release tool for use with interfitting element 140
160—set-up assay dish (kit plate), with placed whole disks on BA 25 and MH 26 and dilution of sample for isolation in CCNAB 28 and MAC 30 chambers
162—microbial sample uniformly applied to BA 25 at time zero incubation
164—microbial sample uniformly applied to MH 26 at time zero incubation
166—incubated assay plate with urine-derived microbial specimen and with various whole antibiotic disks 88, and with an isolation performed for species identification showing an apparently pure gram-negative species present
168—incubated BA chamber containing specific example antibiotic sample disks used with urine specimens
170—incubated MH chamber containing specific example antibiotic sample disks used with urine specimens
172—observable pattern of bacterial colonies within a MAC 30 chamber as a means to determine the presence or absence of a predominating species and the approximate concentration of microbes within the sample (see FIG. 12).
173—transparent interfitting element printed with interpretive indications for three antibiotics used for antimicrobial susceptibility testing, CIP, CF and AMC to be used with a urine specimen incubated in BA chamber 168
174CF—image of CF disk 88CF on interfitting element 173 to superimpose on actual CF disk in incubated BA chamber 168
174CFr—antibiotic cephalothin's interpretive indication of "resistant" on interfitting element 173
174CFi—antibiotic cephalothin's interpretive region of "intermediate" on interfitting element 173
174CFs—antibiotic cephalothin's interpretive indication of "susceptible" on interfitting element 173
174AMC(staph)—antibiotic amoxicillin/clavulanate's interpretive indication specific for *staphylococcus* where less than the indication is "resistant" and greater than is "susceptible".
176—interfitting element printed with interpretive indications for three antibiotics used for antimicrobial susceptibility testing, SXT,D,F/M to be used in connection with a urine specimen incubated in MH chamber 170
178—an assay dish after placement of interfitting elements 173, 176 into chambers 168,170 respectively after incubation with antimicrobial agent sample disks placed at sample locations for the determination of antimicrobial susceptibility
180—incubated plate of non-urine microbial specimen with various antibiotic disks 88 and an isolation for identification showing a gram-positive predominating species (see also a minor species 184 on MAC and note circular zones of inhibition around the disks 88)
182—pattern of bacterial colonies within CCNAB 28 chamber usable as a means to determine the presence or absence of a predominating species and the concentration of bacteria within the sample (see FIG. 12)
184—colonies (two) of very minor gram-negative species
186—incubated BA 25 chamber containing specific example antibiotic sample disks used with non-urine specimens
188—incubated MH 26 chamber containing specific example antibiotic sample disks used with non-urine specimens
189—transparent interfitting element printed with interpretive indications for three antibiotics used for antimicrobial susceptibility testing, FOX, CF and AMC, to be used in connection with non-urine specimen incubated BA chamber 186
190FOX—image of FOX disk 88FOX on interfitting element 189 to superimpose on actual FOX disk in incubated BA chamber 186
190FOXr—antibiotic cefoxitin interpretive indication of "resistant" on interfitting element 189
190FOXi—antibiotic cefoxitin interpretive region of "intermediate" on interfitting element 189
190FOXs—antibiotic cefoxitin interpretive indication of "susceptible" on interfitting element 189

190FOXMRSA—Less than or equal to interpretive indication on element 189, determines that a *Staphylococcus aureus* is methicillin resistant. Cefoxitin is a surrogate marker for methicillin 192—transparent interfitting element printed with interpretive indications for three antibiotics used for antimicrobial susceptibility testing, SXT,D,CIP to be used in connection with non-urine specimen incubated MH chamber 188

194—assay dish after placement of interfitting elements 189, 192 into incubated chambers 186,188 respectively for the determination of antimicrobial susceptibility 196—interfitting element, in this example embodiment a transparent antimicrobial sample whole disk applicator with interpretive indications enabling direct results determinations 198*a*—image of antibiotic "a" disk on interfitting element 198*ar*—antibiotic "a" interpretive indication of "resistant" on interfitting element.

198*ai*—antibiotic "a" interpretive region of "intermediate" on interfitting element.

198*as*—antibiotic "a" interpretive indication of "susceptible" on interfitting element.

200—an isolation chamber with superimposed colony isolation scheme.

DETAILED DESCRIPTION OF EXAMPLE EMBODIMENTS

Examples of assays 11 which can incorporate, or embody, features and advantages of the invention will now be described, but no one example will necessarily include all the features and advantages of the invention. Nor will the invention in all possible forms it might take be fully encompassed within, or limited to, the disclosed embodiment examples, even within all the variations described. With the forgoing in mind, by way of background the antimicrobial susceptibility test portion of the diagnostic method described in U.S. Pat. No. 7,262,021 will be designated "Direct Antimicrobial Susceptibility Test" or "DAST" or simply "antimicrobial susceptibility test" or "AST" in this disclosure. An example kit 13 that enables performing the DAST diagnostic method as previously disclosed is shown in FIG. 1A. The kit includes the following items: a kit plate dish 20, a lid 21, a sterile culture swab 12, a tube with sterile water 14, a spreading tool 16, an applicator 18 and a set of antimicrobial agent sample disk segments comprising in the illustrated kit a collection of disk-quarter segments 10' each disk quarter segment 10 containing one of various antimicrobial agents to be used. A discussion of the presumptive identification portion of the assay 11 will be given before more detailed discussion of the DAST portion of the assay in describing the examples given herein. This, in combination with the prior disclosure of DAST, will be useful background information for the DAST portion (in addition to disclosure of the presumptive ID portion of the assay in its own right).

With reference to FIGS. 1A-1F, in addition to the materials needed for AST, the kit 13 concurrently provides means for a presumptive identification of the organism on a number of different levels, one being whether there are a plurality of different types of bacteria present in an organism sample or essentially only one predominating type. For example, it is useful on one level to simply know if there is a pure culture of only one type of organism present, or if there is a predominating species present, in the case of mixed bacteria; or a plurality of kinds of organisms without one predominating in the sample. There are several other levels of presumptive identification possible. By way of background, it is important to note that a colony of bacteria can originate and grow from a single bacterial cell, which makes the colony thus grown unique to that one organism species. If individual colonies can be grown, or conditions for individual colonies to grow or to be inhibited are provided, and they do indeed grow (or do not grow) much more information is potentially available about the organism in each case from each colony grown. Or, in the alternative, more information can be known about an individual microorganism that did not produce a colony under a set of known conditions.

For example, as taught in the above-referenced prior disclosure, the selective media which can be used in certain dish chambers 28, 30 can give a result to the gram-positive/gram-negative level. Further presumptive identifications to the group or genus levels are made possible by growth of isolated colonies and observing colony morphology and/or by performing simple spot tests on the isolated colonies. This will be discussed in more detail below. The analysis of colony morphology and spot testing of bacterial colonies in aid of organism identification are well known in the art.

What is meant in reference to "presumptive identification" herein is an identification by means enabled by the assay 11 of at least one characteristic, trait, metabolic feature, attribute, faculty or other taxonomical datum, which provides useful information about the organism not known beforehand. The overall idea is that in addition to—and concurrently with—DAST, the assay can provide other information regarding the organism sample which can be clinically useful. For example, in addition to knowing what antimicrobial agents are effective in inhibiting organism growth, knowing something about the characteristics, traits, etc. and/or identity of an organism under test may enable a medical practitioner to undertake additional measures in treatment which can facilitate a better outcome for a patient infected by the organism.

Returning to discussion of the assay 11, organism growth media 24 (e.g. CCNAB, MAC, BA, MH) used in microbiology may be selective or non-selective. Non-selective media are free of inhibitors and support the growth of most microorganisms encountered in clinical laboratory settings. Five percent sheep blood agar is the most commonly used non-selective medium and is included in the assays 11 described in this specification. The Mueller Hinton agar with blood added is typically labeled "BA". The Mueller Hinton organism growth-enabling medium without blood is labeled "MH" and is also non-selective. Both of these media are used in the AST part of the illustrated assay kit 13. FIG. 1B shows a method of applying the bacterial sample to the BA-susceptibility-test chamber 25 (blood containing Mueller Hinton medium) and MH-susceptibility-test chamber 26 (Mueller Hinton medium) where the DAST is run. The DAST is valid when there is a pure culture or a predominating species present—i.e. more than about ten times as numerous as any other species, in the case of mixed cultures.

Columbia CNA with blood (CCNAB) and MacConkie (MAC) growth media 24 are located in the isolation/identification chambers 28, 30 in the upper left and upper right quadrants, respectively, of the dish 20 in the example dish embodiment shown in FIG. 1B. They are selective_media, and can generally be used to establish a presumptive identification to the gram negative/gram positive level: gram-positive bacteria grow on the CCNAB and are inhibited from growing on the MAC. On the other hand, gram-negative bacteria grow on the MAC medium and are inhibited from growing on the CCNAB.

FIG. 1C shows a method of isolating the microorganism for purposes of a presumptive identification, quantitation and determination of a pure culture, or a mixed culture with or without a predominating species. For purposes of this disclosure a predominating species is a species that is present at essentially ten times (or more) the colony count of the next most prolific of the other species present. Briefly, for the isolation of individual organisms to allow for the formation of separated colonies, a user applies with a swab 12 a sample including organism(s) from an infection site as a streak 32 across the CCNAB chamber 28 and MAC chamber 30 close to the chamber borders. A first dilution is then made. This is done by using one end of a spreading tool 16. The tool is moved across the growth media with a back and forth motion in the two chambers as shown at a first dilution spreading 34. A second dilution spreading 36 is made using the other end of the spreading tool 16. Post-incubation results of this process are seen in FIG. 1E on the dish plate 22 as set up and incubated. Different amounts of microorganism growth, here a bacteria, are evident at post-incubated initial streak 33, post incubated first dilution spreading 35, and post incubated second dilution spreading 37. Isolated colonies are evident at 37. The presumptive identification to one level spoken of is that the organism is gram negative; this because of its growth on the MAC growth medium and its inhibited growth on the CCNAB medium.

An observation of the various organism colony morphologies on the dish plate 22 allows a user to make a presumptive determination of how many different species are present. In addition, when there is a pure culture or a predominating species present, a determination can be made to find the approximate concentration of organisms present on the plate by referring to the picture set, shown in FIG. 12, of various concentrations of like organisms generated by using known concentrations of organisms applied to the CCNAB chamber 28 or MAC chamber 30 as described above. This is important because of a principle known in the prior art of disk diffusion AST assays as the "inoculum effect". It is important not to overwhelm the antimicrobial samples in the test dish with too high a concentration of microorganisms. The kit used in the current embodiments is valid through a large range of concentrations on the plate from $10^4$/ml to $10^8$/ml. If the inoculum exceeds the upper value or is less than the lower value, the assay result may be suspect due to this consideration, and the AST can be re-run using the isolated microorganisms. In addition, in the case of urinary tract infection specimens, it is possible to prescreen the sample for microorganism concentration, by using a urine dipstick (as known in the art) that assays for nitrate reductase and leucocyte esterase. If these enzymes are present, a dilution into sterile water can be made before applying the sample to the growth media 24 of the dish.

Microbiologists use various characteristics of microorganism colonies that grow on the surface of agar culture growth-promoting media to make a further presumptive identification to the group or genus level. Size, shape, consistency, color and pigment production by the colonies, as well as the presence of hemolytic reactions on blood agar, are the criteria commonly used. In addition, simple spot tests on the colonies further help to identify different groups of bacteria. For example, if a sample of a colony placed in 3% hydrogen peroxide forms bubbles of oxygen, this indicates the presence of the enzyme catalase. *Streptococcus* and *enterococcus* lack this enzyme, while *staphylococcus* is positive for this enzyme. Other spot tests as known in the art can be used, such as the cytochrome oxidase test used with gram-negative organisms. When cytochrome oxidase is present in a sample taken from a colony, you can rule out all members of the family of Enterobacteriaceae FIG. 1D illustrates the result of applying the antimicrobial agent sample disk-quarters to the edge and corners of a BA chamber 38 (25 in FIG. 1B) and a MH chamber 39 (26 in FIG. 1B). The BA chamber as diagrammatically shown set up for a test includes disk-quarters placed adjacent the sides of the chamber and separated to minimize overlap of inhibition zones; and the MH chamber also has additional disk-quarters thus placed. Prior to the invention, a user took the applicator 18 and stabbed and picked up the paper antimicrobial sample disk-quarter segments 10 and carefully effected placement into the BA and MH chambers 38, 39 (25 and 26 in FIG. 1B). Prior to the invention, the user placed the disk-quarters carefully by eye so that they are spaced equidistantly abut the edge of the dish and/or fit into the corners as shown in FIG. 1D. This careful placement adjacent the outer perimeter of the chamber in each case is desirable and allows the DAST portion of the assay 11 to be essentially equivalent in many respects to a standard Kirby Bauer disk diffusion test as typically set up and run in a clinical laboratory setting. This hand placement process is time-consuming and requires care on the part of the user in placing the samples of each of the different antimicrobial agents at specific locations and in just the right position relative to the adjacent wall of the chamber 38, 39 (or two walls in the case of a corner location in a chamber).

Following a period of time, the set up and incubated kit plate dish 22 as shown in FIG. 1E includes colonies of a predominating species 42, both individual colonies 37 in the ID portion of the assay dish, and as a lawn of the organism in the AST portion of the assay dish, this as a result of growth of this actual predominating species during incubation. Generally, the period of time for incubation can be as short as 8-12 hours, depending on various factors familiar to one skilled in the art. Various zones of inhibition are generated by the various antimicrobial agent disk-quarters: 10*a*, 10*b*, 10*c*, 10*d*, 10*e*, 10*f*, 10*g*, 10*h*, 10*i*, 10*j*, 10*k*, 10*l*, 10*m*, and 10*n*. The sizes of the zones of inhibition are defined by the margin of inhibition 44 in each case. When quarter disk segments against the walls are used the inhibition zones are measured, in millimeters, as a radius from the inside corners and outside edges of the chambers of the dish, as may be the case in each instance, to the margins 44. Six zone measurements are illustrated in FIGS. 1E and 1F. The six examples are: inhibition value of species by agent "a" 43*a*, inhibition value of species by agent "c" 43*c*, inhibition value of species by agent "d" 43*d*, inhibition value of species by agent "g" 43*g*, inhibition value of species by agent " " 43*i*, and inhibition value of species by agent "j" 43*j*.

The advantage in measuring from the outside of the wall of the chamber of the dish 22 kit plate for the edge-placed disk-quarters (versus the corner measurement from the inside corners) is to mitigate and correct for different diffusion dynamics of edge placement versus corner placement of sample disk-quarters 10. Several measuring points 49 are shown in FIG. 2D and FIG. 2E. Three figures in U.S. Pat. No. 7,262,021—namely FIG. 2A, FIG. 3B and FIG. 3C of that disclosure—also illustrate this issue. FIG. 2A of U.S. Pat. No. 7,262,021 shows the geometric equivalence between corner placement of a disk-quarter and measuring a radius from the inside corner to the margin compared to measuring a diameter for a whole disk. On the other hand, FIG. 3C of U.S. Pat. No. 7,262,021 shows that when the abutted disk-quarter is along the straight edge or along the curved edge and measurement is from the inside, it is slightly less than that needed to be equivalent after multiplying that radius measurement by two and comparing against the whole disk measurement. A half disk placed at the edge as shown in FIG. 3B of U.S. Pat. No. 7,262,021 returns the comparisons to an essentially equivalent status. The correction method for edge-placed disk-quarters for the current example embodiments shown and discussed herein is to use the disk-quarters and measure from the outside of plate wall to the margin. However, half disks substituted for quarter disks at the inner edges and along the inner arc of the plate allow for measurement from the inner wall to the margin. It has been found that the wall thickness (about 0.5-1.0 mm) is essentially equivalent to the correction needed for said equivalence with use of disk half segments in the illustrated embodiments. Use of the half segments at wall lactations and quarter segments in corner locations is in turn essentially equivalent to conventional standardized Kirby-Bauer methodology in terms of diffusion of the agents in the growth media, and thus with spatial relationships between the margins of the zones of inhibition and the sample locations.

The six illustrated measurements in FIG. 1E (43a, 43c, 43d, 43g, 43i, and 43j) and the non-illustrated remaining values are entered into a zone radius interpretive standards table, such as the example shown in FIG. 1F. See the zone of inhibition measurement results 43 column in the figure where they are thus entered. These zones of inhibition measurements are compared and matched to the standard interpretive values 45 of the table which are then interpreted to "Resistant" ("R"), "Intermediate" ("I") or "Susceptible" ("S") depending under which heading they fall. The result, or grade, of R, S, or I (the assay result) is found in the far right column of the table of FIG. 1F. Prior to the invention, a means conventionally used to measure the relevant distances to the margins of the inhibition zones was scaling off directly with a ruler or by using a sliding caliper device 46 as shown in FIG. 1E to obtain the measurement 43. This, again, requires time and care to obtain accurate results. Mitigation of parallax, careful placement and steady holding of the measuring device, concentration and due attention in reading the scale, and transposing the distance reading to a results tabulation, etc. in obtaining the distance measurement can add to the difficulty of performing the assay. As mentioned, these add to the time required in obtaining the result. These considerations, as well as the time and care required in setting up the AST testing portion of the assay mentioned above, require more time to be spent by the user. Thus, these considerations add to the cost of performing the test.

The invention can enable faster set up of the AST portion of the assay, and direct reading of a result. This can reduce the time required, as well as difficulty, in performing the assay. Moreover, it is not just a matter of shaving a few minutes off a 8-14 hour test, but in a practical sense dramatically reducing the time and effort required on the part of those doing each test. This enables many more tests to be done in the same time period by a person in the lab, or at any point of care, using the assay. Specific example implementations of the invention will now be discussed in further detail.

Detailed Description of the Examples of FIG. 2A-FIG. 2F

With reference to FIGS. 2A through 2F, provision of an interfitting element (e.g. 47, 48) can enable at least one of more accurate application of the antimicrobial agent samples to the growth medium at desired locations 41, and direct reading off of an assay result. The interfitting element is configured to interfit with the dish in a specific way with a tolerance selected to provide desired accuracy in relative spatial locations pertinent to the testing, as will be discussed in more detail below. Two example embodiment interfitting elements are illustrated in FIG. 2A. The outer dimension is the essentially the exact dimension of the inner chamber of an x-dish (quad-plate) dish 20 as used for the plate of the assay 11, less a clearance distance of about 0.1 millimeter or less in one example. The clearance distance can be selected to be about 0.05 millimeter in another example. Since the test results are conventionally based on measurements to the nearest 0.5 millimeter, the clearance distance is selected so that it does not introduce error in obtaining a result. If the interfitting element is flexible enough so that it can be interfitted without providing a clearance distance, the clearance distance requirement can be neglected. It will be appreciated that the manufacturing tolerance will be held closer than the clearance distance.

In this illustrated embodiment, the interfitting element is made of a translucent polymeric resin, and can comprise a conventional transparency film such as is used in providing overhead transparencies. An advantage of this material is that it can be provided with interpretive indications 51 (e.g. "ar" and "as" arcs in FIG. 2A) by various printing methods, including "laser printing" using conventional equipment. The film material of this example embodiment can be biaxially oriented polyethylene terephthalate (boPET). The transparency film is made with a water-based coating accepting fused toner depositions, which facilitates crisp, high-quality images. The interpretive indication and sample location images on the transparency films used in the illustrated embodiment can be printed with a high-resolution laser printer in this example. This can be done at relatively low cost. Other modes of applying the images are possible, for example etching, scribing, stamping, thermal jet deposition of ink and/or jetable polymeric resins (to provide raised indicia), screen printing, offset printing, or other conventional printing methods adaptable to creating the images on a polymeric film substrate. The material of the film, and/or its surface treatment and/or applied coating, is coordinated with the image deposition method to obtain suitable interpretive indications. Line thickness, darkness of line, color (if used), and accuracy of the imaging process can all be important to produce interpretive indications facilitating accurate AST portion results in the assay 11. Conventional printing methods, widely available, can be employed to accomplish these objectives.

As shown in FIG. 2A, interfitting elements 47, 48 for BA chamber 25 and MH chamber 26 are printed with seven quarter-disk images: three in the three corners, two centered along straight edges and two equidistant along the arc of the curved wall portions of the chambers. Images match in size to the antimicrobial sample disk-quarter segments 10 in each case. This is done so that sample locations 41 will be clearly observable; and moreover, observable in relation to the interpretive indications 51 comprising arcs (e.g. ar, as arcs, in the left top corner of the element 47 in the figure) in the illustrated examples. The placement and spacing of the antimicrobial agent samples, and the agents to be placed into the chamber (s), are selected and coordinated taking into consideration the reasonably expected size of the zones of inhibition to be formed in performing the AST portion of the assay. This is so that the most differing antimicrobial agents can be placed in each chamber without undue interference with each other. The interpretive indications can also have other embodiments such as discontinuous arcs drawn or printed on the films. The arcs can be printed in different colors, line styles, or other means to differentiate one from the other. Also instead of arcs for instance, radial lines can be printed on the film to represent the values of resistant or susceptible.

As will be appreciated, using smaller sample sizes and different distances to the margin of the zone of inhibition developed to coordinate with the smaller sample sizes could enable more agents to be tested in the same size chamber as in the illustrated example. However, this involves moving away from the concentration/distance relationships of conventional Kirby-Bauer methodology. One reason for the particular configuration of the illustrated example is that it is essentially equivalent to a standard Kirby-Bauer approach in this respect; and the distance measurements are directly comparable to those obtainable in that standardized methodology. The advantages of this will be apparent to one skilled in the art. However, with sufficient development, including statistical showing of equivalence, using smaller samples can enable the possibility of providing more samples of different agents in a similar space, enabling conducting AST with respect to more potential treatment agents concurrently on the same assay dish 20.

Discussion of details of the example will now be presented. The BA chamber interfitting element 47 carries antimicrobial agent sample disk-quarter images labeled a, b, c, d, e, f, and g. The MH chamber interfitting element 48 has disk-quarter images labeled h, i, j, k, l, m, and n. Each of these image labels represents a corresponding antimicrobial agent disk-quarter: (10a, 10b, 10c, 10d, 10e, 10f, 10g, 10h, 10i, 10j, 10k, 10l, 10m, and 10n in FIG. 2B). The choice of antimicrobial agent used is generally a function of the source of the infection and caregiver's preferences. Different assays for different suspected infection types or infection sites can be provided, each having the most likely antimicrobial agents represented in the sample mix of the AST portion of the assay 11 for treating the infection the caregiver is targeting.

The interpretive indications 51, located in the upper left panel of FIG. 2A, are in the form of two arcs associated with each disk-quarter image on the film in each case. An inner arc located a specified distance out from the disk-quarter image, and outer arcs located a specified distance farther out are provided. The inner arc represents and indicates the maximum distance to a zone margin corresponding with a finding of "resistant." The outer arc likewise indicates a minimum distance for a finding of "susceptible" in determining the assay result. The region in between the arcs represents a result of "intermediate" for the test. For instance, in the example of element 47 for the "a" image of the sample location in the upper left corner if the interfitting element in the figure, the inner arc of resistant is labeled ar, the outer arc of susceptible is labeled as, and the region of intermediate sensitivity labeled as ai. The same labeling system holds true for the remaining disk-quarter images: br, cr, dr, er, fr, gr, hi, ir, jr, kr, lr, mr, nr, for resistant arcs. The susceptible arcs are labeled: as, bs, ds, es, fs, gs, hs, is, js, ks, ls, ms, ns. The intermediate regions are labeled: ai, bi, ci, di, ei, fi, gi, hi, ii, ji, ki, li, mi, ni.

The antimicrobial agent samples and the interpretive indications can be different as between gram positive and gram-negative organisms. The illustrated example an interfitting element 47' with interpretive indications for a BA-susceptibility-test chamber 25 for gram-negative species is shown in the lower left quadrant of FIG. 2A and in FIG. 2D. An interfitting element 48' with interpretive indications for MH-susceptibility-test chamber 26 is shown in the lower right quadrant of FIG. 2A and in FIG. 2D. These two interfitting elements are shown in FIG. 2B as they would be if inserted into the BA and MH chambers 25, 26 of the AST portion of an incubated kit plate dish 22 such as that shown in FIG. 1E.

It will be observed that without care in placement of the antimicrobial agent sample disk segments 10, there can be mismatches 40, as illustrated in the example shown in FIG. 2B, between the locations of sample disk-quarter segments 10 in the chamber 25, 26 and the corresponding images on the films of the interfitting elements 47', 48'. This highlights a need for an application system that can place the disk-quarters into the chambers with precision so as to provide registration with (that is to say, line up with) the images on the films, including the sample locations and interpretive indications (e.g. a, ar, as, etc. in FIG. 2A). Even though there is an offset 40, as shown in FIG. 2B, it can be possible to obtain a direct result reading but it requires more time and effort to obtain the result. Careful measurement, or careful shifting of the film, could be done, for example to obtain the result in each case in the example shown. A comparison of the result of the assay illustrated in FIG. 1E and FIG. 1F, to the result of using the interfitting elements as illustrated in FIG. 2B is shown in FIG. 2C. They are shown to be essentially equivalent.

With reference to FIG. 2D the interfitting elements 47', 48' described in connection with in FIG. 2A are enlarged for clarity. The specific millimeter standard distance values for interpretation to "resistant" (inner arc), "intermediate" (region between arcs) and susceptible (outer arc) are shown. It will be appreciated that the inner arc distance value represents a distance from the sample location 41 to the margin of the zone of inhibition that the margin must be observed to be less than or equal to in order for a "resistant" result to obtain. Likewise the outer arc represents a distance that the observed margin must be seen to be equal to or greater than for a "susceptible" result to obtain. If the margin is observed in between these arcs an "intermediate" result obtains. These distance values come from the zone radius interpretive standards table 50 for gram-negative species for each of the specific antimicrobial agents used in the test. See these values listed under the heading "Radius measurement in mm" in said table 50. The essential equivalence of using the interpretive indications to using a standard table will be apparent.

FIG. 2E illustrates another example embodiment in interfitting elements 52, 54 which can be used for DAST of gram-positive species in the assay 11. These include an interfitting element example embodiment with interpretive indications for a BA-susceptibility-test chamber and for gram-positive species (element 52), and a interfitting element example embodiment with interpretive indications for a MH-susceptibility-test chamber and for gram-positive species (element 54). The zone radius Interpretive standards table 56 for gram-positive species is provided to enable comparison with, and confirmation of equivalence to, data and results obtainable using the table in this example and the interpretive indications carried by the interfitting elements As described in connection with FIG. 1E, in AST the zones of inhibition are measured for each of the antimicrobial agents tested. These values are then matched with the value in the interpretive standards table to determine a result, comprising resistant, intermediate or susceptible designations with respect to each of the antimicrobial agents tested. With reference again to FIGS. 2A-F an improvement in the AST assay portion using an interfitting element enables faster determinations by a user with less difficulty, in that it is only necessary to drop the interfitting element into the incubated chamber (shown in FIG. 2B) and visually note where the margin 44 is relative to the interpretive indication arcs 51 printed on the film and record the result, which is thus directly determined without other measurement or resort to an interpretive table. Referring to FIG. 2B, if the margin 44 is less than or equal to the inner arc, e.g. br, cr, dr, er, fr, gr, hi, ir, jr, kr, lr, mr, and nr, corresponding with a particular agent sample disk segment, then the species 42 under test in the chamber is resistant to the particular agent. If the margin 44 is equal to or greater than an outer arc as, bs, ds, es, fs, gs, hs, is, js, ks, ls, ms, ns then the species 42 in the chamber is susceptible to the particular agent. If the margin 44 lies between the arcs, then the particular antimicrobial agent has an intermediate affect on the species 42. This visual comparison and determination can be done for each agent sample in each chamber. This greatly reduces the time required to determine results in each assay and enables a given number of laboratory personnel or other users to accurately process a greater number of assays in a given time period in comparison with prior methodology. This can result in considerable cost savings per test without resort to very high volumes or automated methods having high initial investments in attendant supporting laboratory systems. It will be appreciated that the benefits afforded by the invention illustrated in the example can be most appreciated in economically challenged areas where the test can be used and laboratory staff and resources are limited.

Likewise, with reference to FIG. 2D two interfitting elements 47' and 48' each carry seven images a, b, c, d, e, f, g and h, i, j, k, l, m, n corresponding to fourteen antimicrobial agent sample-containing disk-quarters: 10a, 10b, 10c, 10d, 10e, 10f, 10g, 10h, 10i, 10j, 10k, 10l, 10m, 10n. Table 50 (and also the table 45 of FIG. 1F) lists a set of fourteen antimicrobial agents under the heading "antimicrobial." This example set of agents is recommended for use with gram-negative organisms such as may be found in a urinary tract infection. The method can use different sets of antimicrobial agents for different types of microorganism infection, as mentioned. This set of interfitting elements also provides the benefits discussed just above, as do the other example embodiments incorporating interpretive indications facilitating a direct result determination.

To further expand the explanation of the relationship between the prior art practice and the invention using an interfitting element with interpretive indications as in the example embodiments, the reader is commended to look again at the table 50 in FIG. 2D. You can see that agent "a" is the antimicrobial agent "ampicillin". The interpretive indication resistant arc for a on film 47' measures 6.5 mm. Checking the table 50 for ampicillin, in the column labeled "resistant" is the value 6.5 mm. This is a radius distance, and in turn corresponds with a 13 mm diameter which would appear in a conventional Kirby-Bauer interpretive table. The interpretive indication susceptible arc on the film 47' for ampicillin measures 8.5 mm, which is the ampicillin value in table 50 for "susceptible". The intermediate value in table is 7-8 mm and is the region on the interfitting element between the resistant arc and the susceptible arc.

Another example using interfitting elements 52, 54 is illustrated with the help of FIG. 2E. This is a situation where the assay 11 allows for an organism 42 that is a gram-positive species. This circumstance presents a special case where four antimicrobial agents (a, b, c and f) have interpretive standard values that depend on a presumptive identification of a gram-positive organism to the genus level of *staphylococcus, streptococcus*, or *enterococcus*. These can be presumptively determined and subcategorized as described in the prior disclosure and as known in the art using hemolytic characteristics of the organism, growth on CCNAB medium, and the presence or absence of catalase activity using 3% hydrogen peroxide. Agent "a", which is ampicillin in this embodiment, only has susceptibility arcs. Margins of inhibition 44 that are less than the susceptibility arc are resistant. FIG. 2E, film 52 shows for a arcs labeled 14.5 mm, 12 mm, and 8.5 mm. The 14.5 value is for *staphylococcus*, the 12 mm value is for beta-hemolytic *streptococcus* and the 8.5 mm value is for *enterococcus*, which can be presumptively identified from its catalase negative and non-hemolytic characteristics.

The antimicrobial agent "b", which is vancomycin, has a similar situation to the ampicillin in that for the *staphylococcus* and *streptococcus* there is only a susceptibility arc. It is 7.5 mm for the *staphylococcus* and 8.5 mm for the *streptococcus*. The *enterococcus* on the other hand has a resistant, intermediate and susceptible arc at less than or equal to 7 mm for resistant, equal to or greater than 8.5 mm for susceptible and between the two arcs for intermediate.

The third situation is for agent "c", which is amoxicillin/clavulanate. The only gram-positive organism listed in interpretive tables for that antimicrobial agent is *staphylococcus*, which only has a susceptible arc at 10 mm. A margin of inhibition 44 less than that value is resistant.

The final situation where there is a special case with the antimicrobial agents in this set is the antimicrobial agent "f", which is cefoxitin. This agent is important because it is a good surrogate marker for methicillin resistant staph. aureus commonly referred to as MRSA. The interpretive indication arc at 11 mm assays for MRSA: a margin formed by staph. aureus that is less that 11 mm can be identified as MRSA. Staph aureus has colonies that are golden in color, beta-hemolytic and catalase positive. The golden colony characteristic usually takes more that 24 hours to express itself. There is a reliable and accurate spot test that gives immediate results following an overnight DAST incubation and that is Oxoid's Dryspot Staphytect Plus kit (Manufactured by Thermo Fisher Scientific, Oxoid Ltd. Division, of Cambridge, U.K.). Used in conjunction with the invention, this allows for a rapid MRSA test also giving available options for more rapid therapy. Other gram-positive species including non-staph aureus have a resistant and susceptible arc with an intermediate region in between. Those values are less than or equal to 7 mm for resistant, equal to or greater than 9 mm for susceptible and intermediate between the two arcs.

With reference to FIG. 2F, various printed interfitting elements with interpretive indications to be cut out (e.g. 47', 48') can be printed on a single sheet 53 of transparency material. Manufacturing of the interfitting elements can be done using a conventional laser printer as discussed above. In one example manufacturing method, numerous designs for different sets of interfitting elements can be stored electronically, and interfitting elements manufactured as needed by printing indicia such as that shown in the figure onto transparency material, then cutting out the elements using dies, shears, cnc cutting equipment, or other known means. The film can be "kiss-cut" before printing in one example embodiment. As mentioned, this can be done at relatively low cost compared to other methods, particularly when production volume is low. At higher volumes, other methods of manufacture—such as those mentioned above—can be advantageously employed.

Detailed Description of the Examples of FIG. 3A-FIG. 5-C

Turning now to FIGS. 3A and 3B, the problem of accurate placement of antimicrobial agent samples in dish chambers so as to provide registration with interpretive indications will now be addressed. In another example embodiment of the invention the assay 11 can include one or more interfitting elements 58 configured as antimicrobial agent sample applicators as illustrated in these figures. The interfitting applicator element 58 is formed of a polymeric resin and can be formed by an injection molding process. The applicator is configured to interfit with the dish in one of the x-wall-defined chambers (e.g. 25, 26 in FIG. 1B) to facilitate accurate placement of samples at desired sample locations as discussed above. Disk segment holder portions, e.g. 62, 63, 64, hold the samples until they are released onto a growth medium in the disk chamber in setting up the AST portion of the assay. A release access hole 60 is centered in each of a corner-cavity-disk-quarter holder portion 62, an edge-cavity-disk-quarter holder portion 63 and an arc-cavity-disk-quarter holder portion 64. The release access holes provide access to disk segments loaded onto the applicator to facilitate releasing the disk segments from the applicator. Also evident is a number of applicator stops 66 which cooperate with the dish, specifically a top portion of the walls thereof (not shown in the figures) in holding the interfitting element a desired distance above the agar while the disk segments are being released. The interfitting element is shaped to fit into the chamber and the discussion above regarding clearance and tolerances for the interfitting element applies here as well. An applicator handle portion 65 is provided for improved purchase on the element in handling it and interfitting it with the dish.

Further details will be appreciated with reference to FIGS. 3C and 3D, which illustrate features and advantages of an corner-cavity-disk-quarter holder 62 and edge-cavity-disk-quarter holder 63. These are configured to hold antimicrobial agent sample disk segments, specifically quarter segments, to be applied to the growth medium until they are actually intentionally applied at desired sample locations 41 in the chamber as discussed above. The corner cavity holder portion includes a corner-cavity-fence 70 on each side. This fence is very thin, to aid in placing the sample as snugly as practicable into a corner of the chamber adjacent two walls. The holder portions can also include at least one cavity tooth 68. Two are provided in the illustrated embodiment corner cavity holder portion, and three in the edge cavity holder portion. These deform the disk segments, setting up a rebound force that helps hold the segments more tightly in the holder portions by exerting outward force on the holder portions and thereby increasing friction between the element and the sample disk segments held thereby.

In another example embodiment, the teeth are omitted and the cavity holder portions are made slightly undersize, and so act to deform the sample disk segment. The advantage of teeth is that the cavity can be made slightly oversize, and the teeth deform the sample disk segment more in localized areas and less overall, and so more variation in disk segment size can be accommodated and still perform as desired to hold the samples in the applicator interfitting element 58 until they are intended to be released onto the growth medium. In another example embodiment, a releasable adhesive (such as a clean release adhesive or a pressure sensitive adhesive) can be provided in the cavity holder portions to increase the hold on the disk segments. A further example interfitting element embodiment would provide a flat base without the cavity. The antibiotic papers can be attached using a releasable adhesive, for example a two-sided high tack/low take tape can be used in one embodiment. The disk quarters or disk halves etc. would be positioned under the release access holes, and this arrangement can give rise to economies in manufacturing different from those obtained with the cavity interfitting elements. The papers (disk quarters) could be provided separately and covered for storage and shipping using the peelable kraft paper that is integrated with the adhesive tape roll. In another example they can be attached to the interfitting element as a manufacturing step and shipped and stored attached to the interfitting element. In another example the surface of the element in the cavity holder portion can be roughened, or mutilated to provide projecting spikes of polymeric resin material (conventional, not shown). These surface treatments can increase the friction hold between the applicator element and the samples held in the cavity holder portions 62, 63, 64, particularly in combination with slight deformation of the sample disk segment and/or the applicator material to provide a friction enhancing rebound force between the sample and the applicator.

The release access hole 60 is provided to facilitate pushing the disk segments out of the cavity holding portions, and seating them onto the surface of the example agar-based growth media, using a release tool (78 in FIG. 4D) provided with an assay kit or other probe, spike, point, etc. Said hole is round in the illustrated example, but another shape can be used, for example an elongated slot enabling urging the sample disk segment toward a wall in releasing it while at the same time limiting its transverse movement along the wall. The release tool can be made close enough in size to the release access hole size that lateral movement off of an intended sample location on the growth medium is prevented by interference between the tool and the interfitting element, the interfitting element in turn being constrained from lateral movement by its interfit with the dish 20.

With reference now to FIGS. 3E and 3F, it can be further appreciated that the interfitting element 58 can be loaded with antimicrobial agent sample disk segments 10, and these can be held therein until properly positioned by the applicator in the disk chamber. In one example the loading is done as the kit for the assay 11 is manufactured. The loaded applicator element is then sealed with moisture controlling provisions in an enveloping package. If proper precautions regarding storage temperature are followed, a moisture-controlling packaging which is undisturbed can promote a reasonable shelf life for a kit containing one or more loaded applicators. In one example embodiment, the enveloping packaging (conventional, not shown) is close fitting, and can be vacuum packaging. This packaging envelopment can contain moisture-absorbing material, can contain an alternative gas to air, such as nitrogen or another inert gas, and can be at a pressure below atmospheric pressure.

In another example embodiment, the sample disk segments 10 are separately packaged in a moisture-controlled shelf-life preserving environment; and are loaded onto the applicator interfitting element 58 just before use in setting up the assay 11. This example is less convenient, but allows customization at the point of use. Numerous interfitting elements having interpretive indications can be provided covering assays targeted for a larger number of infection types, infection sites, etc., and few (e.g. two) interfitting elements configured to act as applicators, and a wider variety of antimicrobial agent samples. Thus assays for a wider variety of infection types can be set up from a single assay kit, albeit with slightly more trouble than would be the case with pre-loaded applicators.

FIGS. 3G and 3H illustrate a loaded antimicrobial-disk-quarter applicator interfitting element 72 showing disk-quarters 10 firmly held by—and/or releasably attached to—the interfitting element. As just discussed it is contemplated that the end user will generally prefer to start with a kit containing interfitting element applicators that are preloaded during manufacturing as just described. Many different configurations and antimicrobial agent combinations are possible. As discussed above the assay kits incorporating the invention can be categorized—for example in selection of antimicrobial agents, and growth media types, and in additional elements with variations provided, or even essentially tailor made for one specific infection—to suit the type and/or source of infection, and/or the antibiotic candidate preferences of the health care worker(s) involved in doing the testing. Thus a coordinated set of interfitting elements including applicator functionality and interpretive indication functionality can be configured for assays directed to one type of infection, or to one site, or to a caregivers preference. For example assays directed to urinary tract infections can have one set of antimicrobial agents, that set in turn coordinating with a set of growth media types in the dish, whereas an assay directed to lower respiratory tract sputum samples can have different sets. Further, the sets might differ based on the general type of infection suspected, even though the infection sample site might be the same; for example two different assays for two different types of suspected infections, though the sample source for both might be a sputum specimen, for example.

With reference to FIGS. 3I and 3J further details regarding a loaded corner cavity 62 and edge cavity 63 disk segment holder portions can be appreciated. The drawing figure shows how the sample disk-quarter is held into the cavity with the fence 70 borders and the teeth 68 in the case of the corner cavity. A disk-quarter notch 69 forms in the sample disk segment by deformation of the sample disk segment by the action of the tooth 68 upon the edge of the disk-quarter 10 discussed above. As discussed, this allows for a snug fit, which withstands jostling attendant transport and handling before use. In the case of the loaded edge-cavity 63 the disk-quarter 10 is secured in position with the aid of three teeth 68 that push notches 69 into the disk-quarter 10. It will be appreciated that a half disk segment cavity holder portion cab be provided having a combination of features from the illustrated holders. For example, an edge holder cavity for a half disk can have at least one fence 70 adjacent an edge of the element and teeth 68 along the arc of the circumference of such a cavity holder (64 in FIG. 3A) and is very similar in construction to the edge holder 63 and corner holder 62. Doubling the corner holder portion shown by rotating projection about an axis along one of the straight edges thereof would create such a half disk sample holder portion, for example, having two fence portions, one adjacent each outside corner, and four teeth spread along the arc of the circular outer circumference of the cavity. Other configurations of antimicrobial samples can be used with corresponding shapes in the applicator. See future discussions for FIG. 7A, FIG. 7B and FIG. 7C below.

Turning now to FIG. 4A through 4E the use of the interfitting element 74, 76 providing an antimicrobial agent sample applicator will be described in more detail. FIG. 4A illustrates the operation of a specific example interfitting element antimicrobial-disk-quarter applicator 74 designed for the BA susceptibility test chamber 25 of the dish 20. A loaded interfitting element antimicrobial-disk-quarter applicator for BA chamber, containing up to seven antimicrobial disk-quarters 10, and ready for placement into the BA chamber, is poised above the dish just as it would be if about to be interfitted with the dish. The four applicator stops 66, which rest on top of the x-dish divider wall 75 as previously discussed will support the applicator when set in the dish. The notch shape of the back of the applicator handle 65 interfits with, and rests on the top of, the higher plate outer curved wall 77. This configuration provides the correct altitude above the BA agar medium contained in the BA chamber when the applicator interfitting element is seated.

As shown in FIG. 4B, after placement of interfitting element applicator 74 in the BA chamber the stops 66 rest on the tops of the plate inner wall dividers 75 and the handle 65 notch rests on top of the outer curved plate wall 77. Since both the BA and MH chambers 25, 26 respectively, facilitate AST in the examples illustrated herein, a loaded antimicrobial-disk-quarter applicator 76 for the MH chamber 26 is shown poised above and ready for placement in the MH chamber in the example embodiment. The example embodiment dish with both interfitting elements providing applicator function interfitted is shown in FIG. 4C. They are in position for the next step of disk-quarter removal from the applicators and insertion into the chambers onto the growth media at the intended sample locations 41. This is illustrated by FIGS. 4D and 4E. FIG. 4D illustrates a poised release tool 78 that will be used to dislodge disk-quarters from the applicators. The release tool is configured with a self-stopping shape that that will prevent the tool from being inserted too far into the release access hole and pushing the disk too far down into an underlying growth medium. After the sample disk quarters have been pushed off onto the agar growth media, the applicators 74, 76 are removed from the dish 20.

It will be apparent from the discussion of these figures, which illustrate the value of the interfitting elements 74,76 configured as applicators, that they can provide proper and correct placement of the antimicrobial agent sample disk segments (quarters) 10 at intended sample locations 41 for alignment and coordination of position with the previously described interfitting elements carrying interpretive indications 51. This facilitates post-incubation matching up of positions of said samples and indications for direct results indication.

For example, FIG. 5A shows a portion of the dish 20, including the BA set-up susceptibility-test-chamber 38 with disk-quarters placed, and the set-up MH susceptibility-test chamber 39 with disk-quarters placed, this following the operation of the interfitting element applicators 74 and 76 as just described and their subsequent removal. The disk-quarters are tucked into corners and abutting inner walls of chambers at the intended sample locations 41 as called for. FIG. 5B illustrates example interfitting elements 47, 48 for the BA and MH susceptibility test chambers, respectively, for gram negative species as heretofore described herein. When these are then interfitted with the dish as FIG. 5C illustrates, the accurate match of the interpretive indication carried by the interfitting elements and sample location image directly over the inserted antimicrobial disk-quarters allows for an accurate result. (Contrast this example with that of FIG. 2B showing double arrows 40 marking non-superimposed film images over the placed disk-quarters, which make a AST result harder to interpret as discussed).

Although not shown on the interfitting elements 74, 76 acting as sample applicators shown in FIGS. 3A through 4E (for reason of showing that structure more clearly), in another example embodiment interpretive indications can be printed or otherwise carried on these applicator elements. Making the applicator interfitting elements from a translucent material is desirable then, not only to confirm correct placement as in the examples just discussed, but to allow results to be observed. After incubation and at the time deemed prudent to obtain a test result, a lid can be removed from the dish and such dual purpose interfitting elements can be re-interfitted with the dish. The interpretive indications are then cooperatively again positioned relative to the sample locations. The results of the AST portion of the assay in this example can then be directly obtained by visual comparison of the margin of the zones of inhibition with the interpretive indications, as has been described above; but in this case the indications are carried by the same dual purpose interfitting element that provides the applicator functionality. Please see FIG. 7D, FIG. 7E and FIG. 7F, which further illustrate this point.

It will be appreciated that the latter example saves having to provide additional interfitting elements 47, 48 to provide the interpretive indications. However, the examples having separate applicator and interpretive indication carrying interfitting elements have the advantage of more flexibility in making up assay kits for differencing test applications, particularly in low volumes where the ease of manufacture of numerous different versions of the overlay elements on films such as transparency film are significant. In one example, the most commonly used interpretive indicia set-up can be printed or otherwise provided on a dual purpose applicator/interpretive interfitting element, and additional elements carrying interpretive indications for less common test applications are made available to make up kits for other test applications. In higher volumes dual purpose interfitting elements of different image patterns including interpretive indications for a number of different agent sample combinations useful in a number of different test applications can be provided, and the appropriate elements are included in the appropriate assay kits directed to the various clinical and diagnostic applications.

Detailed Description of Example Embodiments of FIGS. 6A Through 9C

Another example is illustrated in FIGS. 6A-6D, comprising an interfitting element antimicrobial agent sample applicator 80 which in this case is provided with a releasable adhesive as the primary means for attachment and release of antimicrobial agent samples such as disk-quarter segments 10. This example element can be simple in design and can also be made from a translucent material, such as a clear polymeric resin. As with the element before described, this example can be made using an injection molding process. The Interfitting element 80 is also molded so as to be provided with stops 66 and release access holes 60 as before described. A set of antimicrobial disk quarters 10 are shown ready for attachment to the interfitting element in the FIG. 6A, and then as attached in subsequent figures.

This example embodiment uses a releasable adhesive such as a pressure sensitive adhesive (PSA), designed for removable attachment applications, to affix the disk-fractions to the applicator. In one embodiment the releasable adhesive is first applied to the applicator interfitting element 80. Afterward the sample disk quarters segments are attached, and are retained on the applicator element by the releasable adhesive. The releasable adhesive can be applied just to the locations where the samples will be attached. In one example embodiment a double sided tape having an aggressive adhesive on one side and a releasable adhesive on the other side can be used. An example of this can be 3M's Repositionable Tape, 9415PC. This tape has a low tack acryl ate adhesive on the back side and a high tack acryl ate adhesive on the face side and the product uses a clear polyester carrier. In the latter case, sample attachment pieces are cut from the tape and holes are provided in the tape pieces corresponding with the release access holes 60 that the releasable adhesive pieces will be disposed over and around when attached to the element. Whether directly applied to the element or applied in the form of a double sided tape, The releasable adhesive is selected to not interact chemically with the antimicrobial agent in the sample disk segments or be water soluble. The releasable adhesive is also selected to hold the sample disk segments in place during shipping, handling and storage, but allow release of the samples when pushed away from the applicator, for example by using a release tool 78 as before described. Conventional releasable adhesives meeting these criteria are commercially available as in the example described above.

FIG. 6B illustrates a loaded interfitting element 82. The stops 66 are placed in such a way that another element 82 can be placed in adjacent chamber without interference between these stops and the other applicator's stops. Another example of this is shown in the figures, and described above, in connection with the interfitting element applicators (74, 76 in FIG. 4B) before described, and that example is commended to the reader as further illustrative of this feature. FIG. 6C shows the interfitting element 82 placed into a susceptibility-test chamber 24. From the forgoing it will be appreciated that another element (not shown) such as element 82 (but mirror-image reversed) can be inserted into the AST chamber on the right in the manner illustrated in FIG. 4B, and as discussed above in connection with the other example(s).

In a manner similar to that discussed above, the sample disk segments 10 can be deployed onto the growth media in the dish 20 by mechanical removal by applied pressure from above straight down off the applicator. FIG. 6D illustrates the process of removing a disk quarter 10 from the element 82 using a disk removal tool 78. The stops 66 hold the element 82 slightly away from the chamber's agar-based growth medium just as before described. This allows for predictable and reliable and consistent detachment and seating of the disk-quarters on to the surface of the growth medium in the chamber 24 using tool 78 at the desired sample locations as in the example (s) discussed above. This, again, so that the sample locations are coordinated with interpretive indications carried on this or another interfitting element.

In one example a center portion of the applicator 80 is open. In that case the applicator can remain in place for the incubation period as will be discussed below, if desired. It can be removed leaving the disk-quarters 10 behind as is the case with the other examples discussed if that is desired.

The examples shown in FIG. 6E to FIG. 6H are equivalent to those of the above discussion for FIGS. 6A, 6B, 6C, and 6D except that there is a mixture of disk-quarters 10 and disk-halves 86 in FIG. 6E to FIG. 6H. In Addition, FIG. 6F illustrates a disk-quarter and disk-half loaded interfitting element 84. As discussed above, disk half segments create a slightly larger zone of inhibition, but allow standard Kirby Bauer distance values to be used. Advantages and disadvantages of the respective disk segment sizes will be appreciated from the discussion of the use of disk-halves 86 given previously.

With reference to all the examples of FIGS. 6A-H, as is the case with the examples discussed above in connection with FIGS. 3A-4E, these interfitting element examples can also be adapted to a dual purpose by provision of interpretive indications on the interfitting elements 82, 84. Again (if the center portion is not open) in this example the interfitting element in each instance is removed after sample application to the growth media, and a dish lid is fitted (usually), during incubation. After incubation, the interfitting element is again interfit in each case, and the interpretive indications used to determine an AST result. If the central portions of the interfitting elements are open the interfitting elements can remain in the chamber during incubation.

Returning to a concept mentioned above, the sample size and configuration can influence the diffusion properties of the antimicrobial agent in agar-based growth media of the examples discussed. As will be appreciated at this point in the disclosure (including the previous disclosure incorporated herein by reference), the placement of the samples adjacent walls of the chambers allows smaller samples to be used than are used in convention standardized Kirby-Bauer methodology. While seven samples are shown in the illustrated embodiments, with smaller sample sizes (and corresponding closer interpretive indicia for each sample) a larger number of samples can be used.

FIGS. 7A, 7B and 7C illustrate the Kirby Bauer whole disk 88, half disk 86 and quarter disk 10 sample disk segments, below corresponding square paper samples of the same areas 90, 92, and 94. Many clinical microbiology laboratories routinely use the Kirby Bauer method for testing common, rapidly growing, and certain fastidious bacterial pathogens. This method is also the most thoroughly described disk diffusion method for which interpretive standards have been developed, supported by laboratory and clinical test data. These standards are periodically reviewed and adjustments made as new agents are introduced into the clinical formulary. A whole Kirby Bauer paper disk impregnated with a specified amount of antimicrobial agent is shown in FIG. 7A and is assumed in the table below. These example antimicrobial agents can be used in the embodiments described in the disclosure. However, other sample paper sizes and geometries could also be used, and be equivalent, such as the squares shown above the disk and disk segments in these figures. This is generally true as long as the amount of sample in the paper and the areas of the paper match those of a disk or disk segment. In embodiments where the quarter disk is used, it would be equivalent to use instead a square with an area of 7.069 mm². The weight of antibiotic added to the square would be 0.25× of a whole disk. For instance when using Nitrofurantoin, 300 microgram/4=75 micrograms would be added to the 7.069 mm² square for replacement of the quarter disk. For the half disk, 150 micrograms of Nitrofurantoin could be added to a square with an area of 14.137 mm² and be equivalent to the half disk.

Turning now to FIGS. 7D, E, and F, another example embodiment of a dual purpose interfitting element will be discussed. This example can be similar to that shown in FIGS. 6A-6H when a central part of the previous example is removed. FIG. 7D illustrates an example interfitting element 96 formed of a polymeric resin that is translucent. The interfitting element includes interpretive indications, e.g. 102, 104. The example embodiment in such an interfitting element enables placement of the antimicrobial samples into a disk chamber, but in contrast to the previously described examples that cover the dish chamber when interfitted, it can stay in place through the incubation. It then enables direct determination of results of the AST, i.e. "susceptible," "intermediate" or "resistant" values with respect to each antimicrobial agent for the organism under test, using the interpretive indications as before discussed. The element is configured for not restricting air space and movement of air, if any, in the space above the growth medium during incubation. The center of the interfitting element is generally hollow. This also heads off the possibility of fogging of the translucent material of the element during the incubation period. The antimicrobial agent samples 10, again in the form of disk segments in the illustrated example, can be attached with a releasable adhesive, such as a pressure sensitive adhesive or another adhesive that has essentially clean release properties. The purpose of making the adhesive releasable is to insure the samples can be placed down into good contact with the growth media, even if a meniscus is present adjacent a wall, as will be discussed below.

In another example, other types of adherence using other adhesive types may be used. For example it is also possible to use a chemically inert (with respect to the antimicrobial agent) non-release adhesive. An epoxy, a thermal-setting adhesive, or radiation cross-linking adhesive are examples well known and widely commercially available. In another example the element material itself can be activated for attachment by use of a solvent or heat to activate the surface, then allowing the material to cure in contact with the sample paper to effect attachment. This more permanent attachment concept can be used particularly to advantage if the growth media surface is essentially orthogonal to the chamber wall close to the chamber wall. For example, if the walls of the chamber were treated with a hydrophobic material layer 110 that would prevent the formation of a meniscus as shown at 112 in FIG. 7G, this will allow the agar to assume a more planar configuration and right angle disposition adjacent the chamber wall. This in turn allows the interfitting element to apply the samples so as to sit flush on the surface of the medium with the antimicrobial papers of the sample fully contacting the surface of the medium. Another option would be to use a plate with a low surface energy such as a polypropylene plate.

In another example embodiment the interfitting element 96 enabling placement during incubation can be made thicker and contain cavities that can hold the antimicrobial samples in place with or without a releasable adhesive. For example, the hold-enhancing measures described above can be used in such cavities. Moreover, such cavities could also be any shape to receive a like-shaped antimicrobial sample. Whether a releasable adhesive, such as a PSA, or a frictional hold, is used in examples where release (at least to some extent) of the samples from the interfitting element applicator is desired even though the interfitting element is to remain in the chamber (such as to accommodate an inclination in the surface of the growth medium due to a meniscus) provision to do this can be made. FIGS. 7D-F show the release access hole 60 for seating the antimicrobial samples on the agar in examples where at least partial release is desired.

As mentioned, in one example the interfitting element can be relatively thicker, and in another it can be relatively thinner. In one example consistent with the example shown, the body 98 of the element is formed of a translucent material, for example a PET film as described previously in connection with the example of FIGS. 2A-F or another printable translucent film material. Interpretive indications for resistant 102 and susceptible 104 are shown to illustrate the idea of the different types of indications possible in the illustrated embodiment. Another possible benefit of using thinner material is that it can more easily deform to achieve good contact between the sample papers and the growth medium, e.g. to accommodate inclination in the surface of the growth medium due to a meniscus.

Different sample configurations can also be used. FIG. 7E illustrates an example interfitting element 106 with attached disk quarters 10, while FIG. 7F shows an example interfitting element 108 with a mix of disk quarters 10 and disk halves 86. As discussed above, samples of different sizes and configurations can be used; the guiding principle being that the sample is coordinated with diffusion in the growth medium to be used and the interpretive indications. This to provide an accurate direct result reading by comparison of a margin of the zone of inhibition of a lawn growth of a microorganism under test with said interpretive indications, for example those shown in the illustrated example.

With reference to FIGS. 8A and 8B, in another embodiment the interfitting element 116 can comprise a dish lid. The dish lid can comprise at least one of a) pillars extending downward, each having an antimicrobial agent sample thereon (the pillars lengths being selected to place the samples on the growth media without holding the lid unduly off the dish, and ideally just as would normally be the lid's position), and b) interpretive indications allowing a direct determination of an AST result. In this illustrated embodiment corresponding interpretive indications can be carried on the dish bottom, as shown in FIG. 8A. That figure illustrates an example embodiment in a dish 114 with interpretive indications permanently printed on or attached to the dish bottom. This repeat of the interpretive indications is done to mitigate the problem of parallax, since the lid is relatively far from the growth media. In interpreting the result the user visually aligns the interpretive indications on the bottom of the dish and on the lid, then compares the margin of the zone of inhibition to the indications in each case for each antimicrobial agent sample. In some cases, for example when blood agar is used, a backlight can be used to illuminate the dish so that the interpretive indications can be more clearly seen through the growth media in mitigating parallax, as well as the margin of the zone of inhibition in relation thereto.

FIG. 8B illustrates the dish lid example embodiment in an interfitting element 116 comprising a dish lid with interpretive indications 51 permanently carried by, printed on, or attached to, said dish lid. A bright light under or behind the BA chamber can be used as mentioned; or in another example sunlight directly from behind—or reflected so as to pass through the dish to the user—may also be sufficient for viewing the interpretive indications on the bottom of the plate through such a relatively darker growth media.

In one example embodiment an interfitting shape, such as complementary projection and indentation, ridge and groove, etc. or a visual mark can be used to align the lid with the dish for proper registration of the locations of the samples and the interpretive indications, as well as the top and bottom interpretive inductions with each other (if twice provided to mitigate parallax in the example given above). In another embodiment the dish and lid can be shaped so they only fit together in one way, as opposed to being fittable, but rotating and fully seating only when properly aligned, for example. The overall shape of the dish and lid, or a series of raised and lower portions of the outer wall and inner walls of the dish and lid preventing them coming together unless properly aligned, to name two examples, can provide this functionality.

With regard to using a back light in a more general sense a back light can in certain example embodiments be used to enhance the visibility of the margin of the zone of inhibition. If the visibility of the growth margin can be enhanced, it will be observable earlier in time in incubation. Also light interaction with colonies may be of assistance in presumptive ID in that certain organisms react distinctively with certain light spectra. This can be used to get a result earlier than might otherwise be the case. For example, using light spectra which enhance visibility of the margin, or the simple device of backlighting so that light is blocked by microorganism growth rather than reflected by it to an observer's eye, the margin may be detectable at an earlier time. This shortens the incubation time required to get a result. A backlight having a limited spectra may enhance this effect in some circumstances. In one embodiment the interfitting element can have a light filter property, which allows a conventional broad-spectrum light to be used to illuminate, or to backlight, a set-up and incubating dish 22, but provide a view to an assay user of light limited as to spectra in a way helpful in at least one of identifying a predominating species and discerning the margin of the zone of inhibition for purposes of obtaining an AST result.

With reference to FIGS. 9A-C in another example embodiment a more conventional Kirby-Bauer set-up assay can be modified to incorporate the inventive concept to advantage. For example FIG. 9A illustrates a Standard Kirby Bauer dish containing Mueller Hinton agar. It is loaded with 12 antimicrobial agent sample disks and swabbed with a bacterial sample (previously added before placement of the disks as is known in the art). For accuracy the disks have been applied using a modified commercially available dispensing apparatus that puts them on in precisely the same position in the dish every time. For example such a dispenser is commercially available from Becton-Dickinson and Company, BBL division, Cockeysville Md., and is modified to cooperate with a dish to achieve registration in placement of the samples with interpretive indications coordinated with sample locations in the dish. Said interpretive indications can be on at least one of the dish bottom and dish lid, and can be on both with further provision of means to achieve registration of the lid indications with the dish indications. In one example as illustrated, an indexing mark 122 is provided that can be used to line up one or more of the sample dispenser, dish lid and a separate overlay interfitting element in FIG. 9B with the dish so the images on the interfitting element (be it a dish lid or separate overlay element) line up directly over the placed antimicrobial sample disks.

FIG. 9B illustrates a separate interfitting element 124 with interpretive indications in an example embodiment used with the Kirby Bauer assay set up in the dish shown in FIG. 9A. As to each placed sample disk it can comprise any one of the antimicrobial agent disks available, and can be used as listed in the table set forth below, for example, which may be a function of the type of bacterial sample applied to the growth media in the dish. A lid indexing mark 132 is shown at the top of the interfitting element in the drawing. A Kirby Bauer antimicrobial disk image 126 is illustrated on the interfitting element which corresponds to the disk 88 on the dish 118 along with a resistant interpretive indication 128 and a susceptible interpretive indication 130 for a given agent on the interfitting element.

FIG. 9C illustrates the interfitting element 124 interfit with the dish, showing the interpretive indications in an embodiment used with Kirby Bauer assay as inserted into the Kirby Bauer dish 118 for a determination of susceptible, intermediate or resistant.

| TABLE OF ANTIMICROBIAL AGENTS | WEIGHT/DISK |
|---|---|
| Amikacin | 30 mcg |
| Amoxicillin with Clavulanic Acid | 20/10 mcg |
| Ampicillin with Sulbactam | 10/10 mcg |
| Ampicillin | 10 mcg |
| Azithromycin | 15 mcg |
| Azlocillin | 75 mcg |
| Aztreonam | 30 mcg |
| Bacitracin | 10 units |
| Carbenicillin | 100 mcg |
| Cefaclor | 30 mcg |
| Cefamandole | 30 mcg |
| Cefazolin | 30 mcg |
| Cefdinir | 5 mcg |
| Cefepime | 30 mcg |
| Cefixime | 5 mcg |
| Cefmetazole | 30 mcg |
| Cefonicid | 30 mcg |
| Cefoperazone | 75 mcg |
| Cefotaxime/Clavulanic Acid | 30/10 mcg |
| Cefotaxime | 30 mcg |
| Cefotetan | 30 mcg |
| Cefoxitin | 30 mcg |
| Cefpodoxime | 10 mcg |
| Cefprozil | 30 mcg |
| Ceftazidime/Clavulanic Acid | 30/10 mcg |
| Ceftazidime | 30 mcg |
| Ceftibuten | 30 mcg |
| Ceftizoxime | 30 mcg |
| Ceftriaxone | 30 mcg |
| Cefuroxime | 30 mcg |
| Cephalothin | 30 mcg |
| Chloramphenicol | 30 mcg |
| Cinoxacin | 100 mcg |
| Ciprofloxacin | 5 mcg |
| Clarithromycin | 15 mcg |
| Clindamycin | 2 mcg |
| Cloxacillin | 1 mcg |

-continued

| TABLE OF ANTIMICROBIAL AGENTS | WEIGHT/DISK |
|---|---|
| Colistin | 10 mcg |
| Doxycycline | 30 mcg |
| Enoxacin | 10 mcg |
| Ertapenem | 10 mcg |
| Fosfomycin | 200 mcg |
| Furazolidone | 100 mcg |
| Gatifloxacin | 5 mcg |
| Gentamicin | 10 mcg |
| Gentamicin | 120 mcg |
| Imipenem | 10 mcg |
| Kanamycin | 30 mcg |
| Levofloxacin | 5 mcg |
| Lincomycin | 2 mcg |
| Linezolid | 30 mcg |
| Lomefloxacin | 10 mcg |
| Meropenem | 10 mcg |
| Mezlocillin | 75 mcg |
| Minocycline | 30 mcg |
| Moxalactam | 30 mcg |
| Moxifloxacin | 5 mcg |
| Nafcillin | 1 mcg |
| Nalidixic Acid | 30 mcg |
| Neomycin | 30 mcg |
| Netilmicin | 30 mcg |
| Nitrofurantoin | 300 mcg |
| Norfloxacin | 10 mcg |
| Novobiocin | 30 mcg |
| Ofloxacin | 5 mcg |
| Oxacillin | 1 mcg |
| Oxolinic Acid | 2 mcg |
| Oxytetracycline | 30 mcg |
| Penicillin | 10 units |
| Piperacillin/Tazobactam | 100/10 mcg |
| Piperacillin | 100 mcg |
| Polymyxin B | 300 units |
| Quinupristin/Dalfopristin | 15 mcg |
| Rifampin | 5 mcg |
| Sparfloxacin | 5 mcg |
| Spectinomycin | 100 mcg |
| Streptomycin | 300 mcg |
| Streptomycin | 10 mcg |
| Sulfachloropyridazine | 0.25 mg |
| Sulfachloropyridazine | 1.0 mg |
| Sulfadiazine | 0.25 mg |
| Sulfamethizole | 0.25 mg |
| Sulfamethoxazole with Trimethoprim | 23.75/1.25 mcg |
| Sulfathiazole | 0.25 mg |
| Sulfisoxazole | 0.25 mg |
| Telithromycin | 15 μg |
| Tetracycline | 30 mcg |
| Ticarcillin with Clavulanic Acid | 75/10 mcg |
| Ticarcillin | 75 mcg |
| Tigecycline | 15 μg |
| Tobramycin | 10 mcg |
| Trimethoprim | 5 mcg |
| Triple Sulfa | 0.25 mg |
| Vancomycin | 30 mcg |

Detailed Description of the Examples of FIG. 10A-FIG. 12

With reference to FIGS. 10A and 10B in another example embodiment an interfitting element 140 is configured for use with standard disks 88. It is adapted to function as before described in connection with disk fractions, but in this example for whole disk application. The interfitting element includes three disk applicator bosses 144 configured to hold and store standard Kirby Bauer disks (or their equivalent). This structure keeps the disks firmly in place until they are discharged in a manner essentially as before described at the time of use of the assay. The interfitting element can be loaded with the disks at the factory and can be sterile packaged with desiccant and this can allow longer shelf life for distribution and storage of the assay kit 13. Keeping the antimicrobial papers dry can be important along with recommended storage of the kits in a refrigerated, or other stable lower-temperature environment. A cool, constant temperature can also better preserve the agar-based plates of the kit.

As before mentioned, the interfitting element 140 is provided with stops 66 at four locations. These cooperate with wall portions of the dish (not shown) to support the interfitting element as it sits on the dish. Also, a notch 143 in a handle 141 of the interfitting element cooperates with the outer wall of the dish (not shown) to support the interfitting element. These arrangements are provided so that the interfitting element cooperates with the dish to place it at a desired position with respect to the dish and the growth medium in the dish (not shown) when it is interfitted. The bosses 144 then sit in close proximity to the growth medium, for example about 1 mm from the surface of the agar, when the interfitting applicator element is fitted to the dish. The close proximity assures more exact placement of the antimicrobial agent sample disks 88 on the surface of the agar at an intended antimicrobial sample location.

With reference to FIG. 10C four sample engagement teeth 146 help provide a snug fit of the paper disk 88 to enable more secure retention within the boss portion 144. A different number of teeth can be used, for example one, two, three, or a multiplicity of small teeth all around the inner wall 150 of the boss. A chamfer 148 is provided and allows for more easy charging (placement) of the disk into the boss. Other ways of retaining the disk in the boss portion can be used, for example a releasable attachment to a base portion 152 of the boss portion could be provided with a releasable low tack adhesive. In another embodiment a sealing material can be provided between the base portion 12 and an inserted disk, and a piercable diaphragm (not shown) can be used to cover the upper side of the hole 142 (lower side in this figure) to retain a slightly sub-atmospheric pressure between the diaphragm and the disk to hold the disk in place until it is to be deployed onto the growth medium (not shown) at the time of use by piercing the diaphragm. In another embodiment a disk can be releasably held in the boss portion by a plug (not shown) extending through the hole 142 with releasable adhesive tip. The plug can be removable from top side (side opposite the boss portion) by its attachment to a graspable element (not shown) such as a thin sheet of polymeric material, paper, etc. having a graspable tab. In one embodiment plugs for all three disks are attached to the same graspable element. When the graspable element is pulled away from the interfitting element, taking the plug(s) with it, the disk(s) 88 are released and drop onto the growth medium. The tack of the releasable adhesive and the size of the plug(s) are coordinated so that this is enabled without pulling the interfitting element up off the dish.

With reference to FIG. 10D an antimicrobial sample disk 88 is charged (fitted) into the boss portion 144 of the applicator interfitting element—for subsequent application off the applicator onto a growth medium (not shown in the figure). When charged, the disk in the boss portion deforms and appears as shown in FIG. 10E. Disk deformation 154 caused by each sample engagement tooth 146 causes a rebound force which increases frictional engagement and helps keep the disk in place until it is intentionally deployed onto the growth medium (not shown).

With reference to FIG. 10F two interfitting elements 140 are placed in the dish 20 in the desired chambers for DAST. In one embodiment a polymeric resin material from which each element is made (by a molding process, as mentioned) can be tinted, or left clear, to provide a color indication of which chamber of the assay dish the element is intended to be placed over. For example, in one embodiment a red tint can be used to indicate that the interfitting element is to be used with a chamber with a blood ager (e.g. the BA medium shown), whereas the material of an interfitting element intended to be used over a chamber having un-tinted agar can be left un-tinted. This combined with the shapes of the elements makes loading the correct sample disks onto the correct sample locations in the respective chambers convenient, faster, and less prone to error. In another example embodiment (not shown) other information (such as growth media type, chamber location, sample source (e.g. urinary, non-urinary, etc.), identification of antimicrobial agents to be placed, etc. can be provided on the element(s) by molding, printing, labeling or another known means. Likewise, instead of a color indication of intended chamber use, a written or other symbolic chamber designation can be provided on the element as just described.

The disks are deployed using the release tool 158 as before described. The boss portions (on the underside of the interfitting elements and not visible in this view) guide the dropping disks onto the desired sample locations more accurately. With reference to FIG. 10G after the applicator interfitting elements are removed the BA 25 and MH 26 growth media chambers with bacterial sample applied 162,164 respectively, now have the released and placed antimicrobial agent sample disks 88 on the agar surface. Also shown is the isolation scheme 200 of the added bacterial sample for Columbia CNA agar with blood (CCNAB) isolation/identification chamber and MacConkey agar (MAC) isolation/identification chambers as described above, for example in connection with FIG. 1C. Returning to FIG. 10G, a sterile culture swab 12 is used to apply sample uniformly to the BA 25 and MH 26 chambers and also the first pass 32 of sample into CCNAB 28 and MAC 30 chambers. The spreading tool 16 is then used to perform the second and third spreading passes 34, 36, respectively as before described and as known in the art. The different antimicrobial agents contained in the sample disks 88*a, b, c, d, e*, and *f* can be coordinated with the growth media in the respective chambers 162, 164 to comprise the likely agents for treatment of infections of the type the microbial sample under test is suspected to be, or which are most likely for the sample source (wound, urine, upper respiratory, lower respiratory tract, etc.) in the illustrated example.

Turning now to FIG. 10H, set-up-and-incubated assay dish 166 is ready for a result determination. The isolation portion of the assay comprising chambers 28, 30 to which were applied a portion of the specimen according to the isolation scheme before described are showing gram negative isolated colonies 37 (the appearance of pure culture with a measurable concentration). The concentration appears to be within the range for a valid DAST result, in accordance with the discussion above, and as will be further touched on in connection with FIG. 12. Returning to FIG. 10H, in the antimicrobial susceptibility portion comprising chambers 168, 170 to which sample disks were applied (at specific sample locations 41), circular zones of inhibition are now visible. Two translucent interfitting elements 173,176 carrying interpretive indications, in the illustrated example being specific for urine cultured specimens with indicated growth media types marked thereon are ready for interfitting with the dish to facilitate determination of whether the microorganism is susceptible to each of the agents included in the applied disks 88. With reference now to FIG. 10H the last stage assay dish 178 with the interfitting elements (173, 176 in FIG. 10H) fitted into the chambers (168, 170 in FIG. 10H) enables direct reading of the results of the DAST as previously described. For clarity of presentation the results illustrated are "susceptible" as to each agent in the example shown in the figure. The disk image or indication circle 174CF is directly over the CF disk, and thus superimposed on the sample location, as is the case with the other disk images, which are likewise superimposed on the disks lying in the chambers. The margins formed by the zones of inhibition can thus be directly compared to the indications (e.g. 174 CFr, 174 DFi, 174 CFs) to obtain the DAST result with regard to each antimicrobial agent in terms of "resistant," "intermediate" or "susceptible" as described above.

With reference to FIG. 10J an incubated assay dish 180 similar to that just described, but set up for a microbial sample from a non-urinary tract source, such as wound, respiratory tract, or other location is ready for obtaining a result. The isolation performed is showing gram-positive isolated colonies (the appearance of a mixed culture but the gram positive isolated colonies are predominating with only a very minor gram negative species shown of two colonies in the MAC chamber). Again the concentration appears to be within the range for a valid DAST result. Again the interfitting elements 189, 192 carrying interpretive indications can now be fitted. As with the other examples described these are coordinated with the antimicrobial agent sample disks to give a direct results indication in each case. In the illustrated example these are specifically chosen for likely candidate agents for treatment of non-urinary infections, other types of cultured specimens such as wound, lower respiratory tract, etc., with indicated growth media types marked thereon. Of course as with all the examples where the applicator and interpretive indications are embodied in different interfitting elements these are coordinated in the assay so that the agent samples, sample locations on appropriate growth media, etc. are set up to give more accurate results. As mentioned these can be further coordinated to address likely agent treatment options for particular suspected infections or specimen sources from the patient's body.

With reference to FIG. 10K, a final step assay dish 194 with interfitting elements (189, 192 in FIG. 10J) fitted enables a direct reading of the DAST result as described above. A presumptive identification of the microorganism and determination of susceptibility (or not) to agents with which the sample under test was incubated is enabled.

With reference to FIG. 11, in another example embodiment interpretive indications (e.g. 198*a*, 198*ar*, 198*ai*, 198*as*) are carried on the applicator interfitting element 196. In this example the interfitting element is formed of a translucent or transparent material. This element comprising an antimicrobial sample whole disk applicator with interpretive indications is used to apply the sample disks (88 in the figures) to the growth medium (not shown), and is then removed—but retained for when the specimen has been incubated—after which it is re-fitted to enable a DAST result to be determined. Thus this interfitting element is used twice in the assay. The first time to apply the disks, and the second time after the incubation period for providing the interpretive indications superimposed with and coordinated with the sample locations and margins of zones of inhibition of the incubated sample culture to enable the susceptibility test interpretations of resistant, intermediate or susceptible as described above.

It will be appreciated that a bottom view of this example interfitting element would be identical to that shown in FIG. 10A in terms of the three whole disk applicator bosses 144 being provided and other structure as described above.

With reference to FIG. 12 a pictorial illustration of standardized isolations of bacteria useful for approximating the concentration of bacteria (in colony forming units per milliliter) present in the sample is provided. The colony isolation scheme 200 used for these standards is in lower right of the figure.

CONCLUSION, RAMIFICATIONS

With reference to the foregoing, the reader will appreciate that the invention as discussed in connection with example embodiments can enable a faster and simpler direct antimicrobial susceptibility test. The improved methodology incorporating the innovations and enhancements taught in this disclosure can also increase the test's precision, accuracy and reliability. Because of the improvements, such a test is simpler to use which makes the test attractive as a point-of-care system for doctor's offices and clinics. Particularly as provided in an assay in accordance with the principles of the invention and the examples disclosed herein the invention can provide improved means for obtaining susceptibility information useful in diagnostic and treatment applications of such an assay.

The ongoing rise, if not to say explosion, of antibiotic-resistant infections continues to plague health care. The improved DAST assay can help to lengthen the antibiotic era by allowing doctors to prescribe less costly and/or more targeted antibiotics, instead of the current approach of prescribing broader spectrum antimicrobial agents based on an educated guess whether it will be effective; which generally results in prescribing a more powerful and/or broader spectrum antimicrobial agent than is actually needed. Health care workers can use evidence-based medicine, here by using the disclosed assay, to treat of infections, thus helping to preserve the efficacy of the remaining "big gun" antibiotics (that is to say effective, broad spectrum, and valuable antimicrobial agents still effective in treating most organisms).

I will now list some of the advantages of the invention as disclosed in example embodiments over the prior art disk-fraction-diffusion antimicrobial susceptibility test methodology:

(1) User time commitment with prior art methods: "The diagnostic method, not including record keeping, currently requires on an average between 4 to 8 minutes to set-up plus 4 to 8 minutes to process following incubation."

(1A) User time commitment with Improvements: It has been found that the set-up of the method using pre-loaded antimicrobial agent applicators takes, on an average, 1 to 2 minutes. The post-incubation processing using measuring films take 1 to 2 minutes on an average. This can dramatically increase the productivity of lab personnel; and it can reduce the cost per test, and enable more tests to be done at a facility in a given time period.

(2) Prior art application of antimicrobial papers: In one embodiment of the prior art, "The method by which the antimicrobial disk-quarters are applied to the chambers can be cumbersome and time consuming. Applicator 18 stabs and picks up the antimicrobial-disk-quarter papers 10 for placement into the BA and MH chambers 25 and 26. The user must place the disk-quarters so that they equidistantly abut the edge of the dish or fit into the corners . . . . This takes practice and dexterity to become proficient for this step of the test. In addition, there is a possibility that the disk-quarter may release from the pin before making it to its position in the chamber. If the disk-quarter lands on the agar, there starts a release of antibiotic into the agar, which compromises the test. The disk-quarters are color-coded and need to be placed in the appropriate positions in each of the chambers. This requires the user to be cautious in making certain that the disk-quarters are placed appropriately and are not mixed up. Another issue that requires care is seating of the disk-quarters on the agar. The user gently taps the disk-quarter to seat them on the agar. If they are pressed to hard, they may travel below the surface of the agar, which is undesirable and can also compromise the results".

(2A) Improvement in applying antimicrobial papers: Antimicrobial disk-fractions are generally added to the chambers using a pre-loaded interfitting element. These elements can be loaded during manufacturing, in which case the examples require the user only to drop them into the susceptibility test chamber 24, and then dislodge or seat the disk-fractions onto the agar using the release tool 78. This also allows for an accurate match of the placed disk fractions to the interpretive indications. In examples where the applicator is loaded in the lab, the process is still easier and more accurate, and takes less time.

(3) Prior art measurement of zones of inhibition and interpretation to "resistant", "intermediate" or "susceptible": Following the incubation period of the kit plate 22, various zones of inhibition are shown 43 generated by the various antimicrobial agent disk-fractions 10 to the predominating species growing in the chambers 42. The sizes of the zones of inhibition are defined by the margins of inhibition 44. The user measures the zones in millimeters using a ruler or sliding caliper from the edge or corner of the chamber to the margin 44. The zones of inhibition 43 measured by the user are compared and matched to the standard Interpretive values of a Zone Radius Interpretive Standards table such as the one illustrated in FIG. 1F.

(3A) Improvement in obtaining a resistant, intermediate or susceptible result: The specification and several of the drawings of this application teach the use of interfitting elements with interpretive indications. This allows the user to read out a "resistant", "intermediate" or "susceptible" result directly without the use of a Interpretive Standards table. Interfitting elements can have other shapes and methods of holding and releasing the antimicrobial samples. It is also important to provide a dry environment for the antimicrobial samples when they are loaded onto the interfitting elements. The elements are sealed in a water impermeable material containing a desiccant, to provide proper storage of the antimicrobial agent papers.

The invention has been described in terms of illustrative examples. However, these embodiments in specific examples are not to be construed as restrictive of the scope of the invention, which is defined by the appended claims, and not the forgoing discussion. Changes, modifications, different approaches, variations, and the like which can be effected with reference to what is known in the art and without resort to inventive faculty, and are within the meaning and range of equivalency of the claims as set forth below, are within their scope. Thus, care must be taken in limitation of the scope of the claims by those construing them, and no limitation by virtue of the scope of the examples provided is intended.

The invention claimed is:

1. An antimicrobial susceptibility assay kit, including:
   an assay dish, said dish including a plurality of chambers, each of said chambers comprising at least one wall;
   at least one growth medium carried by the assay dish;
   at least one chamber facilitating an antimicrobial susceptibility assay regarding at least one antimicrobial agent;
   at least one chamber facilitating isolation of microorganisms and enabling obtaining more information about microorganism in a sample under test, including at least one of: a) observation of colony characteristics so as to determine at least one of a presence of a predominating species, presence of essentially a single species, or presence of a mixed culture without predominance; b) identification of a trait of a predominating species useful in presumptive identification of the predominating species; c) enablement of further testing from at least one isolated culture; d) determination of an approximate concentration of microorganisms in the sample, e) a determination that the concentration is within a range wherein an antimicrobial susceptibility assay result carried out in said at least one chamber facilitating an antimicrobial susceptibility assay will be valid;

a visual comparison standard enabling an approximation of the concentration of the microorganism in the sample under test sufficient to confirm validity of the assay;

at least one antimicrobial agent sample;

at least one sample location;

at least one interpretive indication, positionable at a predetermined location with respect to the location of a corresponding sample location adjacent a growth medium in the assay dish where a corresponding antimicrobial agent sample can be accurately placed;

an interfitting element, said interfitting element configured to enable at least one of: a) more accurately positioning at least one antimicrobial agent sample at a sample location in contact with a growth medium; b) providing at least one interpretive indication at a predetermined location with respect to the location of a corresponding sample location adjacent a growth medium in the assay dish where a corresponding antimicrobial agent sample can be accurately placed, said interfitting element and said assay dish being configured to interfit so that the interfitting element is positioned in a predetermined way with respect to the assay dish so that they cooperate to enable in each case a more accurate relative location of an antimicrobial agent sample at a sample location with respect to at least one corresponding interpretive indication, and after incubation of a microorganism under test, in each case for said at least one corresponding interpretive indication to be visually compared with a margin of a zone of inhibition of colonies grown on one of said growth mediums to directly determine an assay result in each case.

2. An antimicrobial susceptibility assay kit as set forth in claim 1, further comprising at least two differing growth media, whereby at least one of the following is enabled:
a) said at least two differing growth media facilitating presumptive identification by at least one of: i) a difference in promotion/suppression of colony growth, and, ii) at least one of the plurality of growth media enabling at least one of enhancement and suppression of expression of at least one microorganism trait useful in presumptive identification of an organism under test;
b) at least one growth medium preferentially supports growth of gram-negative species, and one growth medium preferentially supports growth of gram-positive species, whereby presumptive identification of a predominating species as one of gram positive and gram negative is facilitated.

3. An antimicrobial susceptibility assay kit as set forth in claim 2, wherein the assay further comprises at least one of:
a) a plurality of antimicrobial agent samples and a plurality of interpretive indications, enabling determination of susceptibility to a plurality of antimicrobial agents;
b) both i) said plurality of chambers and ii) said plurality of antimicrobial agent samples and said plurality of interpretive indications enabling determination of susceptibility to a plurality of antimicrobial agents;
c) a plurality of antimicrobial agent sample locations within at least one single chamber of the assay dish, enabling a plurality of antimicrobial agent samples to be positionable in at least one chamber of said plurality of chambers of the assay.

4. An antimicrobial susceptibility assay kit as set forth in claim 1, wherein said interfitting element comprises at least one of:
a) a single interfitting element provided which enables both of
i.) more accurately positioning the antimicrobial sample at a sample location in contact with the growth medium;
ii.) carrying the interpretive indication positionable at a predetermined distance from said sample location;
b) one of a plurality of interfitting elements provided, each of which enables at least one of: i) more accurately positioning the antimicrobial sample at a sample location in contact with the growth medium; ii) carrying the interpretive indication positionable at a predetermined distance from said sample location.

5. An antimicrobial susceptibility assay kit as set forth in claim 1, where said interfitting element comprises at least one of:
a) an applicator configured for more accurately positioning at least one antimicrobial sample at a sample location coordinated with a position of an interpretive indication;
b) an overlay configured to be placed on the growth medium in at least one chamber and configured to cooperate with said dish to reliably provide at least one interpretive indication witch is coordinated with said at least one antimicrobial agent sample when said overlay is interfitted with the dish;
c) a lid which interfits with the dish and which enables at least one of said positioning of said antimicrobial agent sample and positioning of said interpretive indication;
d) a single element acting as both an applicator configured for more accurately positioning at least one antimicrobial agent sample at least one sample location, and as a carrier of at least one interpretive indication coordinated with said at least one sample location;
e) a translucent film carrying said interpretive indication;
f) a an applicator holding a plurality of antimicrobial agent samples and facilitating separation of the samples from the applicator onto at least one growth medium so as to place each of them accurately at a sample location for each sample coordinated with a corresponding interpretive indication for each sample;
g) an overlay applicator defining at least one opening therethrough allowing normal incubation, which can carry antimicrobial agent samples and can be placed and left on the growth medium during incubation, said samples each being located at a sample location when interfitted with the dish;
h) an applicator configured for more accurate placement of least one antimicrobial sample at a sample location coordinated with an interpretive indication, said applicator having at least one of: a) friction; and, b) releasable adhesive; for holding an antimicrobial agent sample;
i) an antimicrobial agent sample applicator which places at least one of said samples adjacent at least one wall of a chamber in said dish;
j) an antimicrobial agent sample applicator which places at least one of said samples adjacent at least two walls of a chamber in said dish;
k) an overlay applicator defining at least one opening therethrough allowing normal incubation which can carry a plurality of antimicrobial agent samples and can be placed and left on the growth medium during incubation, said samples each being located at a sample location when said overlay applicator is interfitted with the dish, said overlay applicator also carrying interpretive indications, each being coordinated with a sample location;

l) an applicator comprising at least one sample guide boss facilitating more accurate placement of an antimicrobial agent sample at a sample location;

m) an applicator comprising at least one sample guide boss and which can also carry at least one interpretive indication coordinated with a sample location whereat an antimicrobial agent sample can be more accurately placed using said applicator including said guide boss;

n) an applicator defining an opening adjacent a antimicrobial agent sample, enabling the sample to be applied to the growth medium by pushing it away from the applicator through said opening;

o) an applicator defining an opening adjacent a antimicrobial agent sample, enabling the sample to be applied to the growth medium by pushing it away from the applicator through said opening, wherein the assay further includes a release tool configured to cooperate with the opening in the applicator to enable more convenient application of samples to the growth medium.

6. An antimicrobial susceptibility assay kit as set forth in claim 1, wherein said at least one antimicrobial agent sample positionable at a sample location is at least one of:

a) positionable adjacent at least one wall of the dish;

b) a fractional amount of a standard Kirby-Bauer antimicrobial agent sample;

c) a fractional amount of a standard Kirby-Bauer antimicrobial agent sample carried in a standard disk carried in a fractional part of a standard disk;

d) a fractional amount of a standard Kirby-Bauer antimicrobial agent sample carried in a standard disk, carried in a different sample carrier, coordinated with an interpretive indication locatable adjacent said fractional amount and different sample carrier to give said assay result;

e) positionable away from a wall of the dish;

f) a standard Kirby-Bauer antimicrobial agent sample disk.

7. An antimicrobial susceptibility assay kit as set forth in claim 6, wherein a distance from the sample location to the interpretive indication is one of:

a) a distance that essentially correlates with that used in determining results in a Kirby-Bauer standardized antimicrobial susceptibility test;

b) a distance from the sample location to the interpretive indication that is different from that used in determining results in a Kirby-Bauer standardized antimicrobial susceptibility test, but is correlated with concentration of anti-microbial agent in the growth medium predictable from known diffusion properties of said agent in said medium so as to give results essentially as obtainable in a standard Kirby-Bauer standardized antimicrobial susceptibility test.

8. An antimicrobial susceptibility assay kit as set forth in claim 1, wherein the growth medium and configuration of at least one chamber facilitating an isolation procedure is provided to reliably enable a determination from an isolation performed therein that the concentration of colony-forming units of a microorganism in volume of a sample under test is within a range wherein an antimicrobial susceptibility procedure carried out in at least one other chamber of the dish facilitating an antimicrobial susceptibility assay will be valid.

9. An antimicrobial susceptibility assay kit as set forth in claim 1, wherein the visual comparison standard enabling an approximation of the concentration of the microorganism in the sample under test further comprises a plurality of pictorial illustrations of standardized isolations enabling a rapid visual determination that the concentration is within a range wherein an antimicrobial susceptibility assay result carried out in said at least one chamber facilitating an antimicrobial susceptibility assay will be valid.

10. An antimicrobial susceptibility assay kit, including:

an assay dish;

a growth medium in said dish;

an antimicrobial agent sample;

a predetermined sample location adjacent the growth medium in the assay dish;

an interpretive indication locatable at a predetermined location with respect to the sample location adjacent the growth medium in the assay dish the interpretive indication enabling direct visual indication of susceptibility of a microorganism under test to at least one antimicrobial agent under test;

at least one interfitting element which interfits with said dish, said at least one interfitting element being configured to enable at least one of the following: a) more accurately positioning the antimicrobial agent sample at the sample location in contact with the growth medium; b) providing the interpretive indication at the predetermined location with respect to said sample location, such relative location of the sample location and interpretive indication being enabled by interfitment and cooperation of the interfitting element with the assay dish, so as to enable said interpretative indication to be more accurately positioned and visually compared with a margin of a zone of inhibition of microorganisms grown on said medium, to enable said direct visual indication;

an isolation portion facilitating isolation of microorganisms and enabling obtaining more information about a microorganism in a sample under test, including at least one of: a) observation of colony characteristics so as to determine at least one of a presence of a predominating species, presence of essentially a single species, or presence of a mixed culture without predominance; b) identification of a trait of a predominating species useful in presumptive identification of the predominating species; c) enablement of further testing from at least one isolated culture; d) determination of an approximate concentration of microorganisms in the sample, e) a determination that the concentration is within a range wherein an antimicrobial susceptibility assay result carried out in said at least one chamber facilitating an antimicrobial susceptibility assay will be valid;

the assay enabling placing a microorganism sample on the growth medium and placing the antimicrobial agent sample at said sample location with accuracy using said interfitting element;

whereby, after incubating said microorganism for a period sufficient to allow a margin of a zone of inhibition to be discernable, a visual comparison of the location of the margin of the zone of inhibition to the interpretive indication gives a user a result immediately, by virtue of said comparison.

11. An antimicrobial susceptibility assay kit as set forth in claim 10, further comprising:

a plurality of chambers in said dish, each chamber having at least one wall;

a plurality of differing growth media in respective chambers of the dish;

a plurality of antimicrobial agent sample locations in the dish and commensurate plurality of interpretive indications in at least one of the dish and interfitting element;

a plurality of said samples at said locations in contact with at least one growth medium in at least one chamber.

12. An antimicrobial susceptibility assay kit as set forth in claim 11, further comprising:

a visual comparison standard enabling an approximation of the concentration of the microorganism in the sample under test sufficient to confirm validity of the antimicrobial agent susceptibility assay;

in said plurality of chambers carrying growth media, at least one chamber further comprising said isolation portion enabling isolation of microorganisms facilitating obtaining more information about microorganism species in a sample under test, said assay being configured so as to enable the following assay procedures to be performed at the same time as the antimicrobial agent susceptibility procedure performed in another of said plurality of chambers:

a) performing an isolation from a sample under test in accordance with a standardized procedure;

b) incubating the isolated microorganism colonies for a predetermined amount of time;

c) comparing the isolation portion to the visual comparison standard;

d) determining an approximate concentration of microorganisms in the sample under test from a visual comparison with said standard;

e) determining that the concentration is within a range wherein an antimicrobial susceptibility result will be valid by comparison of the approximate concentration to the appropriate concentration range for the antimicrobial susceptibility test performed;

f) determining whether there is a predominating species;

g) identifying at least one trait of a predominating species when a predominating species is present;

g) making a presumptive identification of a predominating species from said trait.

13. An antimicrobial susceptibility assay kit as set forth in claim 11, wherein a chamber provided for the antimicrobial agent susceptibility procedure is configured to enable one of the following procedures:

providing said sample in the form of a standardized Kirby-Bauer test disk and placing it on the growth medium away from said wall of said chamber; and providing said sample in the form of a fraction of a standardized Kirby-Bauer test disk, and placing said fraction of a standardized Kirby-Bauer test disk adjacent said wall of said chamber.

14. An antimicrobial susceptibility assay kit as set forth in claim 11, further comprising:

at least one chamber in the dish being configured for at least presumptive identification of a predominant microorganism under test, and the assay being configured to enable at least one of the following procedures:

a. spreading a sample containing microorganisms across a growth medium in said at least one chamber so as to facilitate growth of an isolated colony of a predominant microorganism on said medium, enabling at least one of:

b. presumptive identification of a predominant microorganism under test;

c. determining at least one trait of a predominant organism useful in identification of the organism using said isolated colony and knowledge of the growth promotion/inhibition properties of the particular makeup of the growth medium;

d. visual inspection of a colony of an organism under test for identifying traits of said colony;

e. spot testing of a colony of a single organism under test;

f. using a light to enhance visibility of the margin of the zone of inhibition, wherein said light is one of broad spectrum light and light of a selected wavelength;

g. using at least two different chambers with different growth media therein, facilitating presumptive identification by i) a difference in promotion/suppression growth, and ii) at least one of the plurality of growth media supporting at least one of enhancement and suppression of an expression of at least one microorganism trait useful in presumptive identification of an organism under test.

15. An antimicrobial susceptibility assay kit as set forth in claim 14, further comprising a multiplicity of chambers in the dish, enabling the following procedures:

providing at least two chambers for antimicrobial susceptibility testing, the growth media in said at least two chambers being selected to do at least one of:

preferentially support growth of different sets of organisms, thereby aiding in identification of a predominant organism;

compliment each other to together provide opportunity for successful incubation of a larger number of species of microorganisms than can be provided by a single growth medium.

16. An antimicrobial susceptibility assay, including:

an assay dish having a plurality of chambers;

a plurality of growth media carried by the assay dish in said chambers;

a plurality of antimicrobial agent samples, each placeable at a sample location adjacent a growth medium in a chamber of the assay dish;

a plurality of interpretive indications, each positionable at a predetermined location with respect to a corresponding antimicrobial agent sample location adjacent one of the growth mediums in the assay dish:

an interfitting element, said interfitting element configured to enable at least one of: a) more accurately positioning the antimicrobial samples at said locations and in contact with a growth medium; b) providing the interpretive indications at predetermined distances from said position, relative location of the sample location and the location of the interpretive indication being facilitated by the interfitting element and the assay dish being configured to interfit so that the interfitting element can be positioned in a predetermined way with respect to the assay dish so that they cooperate to enable more accurate relative location of said at least one antimicrobial agent sample at said at least one sample location with respect to said at least one corresponding interpretive indication, said assay device, after incubation so as to make a zone of inhibition discernable, enabling the interpretative indication to be directly visually compared with the margin of a zone of inhibition of microbial organism growth on said medium to directly determine an assay result comprising indication of susceptibility of a microorganism under test to at least one antimicrobial agent under test said assay enabling the interpretative indications to be directly visually compared with margins of zones of inhibition of colonies grown on said mediums to visually indicate an assay result;

at least one chamber not used in the antimicrobial susceptibility testing and devoted instead to facilitating an isolation procedure enabling at least one of: a) determination of concentration of microorganisms in a sample under test; and b) a presumptive identification of a predominant species of microorganism under test, said chamber enabling isolation of organisms and thus providing for growth of colonies from individual organisms to allow more close study of at least one organism in the sample under test.

17. An assay kit as set forth in claim 16, further including a visual comparison standard enabling an approximation of the concentration of the microorganism in the sample under test sufficient to confirm validity of the assay by visual comparison of the result of the isolation procedure with said standard.

18. An antimicrobial susceptibility assay kit as set forth in claim 17, wherein the visual comparison standard enabling an approximation of the concentration of the microorganism in the sample under test further comprises a plurality of pictorial illustrations of standardized isolations enabling a rapid visual determination that the concentration is within a range wherein an antimicrobial susceptibility assay result carried out in said at least one chamber facilitating an antimicrobial susceptibility assay will be valid.

19. An assay kit as set forth in claim 16, wherein at least two chambers are provided for organism identification and two chambers are provided for antimicrobial susceptibility testing, a plurality of antimicrobial agent samples being placeable at antimicrobial agent sample locations in each chamber provided for antimicrobial susceptibility testing.

20. An assay kit as set forth in claim 19, said dish further comprising at least three chambers, two of which are provided to facilitate isolations, and which each further comprise a growth medium which differs from that disposed in the other of the two, whereby two isolations on differing growth mediums are facilitated; and the third chamber of said at least three chambers facilitates at the same time an antimicrobial agent susceptibility test using a growth medium disposed therein that differs from at least one of the two growth mediums in said two chambers provided to facilitate isolations.

* * * * *